United States Patent
Squires et al.

(10) Patent No.: US 7,772,005 B1
(45) Date of Patent: *Aug. 10, 2010

(54) METHOD OF ESTABLISHING AN EQUINE ARTIFICIAL INSEMINATION SAMPLE

(75) Inventors: Edward L. Squires, Fort Collins, CO (US); Patrick M. McCue, Fort Collins, CO (US); George E. Seidel, Fort Collins, CO (US)

(73) Assignee: XY, LLC, Navasota, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/744,675

(22) PCT Filed: Jul. 29, 1999

(86) PCT No.: PCT/US99/17165

§ 371 (c)(1),
(2), (4) Date: Jan. 29, 2001

(87) PCT Pub. No.: WO00/06193

PCT Pub. Date: Feb. 10, 2000

Related U.S. Application Data

(60) Provisional application No. 60/094,720, filed on Jul. 30, 1998, provisional application No. 60/113,143, filed on Dec. 18, 1998.

(51) Int. Cl.
G01N 33/00 (2006.01)
G01N 22/00 (2006.01)
A61B 17/43 (2006.01)

(52) U.S. Cl. .......... 436/63; 422/73; 422/82.05; 435/6; 435/7.1; 435/7.21; 435/2; 435/4; 436/164; 600/33; 600/35

(58) Field of Classification Search .......... 435/6, 435/2, 4, 7.1, 7.21, 325; 800/2, 8; 422/73, 422/81, 99, 100, 82.05; 209/571, 576; 356/336
See application file for complete search history.

(56) References Cited

U.S. PATENT DOCUMENTS

| | | | |
|---|---|---|---|
| 3,299,354 A | 1/1967 | Hogg | |
| 3,499,435 A | 3/1970 | Rockwell et al. | |
| 3,547,526 A | 12/1970 | Devereux | |
| 3,644,128 A | 2/1972 | Lipner | |
| 3,661,460 A | 5/1972 | Elking et al. | |
| 3,687,806 A | 8/1972 | Van den Bovenkamp | 195/1.3 |
| 3,710,933 A | 1/1973 | Fulwyler et al. | |
| 3,761,941 A | 9/1973 | Robertson | |
| 3,810,010 A | 5/1974 | Thorn | |
| 3,826,364 A | 7/1974 | Bonner et al. | |
| 3,829,216 A | 8/1974 | Persidsky | 356/36 |
| 3,833,796 A | 9/1974 | Fetner et al. | |
| 3,877,430 A | 4/1975 | Wieder | |
| 3,893,766 A | 7/1975 | Hogg | |
| 3,894,529 A | 7/1975 | Shrimpton | 128/1 R |
| 3,909,744 A | 9/1975 | Wisner et al. | |
| 3,947,093 A | 3/1976 | Goshima et al. | |
| 3,960,449 A | 6/1976 | Carleton et al. | |
| 3,963,606 A | 6/1976 | Hogg | |
| 3,973,003 A | 8/1976 | Colas | |
| 3,973,196 A | 8/1976 | Hogg | |
| 4,007,087 A | 2/1977 | Ericsson | |
| 4,009,260 A | 2/1977 | Ericsson | 424/105 |
| 4,014,611 A | 3/1977 | Simpson et al. | |
| 4,067,965 A | 1/1978 | Bhattacharya | 424/105 |
| 4,070,617 A | 1/1978 | Kachel et al. | |
| 4,083,957 A | 4/1978 | Lang | 424/78 |
| 4,085,205 A | 4/1978 | Hancock | 424/105 |
| 4,092,229 A | 5/1978 | Bhattacharya | 204/180 R |
| 4,155,831 A | 5/1979 | Bhattacharya | 207/299 R |
| 4,162,282 A | 7/1979 | Fulwyler et al. | |
| 4,178,936 A | 12/1979 | Newcomb | |
| 4,179,218 A | 12/1979 | Erdmann et al. | |
| 4,191,749 A | 3/1980 | Bryant | 424/105 |
| 4,200,802 A | 4/1980 | Salzman et al. | |
| 4,225,405 A | 9/1980 | Lawson | 204/180 R |
| 4,230,558 A | 10/1980 | Fulwyler | |
| 4,255,021 A | 3/1981 | Brunsden | |
| 4,267,268 A | 5/1981 | Nelson, Jr. | |
| 4,274,408 A | 6/1981 | Nimrod | |

(Continued)

FOREIGN PATENT DOCUMENTS

BR    9704313    4/1999

(Continued)

OTHER PUBLICATIONS

Wilhelm et al. Cryobiology. 1996. 33:320-329.*

(Continued)

*Primary Examiner*—Carla Myers
(74) *Attorney, Agent, or Firm*—Cindee Ewell; Ryan Christensen

(57) ABSTRACT

Non-surgical artificial insemination is achieved for sexed and unsexed equines in a commercially practical manner and with dosages of insemination sperm which were not previously thought to be practical for commercial implementation. Practical and field usable techniques for insemination are presented as well as techniques which offer success ratios at level comparable to the existing routine, high dosage unsexed artificial insemination techniques in equines. Improved insemination and sorting systems particularly adapted to use for sex-selected sperm are disclosed.

8 Claims, 2 Drawing Sheets

U.S. PATENT DOCUMENTS

| | | |
|---|---|---|
| 4,274,740 A | 6/1981 | Eidenschink et al. |
| 4,276,139 A | 6/1981 | Lawson .................. 204/180 R |
| 4,302,166 A | 11/1981 | Fulwyler et al. |
| 4,317,520 A | 3/1982 | Lombardo et al. |
| 4,318,480 A | 3/1982 | Lombardo et al. |
| 4,318,481 A | 3/1982 | Lombardo et al. |
| 4,318,482 A | 3/1982 | Barry et al. |
| 4,325,483 A | 4/1982 | Lombardo et al. |
| 4,327,177 A | 4/1982 | Shrimpton |
| 4,339,434 A | 7/1982 | Ericsson ..................... 424/105 |
| 4,341,471 A | 7/1982 | Hogg et al. |
| 4,350,410 A | 9/1982 | Minott |
| 4,352,558 A | 10/1982 | Eisert |
| 4,361,400 A | 11/1982 | Gray et al. |
| 4,362,246 A | 12/1982 | Adair ......................... 209/3.3 |
| 4,395,397 A | 7/1983 | Shapiro |
| 4,395,676 A | 7/1983 | Hollinger et al. |
| 4,400,764 A | 8/1983 | Kenyon |
| 4,422,761 A | 12/1983 | Frommer |
| 4,448,767 A | 5/1984 | Bryant ......................... 424/85 |
| 4,474,875 A | 10/1984 | Shrimpton |
| 4,487,320 A | 12/1984 | Auer |
| 4,498,766 A | 2/1985 | Unterleitner |
| 4,501,366 A | 2/1985 | Thompson |
| 4,511,661 A | 4/1985 | Goldberg ..................... 436/503 |
| 4,515,274 A | 5/1985 | Hollinger et al. |
| 4,523,809 A | 6/1985 | Toboada et al. |
| 4,538,733 A | 9/1985 | Hoffman |
| 4,559,309 A | 12/1985 | Evenson |
| 4,598,408 A | 7/1986 | O'Keefe |
| 4,600,302 A | 7/1986 | Sage, Jr. |
| 4,605,558 A | 8/1986 | Shrimpton |
| 4,631,483 A | 12/1986 | Proni et al. |
| 4,637,691 A | 1/1987 | Uehara et al. |
| RE32,350 E | 2/1987 | Bhattacharya ........... 204/180.1 |
| 4,654,025 A | 3/1987 | Cassou et al. |
| 4,660,971 A | 4/1987 | Sage et al. ..................... 356/39 |
| 4,673,288 A | 6/1987 | Thomas et al. |
| 4,680,258 A | 7/1987 | Hammerling et al. .......... 435/7 |
| 4,683,195 A | 7/1987 | Mullis et al. |
| 4,683,202 A | 7/1987 | Mullis |
| 4,691,829 A | 9/1987 | Auer |
| 4,698,142 A | 10/1987 | Muroi et al. .............. 204/182.3 |
| 4,702,598 A | 10/1987 | Böhmer |
| 4,714,680 A | 12/1987 | Civin |
| 4,744,090 A | 5/1988 | Freiberg |
| 4,749,458 A | 6/1988 | Muroi et al. .............. 204/182.3 |
| 4,756,427 A | 7/1988 | Gohde et al. |
| 4,758,729 A | 7/1988 | Monnin |
| 4,764,013 A | 8/1988 | Johnston |
| 4,780,451 A | 10/1988 | Donaldson |
| 4,790,653 A | 12/1988 | North, Jr. |
| 4,794,086 A | 12/1988 | Kasper et al. |
| 4,818,103 A | 4/1989 | Thomas et al. |
| 4,831,385 A | 5/1989 | Archer et al. |
| 4,836,038 A | 6/1989 | Baldwyn |
| 4,845,025 A | 7/1989 | Lary et al. |
| 4,846,785 A | 7/1989 | Cassou |
| 4,877,965 A | 10/1989 | Dandliker et al. |
| 4,942,305 A | 7/1990 | Sommer |
| 4,959,354 A | 9/1990 | Barbetti |
| 4,965,204 A | 10/1990 | Civin |
| 4,979,093 A | 12/1990 | Laine et al. |
| 4,980,277 A | 12/1990 | Junila |
| 4,981,580 A | 1/1991 | Auer |
| 4,983,038 A | 1/1991 | Ohki et al. |
| 4,987,539 A | 1/1991 | Moore et al. |
| 4,988,619 A | 1/1991 | Pinkel ......................... 435/30 |
| 4,999,283 A | 3/1991 | Zavos et al. .................... 435/2 |
| 5,005,981 A | 4/1991 | Schulte et al. |
| 5,007,732 A | 4/1991 | Ohki et al. |
| 5,021,244 A | 6/1991 | Spaulding ................... 424/561 |
| 5,030,002 A | 7/1991 | North, Jr. |
| 5,034,613 A | 7/1991 | Denk et al. |
| 5,055,393 A | 10/1991 | Kwoh et al. |
| 5,079,959 A | 1/1992 | Miyake et al. |
| 5,084,004 A | 1/1992 | Ranoux |
| 5,088,816 A | 2/1992 | Tomioka et al. |
| 5,098,657 A | 3/1992 | Blackford et al. |
| 5,101,978 A | 4/1992 | Marcus |
| 5,127,729 A | 7/1992 | Oetliker et al. |
| 5,132,548 A | 7/1992 | Borden et al. |
| 5,135,759 A | 8/1992 | Johnson ..................... 424/561 |
| 5,144,224 A | 9/1992 | Larsen |
| 5,150,313 A | 9/1992 | Van den Engh et al. |
| 5,159,397 A | 10/1992 | Kosaka et al. |
| 5,159,403 A | 10/1992 | Kosaka |
| 5,162,306 A | 11/1992 | Donaldson |
| 5,167,926 A | 12/1992 | Kimura et al. |
| 5,180,065 A | 1/1993 | Touge et al. |
| 5,182,617 A | 1/1993 | Yoneyama et al. |
| 5,195,979 A | 3/1993 | Schinkel et al. |
| 5,199,576 A | 4/1993 | Corio et al. |
| 5,215,376 A | 6/1993 | Schulte et al. |
| 5,219,729 A | 6/1993 | Hodgen |
| 5,247,339 A | 9/1993 | Ogino |
| 5,259,593 A | 11/1993 | Orme et al. |
| 5,260,764 A | 11/1993 | Fukuda et al. |
| 5,298,967 A | 3/1994 | Wells |
| 5,315,122 A | 5/1994 | Pinsky et al. |
| 5,346,990 A | 9/1994 | Spaulding ................... 530/350 |
| 5,359,907 A | 11/1994 | Baker et al. |
| 5,367,474 A | 11/1994 | Auer et al. |
| 5,370,842 A | 12/1994 | Miyazaki et al. |
| 5,371,585 A | 12/1994 | Morgan et al. .............. 356/246 |
| 5,412,466 A | 5/1995 | Ogino |
| 5,437,987 A | 8/1995 | Ten et al. |
| 5,439,362 A | 8/1995 | Spaulding ................ 424/185.1 |
| 5,447,842 A | 9/1995 | Simons |
| 5,452,054 A | 9/1995 | Dewa et al. |
| 5,461,145 A | 10/1995 | Kudo et al. |
| 5,466,572 A | 11/1995 | Sasaki et al. .................... 435/2 |
| 5,467,189 A | 11/1995 | Kreikebaum et al. |
| 5,471,294 A | 11/1995 | Ogino |
| 5,471,299 A | 11/1995 | Kaye et al. |
| 5,480,774 A | 1/1996 | Hew et al. |
| 5,483,469 A | 1/1996 | Van den Engh et al. ..... 364/555 |
| 5,494,795 A | 2/1996 | Guerry et al. |
| 5,496,272 A | 3/1996 | Chung et al. |
| 5,503,994 A | 4/1996 | Shear et al. |
| 5,514,537 A | 5/1996 | Chandler ....................... 435/2 |
| 5,523,573 A | 6/1996 | Hanninen et al. |
| 5,532,155 A | 7/1996 | Ranoux |
| 5,558,998 A | 9/1996 | Hammond et al. |
| 5,578,449 A | 11/1996 | Frasch et al. |
| 5,589,457 A | 12/1996 | Wiltbank ..................... 514/12 |
| 5,596,401 A | 1/1997 | Kusuzawa |
| 5,601,235 A | 2/1997 | Booker et al. |
| 5,601,533 A | 2/1997 | Hancke et al. |
| 5,602,039 A | 2/1997 | Van den Engh ............. 436/164 |
| 5,602,349 A | 2/1997 | Van den Engh .......... 73/864.85 |
| 5,622,820 A | 4/1997 | Rossi |
| 5,641,457 A | 6/1997 | Vardanega |
| 5,643,796 A | 7/1997 | Van Den Engh et al. |
| 5,650,847 A | 7/1997 | Maltsev et al. |
| 5,660,997 A | 8/1997 | Spaulding ................. 435/7.21 |
| 5,663,048 A | 9/1997 | Winkfein et al. |
| 5,672,880 A | 9/1997 | Kain |
| 5,675,401 A | 10/1997 | Wangler et al. |
| 5,684,575 A | 11/1997 | Steen |
| 5,687,727 A | 11/1997 | Kraus et al. |
| 5,690,895 A | 11/1997 | Matsumoto et al. ........... 422/73 |
| 5,691,133 A | 11/1997 | Critser et al. |
| 5,693,534 A | 12/1997 | Alak et al. |

| | | | | | | |
|---|---|---|---|---|---|---|
| 5,700,692 | A | 12/1997 | Sweet ........................ 436/50 | 2002/0186375 A1 | 12/2002 | Asbury et al. |
| 5,707,808 | A | 1/1998 | Roslaniec et al. | 2003/0129091 A1 | 1/2003 | Seidel et al. |
| 5,708,868 | A | 1/1998 | Ishikawa | 2003/0098421 A1 | 5/2003 | Ho |
| 5,726,364 | A | 3/1998 | Van den Engh .......... 73/864.85 | 2003/0157475 A1 | 8/2003 | Schenk |
| 5,759,767 | A | 6/1998 | Lakowicz et al. | 2003/0207461 A1 | 11/2003 | Bell et al. |
| 5,777,732 | A | 7/1998 | Hanninen et al. | 2003/0209059 A1 | 11/2003 | Kawano |
| 5,780,230 | A | 7/1998 | Li et al. | 2004/0005582 A1 | 1/2004 | Shipwast |
| 5,786,560 | A | 7/1998 | Tatah et al. | 2004/0031071 A1 | 2/2004 | Morris et al. |
| 5,793,485 | A | 8/1998 | Gourley | 2004/0049801 A1 | 3/2004 | Seidel |
| 5,796,112 | A | 8/1998 | Ichie | 2004/0053243 A1 | 3/2004 | Evans |
| 5,804,436 | A | 9/1998 | Okun et al. | 2004/0055030 A1 | 3/2004 | Maxwell et al. |
| 5,815,262 | A | 9/1998 | Schrof et al. | 2004/0062685 A1 | 4/2004 | Norton et al. |
| 5,819,948 | A | 10/1998 | Van den Engh | 2004/0096123 A1 | 7/2004 | Whittier et al. |
| 5,824,269 | A | 10/1998 | Kosaka et al. | 2004/0132001 A1 | 7/2004 | Seidel et al. |
| 5,835,262 | A | 11/1998 | Iketaki et al. | 2005/0003472 A1 | 1/2005 | Muhammad |
| 5,868,767 | A | 2/1999 | Farley et al. | 2005/0112541 A1 | 5/2005 | Durack |
| 5,873,254 | A | 2/1999 | Arav | 2005/0214733 A1 | 9/2005 | Graham |
| 5,876,942 | A | 3/1999 | Cheng et al. | 2005/0244805 A1 | 11/2005 | Ludwig et al. |
| 5,880,457 | A | 3/1999 | Tomiyama et al. | 2005/0028224 A1 | 12/2005 | Ludwig et al. |
| 5,888,730 | A | 3/1999 | Gray et al. | | | |
| 5,891,734 | A | 4/1999 | Gill et al. | FOREIGN PATENT DOCUMENTS | | |
| 5,895,764 | A | 4/1999 | Sklar et al. | BR | 9704313 | 6/1999 |
| 5,895,922 | A | 4/1999 | Ho | DE | 69028526 | 2/1997 |
| 5,899,848 | A | 5/1999 | Haubrich | DE | 195 49 015 C1 | 4/1997 |
| 5,912,257 | A | 6/1999 | Prasad et al. | DE | 198 82 943.3 | 2/2001 |
| 5,916,144 | A | 6/1999 | Prather et al. | EP | 0025296 A2 | 3/1981 |
| 5,916,449 | A | 6/1999 | Ellwart et al. | EP | 0071538 A1 | 2/1983 |
| 5,919,621 | A | 7/1999 | Brown | EP | 0160201 A2 | 11/1985 |
| 5,985,216 | A * | 11/1999 | Rens et al. .................... 422/73 | EP | 0189702 A1 | 8/1986 |
| 5,985,538 | A | 11/1999 | Stachecju | EP | 0288029 B1 | 4/1988 |
| 6,002,471 | A | 12/1999 | Quake | EP | 0276166 A2 | 7/1988 |
| 6,050,935 | A | 4/2000 | Ranoux et al. | EP | A-0 366794 | 5/1990 |
| 6,071,689 | A | 6/2000 | Seidel et al. .................... 435/2 | EP | 0461618 | 12/1991 |
| 6,087,352 | A | 7/2000 | Trout | EP | 0468100 A1 | 1/1992 |
| 6,117,068 | A | 9/2000 | Gourley et al. | EP | 0570102 A1 | 3/1993 |
| 6,119,465 | A | 9/2000 | Mullens et al. | EP | 0 538 786 A | 4/1993 |
| 6,133,044 | A | 10/2000 | Van den Engh | EP | 606847 A2 | 7/1994 |
| 6,140,121 | A | 10/2000 | Ellington et al. | EP | A-0 478155 | 1/1998 |
| 6,149,867 | A * | 11/2000 | Seidel et al. .................... 422/73 | EP | 0781985 A3 | 7/1998 |
| 6,153,373 | A | 11/2000 | Benjamin et al. | EP | 1250897 A1 | 10/2002 |
| 6,154,276 | A | 11/2000 | Mariella, Jr. | EP | 1 403 633 A3 | 4/2004 |
| 6,175,409 | B1 | 1/2001 | Nielsen et al. | FR | 2574656 A1 | 1/1900 |
| 6,177,277 | B1 | 1/2001 | Soini | FR | A-2 635453 | 2/1990 |
| 6,238,920 | B1 | 5/2001 | Nagai et al. | FR | 2 647 668 A | 12/1990 |
| 6,248,590 | B1 | 6/2001 | Malachowski | FR | 2699678 A1 | 6/1994 |
| 6,263,745 | B1 | 7/2001 | Buchanan et al. | GB | 0030480.1 | 1/2001 |
| 6,283,920 | B1 | 9/2001 | Eberle et al. | JP | 61139747 A | 6/1986 |
| 6,357,307 | B2 | 3/2002 | Buchanan et al. | JP | 61159135 A | 7/1986 |
| 6,372,422 | B1 | 4/2002 | Seidel et al. | JP | 20204535 | 1/1990 |
| 6,395,305 | B1 | 5/2002 | Buhr et al. | JP | 4126064 A | 4/1992 |
| 6,411,835 | B1 | 6/2002 | Modell et al. | JP | 4126065 A | 4/1992 |
| 6,463,314 | B1 | 10/2002 | Haruna | JP | 4126066 A | 4/1992 |
| 6,489,092 | B1 | 12/2002 | Benjamin et al. | JP | 4126079 A | 4/1992 |
| 6,524,860 | B1 | 2/2003 | Seidel et al. | JP | 4126080 A | 4/1992 |
| 6,528,802 | B1 | 3/2003 | Karsten et al. | JP | 4126081 A | 4/1992 |
| 6,534,308 | B1 | 3/2003 | Palsson et al. | SU | 1056008 | 11/1983 |
| 6,537,829 | B1 | 3/2003 | Zarling et al. | SU | 1260778 A1 | 9/1986 |
| 6,577,387 | B2 | 6/2003 | Ross, III et al. | WO | WO 88/07198 | 9/1988 |
| 6,590,911 | B1 | 7/2003 | Spinelli et al. | WO | WO 90/13315 A1 | 11/1990 |
| 6,604,435 | B2 | 8/2003 | Buchanan et al. | WO | WO 93/17322 A1 | 9/1993 |
| 6,617,107 | B1 | 9/2003 | Dean | WO | WO 96/12171 | 10/1995 |
| 6,618,679 | B2 | 9/2003 | Loehrlein et al. | WO | WO 96/31764 | 10/1996 |
| 6,642,018 | B1 | 11/2003 | Koller et al. | WO | WO 99/05504 | 7/1998 |
| 6,667,830 | B1 | 12/2003 | Iketaki et al. | WO | WO 98/34094 | 8/1998 |
| 6,671,044 | B2 | 12/2003 | Ortyn et al. | WO | WO 98/48259 | 10/1998 |
| 6,673,095 | B2 | 1/2004 | Nordquist | WO | WO 99/33956 | 7/1999 |
| 6,782,768 | B2 | 8/2004 | Buchanan et al. | WO | WO 99/38883 | 8/1999 |
| 6,819,411 | B1 | 11/2004 | Sharpe et al. | WO | WO 99/42810 | 8/1999 |
| 7,094,527 | B2 | 8/2006 | Seidel et al. | WO | WO 99/44037 A1 | 9/1999 |
| 7,195,920 | B2 * | 3/2007 | Seidel et al. .................... 436/63 | WO | WO 00/06193 | 2/2000 |
| 2002/0113965 | A1 | 8/2002 | Roche et al. | WO | WO 01/37655 A1 | 5/2001 |
| 2002/0119558 | A1 | 8/2002 | Seidel et al. | WO | WO 01/40765 A2 | 6/2001 |
| 2002/0141902 | A1 | 10/2002 | Ozasa | | | |

| | | |
|---|---|---|
| WO | WO 01/40765 A3 | 6/2001 |
| WO | WO 01/51612 A1 | 7/2001 |
| WO | WO 01/85913 A2 | 11/2001 |
| WO | WO 01/85913 A3 | 11/2001 |
| WO | WO 01/90295 A1 | 11/2001 |
| WO | WO 01/95815 A1 | 12/2001 |
| WO | WO 02/19943 A1 | 3/2002 |
| WO | WO 02/28311 A2 | 4/2002 |
| WO | WO 02/41906 A2 | 5/2002 |
| WO | WO 02/43486 A1 | 6/2002 |
| WO | WO 02/43574 A2 | 6/2002 |
| WO | WO 2004/009237 A1 | 1/2004 |
| WO | WO 2004/012837 A1 | 2/2004 |
| WO | WO 2004/017041 A1 | 2/2004 |
| WO | WO 2004/024227 A2 | 3/2004 |
| WO | WO 2004/059282 A2 | 7/2004 |
| WO | WO 2004/003697 A2 | 10/2004 |
| WO | WO 2004/087177 A1 | 10/2004 |
| WO | WO 2004/088283 A2 | 10/2004 |
| WO | WO 2004/104178 A1 | 12/2004 |
| WO | WO 2004/104178 A3 | 12/2004 |
| WO | WO 2005/094852 A2 | 10/2005 |
| WO | WO 2005/095590 A2 | 10/2005 |
| WO | WO 2005/095960 A1 | 10/2005 |
| WO | WO 2006012597 A2 | 2/2006 |

OTHER PUBLICATIONS

Braun et al. Crybiology. 1995. 32: 487-492.*
European Regional Patent Application No. 99 937 611.4; Partial Search Report dated May 25, 2004.
European Regional Patent Application No. 99 937 611.4; Examination Report dated Sep. 27, 2004.
European Regional Patent Application No. 99 937 611.4; Examination Report dated Aug. 11, 2005.
New Zealand Patent Application No. 509434; Examination Report dated Sep. 3, 2003.
New Zealand Patent Application No. 509434; Examination Report dated Apr. 16, 2004.
New Zealand Patent Application No. 509434; Letters patent dated Jul. 29, 2004.
New Zealand Patent Application No. 509434; Examination Report dated Jul. 19, 2005.
New Zealand Patent Application No. 509434; Letters patent dated Jul. 29, 2004.
New Zealand Patent Application No. 527659; Examination Report dated Aug. 25, 2003.
New Zealand Patent Application No. 527659; Examination Report dated Jul. 22, 2005.
New Zealand Patent Application No. 527659; Examination Report dated Jul. 19, 2005.
New Zealand Patent Application No. 527659; Examination Report dated. Sep. 21, 2005.
New Zealand Patent Application No. 527659; Examination Report dated Aug. 22, 2005.
New Zealand Patent Application No. 540993; Examination Report dated Jul. 5, 2005.
Seidel, G. E. Jr., "Fertility of Bulls on the Edge of the Dose-Response Curve for Numbers of Sperm per Inseminate"; Proceedings of the 17th Technical comference on Artificial Insemination & Reproduction, 1998.
Hollinshead, F.K. et al. "In vitro and in vivo assessment of functional capacity of flow cytometrically sorted ram spermatozoa after freezing and thawing." Reprod. Fertil. And Develop. 2003. vol. 15, pp. 351-359.
Hollinshead F. K. et al. "Production of lambs of predetermined sex after the insemination of ewes with low numbers of frozen-thawed sorted X- or Y- Chromosome-bearing spermatozoa", Reprod. Fertil. And Develop. 2002, vol. 14, pp. 503-508.
Hollinshead F. K. et al. "Sex-Sorting and Re-cryopreservation of Frozen-Thawed Ram Sperm for in Vitro Embryo Production" Theriogenology , vol. 59. (2003) pp. 209.

Dhali et al. Vitrification of Buffalo (Bubalus Bubalis)Oocytes, Embryo Theriogenology vol. 53, pp. 1295-1303 (2000).
Borini et al. Cryopreservation of Mature Oocytes: The use of a trypsin inhibitor enhances fertilization and obtained embryos rates, Fertil. Steril. (1997), vol. 68 (Suppl.).
Hamamatsu Photonics K.K. Electronic Tube Center, Photomultiplier Tubes, Brochure Dec. 1997.
Johnson, L. A., et al. The Beltsville Sperm Sexing Technology: High-speed sperm sorting gives improved sperm output for In Vitro fertiliation and AI, Journal of Animal Science,vol. 77, Suppl 2/J, Dairy Sci. vol. 82, Suppl. Feb. 1999 pp. 213-220.
Peters D., The LLNL high-speed sorter: Design features,operational characteristics, and bioloical utility, Cyometry, 6:290-301 (1985).
Rens W., et al Slit-scan flow cytometry for consistent high resdolution DNA analysis of X- and Y- chromosome bearing sperm, Cytometry 25:191-199 (1996).
van Munster, E. B. Interferometry in flor to sort unstained X- and Y-Chromosome-Bearing Bull Spermatozoa, Cytometry 47:192-199 (2002).
Scmid, R. L., et al. Effects of follicular fluid or progesterone on in vitro maturation of equine oocytes before intracytoplasmic sperm injection with non-sorted and sex-sorted spermatozoa, Journal of Reproduction and Fertility 56:519-525, 2000.
Brink, Z et al. A reliable procedure for superovulating cattle to obtain zygotes and early emryos for microinjection, Theriogenology vol. 41, p. 168, (1994).
Spectra-Physics, The Solid State Laser Company, Vanguard 350-HMD 355, User's Manual, Dec. 2002.
Photon, Inc. Light MeasuringSolutions, NanoScan for High-powered beam Applications, 2005.
Fluorescense Lifetime Systems, www.picoquant.com, Jan. 28, 2005 pp. 2.
NCI ETI Branch, Flow CytometryCore Laboratory, http://home.ncifcrf.gov/ccr/flowcore/ndyag.htm, pp. 5, May 11, 2004.
NCI ETI Branch, Flow CytometryCore Laboratory, http://home.ncifcrf.gov/ccr/flowcore/lsrll.htm, pp. 14, May 11, 2004.
Saacke,R.G., Can Spermatozoa with abnormal heads gain access to the ovum in artificially inseminated super- and single-ovulating cattle?, Theriogenology 50:117-128. 1998.
Hawk, H.W., Gamete Transport in the Superovulated Cow. Theriogenology: Jan. 1998 vol. 29 No. 1 pp. 125-142.
Blecher, S.R., et al. A new approach to immunological sexing of sperm, Theriogenology, 59, pp. 1309-1321, 1999 Vol.
Wheeler, M. B., et al. Application of sexed semen technology to in vitro embryo production in cattle, Theriogenology, vol. 65 (2006) 219-227.
Garverick, H. A., et al. mRNA and protein expression of P450 aromatase (AROM) and estrigen receptors (ER) α and β during early development of bovine fetal ovaries; The society for the study of reproduction 38th annual meeting Jul. 24-27, 2005; Abstract only.
Bodmer, M., et al., Fertility in heifers and cows after low does insemination with sex-sorted and non-sorted sperm under field conditions; Theriogenology, vol. 64, (2005) 1647-1655.
Schenk J. L., et al. Embryo production from superovulated cattle following insemination of sexed sperm, Theriogenology, 65 (2006) 299-307.
Garner, D. L., Flow cytometric sexing of mammalian sperm, Theriogenology, (2006) pp. 15.
Habermann F. A., et al., Validation of sperm sexing in the cattle (*Bos taurus*) by dual colour flourescence in situ hybridization; J Anim Breed Genet. Apr. 2005; 122 Suppl 1:22-7 (Abstract only).
Johnson, L. A., Sexing mammalian sperm for production of offspring: the state-of-the-art; Animal Reproduction Science; 60-61 (2000) pp. 93-107.
Pursel, et al, "Effect of Orvus ES Paste on Acrosome Morphology, Motility and Fertilizing Capacity of Frozen-Thawed Boar Sperm," Journal of Animal Science, 47:1:198-202 (1978).
Seidel, G.E. Jr., et al., Methods of Ovum Recovery and Factors Affecting Fertilization of Superovulated Bovine Ova, Control of Reproduction in the Cow, Sneenan ed., 1978, pp. 268-280.
Hawk, H. W. et al., Effect of Unilateral Cornual Insemination upon Fertilization Rate in Superovulating and Single-Ovulating Cattle, Journal of Animal Sciences, 1986 vol. 63, pp. 551-560.

Andersson, M. et al., Pregnancy Rates in Lactating Holstein-Greisian Cows after Artificial Insemination with Sexed Sperm. Reprod. Dom. Anim 41, 95-97, 2006.

Morton, K. M., et al., In vitro and in vivo survival of bisected sheep embryos derived from frozen-thawed unsorted, and frozen-thawed sex-sorted and refrozen-thawed ram spermatozoa; Theriogenology, 65 (2006) 1333-1345.

Wilson, R. D., et al., In vitro production of bovine embryos using sex-sorted sperm, Theriogenology, 65 (2006) 1007-1015.

Johnson, L.A., et al, 1996 Gender preselection in mammals. XX Beltsville Symposium in Agricultural Research Technolgy's Role in the Genetic Improvement of Farm Animals. pp. 151-164, Amer. Soc. Anim. Sci. IL, USA.

Smorag, Z., et al., Cattle Sex Regulation by Separation of X and Y Spermatozoa—Preliminary Results of Field Experiment in Poland, Reproduction, Fertility and Development 17(2) 306-306; Jan. 1, 2005.

Crichton, E., et al. (Abstract) Artificial Insemination of Lactating Holstein Cows with Sexed Sperm, Reproduction, Fertility and Development 18(2) 281-281, Dec. 14, 2005.

Lindsey, A.C., et al. Hysteroscopic insemination of low numbers of flow sorted fresh and frozen/thawed stallion spermatozoa, Equine Vet J. Mar. 2002;34(2):106-7.

Drobnis, E. Z, Cold shock damage is due to lipid phase transitions in cell membranes : a demonstration using sperm as a model, Journal of experimental zoology (J. exp. zool.) 1993, vol. 265, No. 4, pp. 432-437 (22 ref.).

Hagele, W.C., et al., Effect of Separating Bull Semen into X and Y Chromosome-bearing Fractions on the Sex Ratio of Resulting Embryos; Cran J. Comp. Med, 1984: 48:294-298.

Suh, T.K, et al., Pressure during flow sorting of bull sperm affects post-thaw motility characteristics; Theriogenology vol. 59, No. 1, Jan. 2003 p. 516.

Rath, D, et al., In Vitro Production of Sexed Embryos for Gender Preselection: High-speed sorting of X-Chromosome-Bearing Sperm to Produce Pigs After Embryo Transfer, J. Anim. Sci. 1999, 77:3346-3352.

Auchtung, T.L., et al., Effects of Photoperiod During the Dry Period on Prolactin, Prolactin Receptor, and Milk Production of Dairy Cows; Journal of Dairy Sci. 88: 121-127; American Dairy Sci. Assoc., 2005.

Bailey, Tom and Currin, John Milk Production Evaluation In First Lactation Heifers; 1999 Virginia Cooperation Extension/Dairy Science Publication 404-285.

Belloin, J.C., Milk and Dairy products: prduction and processing costs Food and Agriculture Organization of United Nations Rome 1988 FAO; web page where found: www.fao.org/docrep/003/x6931e/x6931E00.htm.

Kume, Shin-ichi; Dept of Animal Nutrition National Institute of Animal Industry Tsukuba 305, Japan The Dairy Industry $In Asia B. Japan; www.agnet.org/library/article/eb384b.html, Oct. 1, 1994.

Crichton,E.; Huffman,S.;McSweeney,K.;and Schenk, J. 347 Artificial Insemination of Lactating Holstein Cows with sexed sperm: Abstract CSORP Publishing—Reproduction, Fertility and Development www.publish.csiro.au/nid/44/paper/RDv18n2Ab347.htm, Dec. 14, 2005.

Lopez, H.,Caraviello, D.Z., Satter, L.D. ,Fricke, P.M. and Wiltbank, M.C.; Relationship Between Level of Milk Production and Multiple Ovulation in Lactating Dairy Cows Journal of Dairy Sci. 88:2783-2793; American Dairy Science Association, 2005.

Milk Production Released Jul. 18, 2006, by the National Agricultural Statistics Service (NASS), Agri. Stats. Board, US Dept of Agri.

DeVries, A. Economic Value of Pregnancy in Dairy Cattle Journal of Dairy Sci. 89:3876-3885/American Dairy Sci. Assoc. 2006.

Garner, D.L. et al., Viability Assessment of Mammalian Sperm Using SYBR-14 and Propidium Lodide, 1996, Biology of Reporduction, vol. 53, pp. 276-284.

Salisbury, G.W. et al., Substrate-Free Epididymal-Like Bovine Spermatozoa, J Reporod Fertil, 1963, vol. 6, pp. 351-359.

Amann, R.P. et al, "Prospects For Sexing Mammalian Sperm," Colorado Associated University Press, Animal Reproduction Laboratory College of Veterinary Medicine and Biomedical Sciences, Colorado State University, Fort Collins, CO, 80523, 1982, Table of contents only.

Amoah, E.A. and Gelaye, S. 1996. Biotechnological advances in goat reproduction. J. Anim. Sci. 75(2):578-585.

Anderson, V.K., Aamdal, J. and Fougner, J.A. 1973. Intrauterine und tiefzervikale Insemination mit Gefriersperma bein Schat. Zuchthygiene. 8:113-118.

Baker, R.D., Dziuk, P.J. and Norton, H.W. 1968. Effect of volume of semen, number of sperm and drugs on transport of sperm in artificially inseminated gilts. J. Anim. Sci. 27:88-93.

Becker, S.E. and Johnson, A.L. 1992. Effects of gonadotropin releasing hormone infused in a pulsatite or continuous fashion on serum gonadotropin concentrations and ovulation in the mare. J. Anim. Sci. 70:1208-1215.

Bedford, S .J. and Hinrichs, K. 1994. The effect of insemination volume on pregnancy rates of pony mares. Theriogenology 42:571-578.

Berger, G.S. 1987. Intratubal insemination. Fert. Steril. 48:328-330.

Blanchard, T. and Dickson, V., "Stallion Management", The Veterinary Clinics of North America, Equine Practice, vol. 8, No. 1, Apr. 1992, pp. 207-218.

Bracher, V. and Allen, W.R., "Videoendoscopic Examination of the Mare's Uterus: Findings in Normal Fertile Mares", Equine Veterinary Journal, vol. 24 (1992), pp. 274-278.

Braselton, W.E. and McShan, W.H. 1970. Purification and properties of follicle stimulating and luteinizing hormones from horse pituitary glands. Arch. Biochem. Biophys. 139:45-48.

Bristol, S.P. 1982. Breeding behavior of a stallion at pasture with 20 mares in synchronized oestrus. J. Reprod. Fert. Suppl. 32:71.

Burwash, L.D., Pickett, B.W., Voss, J.L. and Back, D.G. 1974. Relatioship of duration of estms to pregnancy rate in normally cycling, non-lactating mares. J.A.V.M.A. 165:714-716.

Caslick, E.A., "The Vulva and the Vulvo-vaginal Orifice and its Relation to Genital Health of the Thoroughbred Mare", Cornell Veterinarian, vol. 27, 1937, pp. 178-187.

Catt, et al., "Assesment of Ram and Boar Spermatozoa During Cell-Sorting by Flow Cytometry", Reproduction Dom Animal, vol. 32, pp. 251-258 (1997).

Chung,Y.G., Schenk, J.L., Herickhoff, L.A. and Seidel, G.E. Jr. 1998. Artificial insemination of superovulated heifers with 600,000 sexed sperm. J Anim. Sci. Suppl. 1. 836:215. abstr.

Clement, F., Vincent, P., Mahla, R., Meriaux, J.C. and Palmer, E. 1998. Which insemination fertilizes when several successive inseminations are performed before ovulation. $7^{th}$ Int. Symp. Eq. Repro. 151. abstr.

Cran, D.C., McKelvey, W.A.C., King, M.E., Dolman, D.F., McEvoy, T.G., Broadbent, P.J. and Robinson, J.J. 1997. Production of lambs by low dose intrauterine insemination with flow cytometrically sorted and unsorted semen. Theriogenology. 47(1):267. abstr.

Cran, D.G., et al, "Production of Lambs by Low Dose Intrauterine Insemination with Flow Cytometrically Sorted and Unsorted Semen", Theriogenology, vol. 47, pp. 267, (Abstract),(1997).

Cran, D.G., Johnson, L.A., Miller, N.G., Cochrane, D. and Polge, C. 1993. Production of bovine calv.es following separation of X- and Y-chromosome bearing sperm and in vitro fertilisation. Vet. Rec. 132:40-41.

Curran, S. 1998. In: Equine Diagnostic Ultrasonography. Fetal gender determination. Rantanen & McKinnon. $1^{st}$ Ed. Williams and Wilkins. pp. 165-169.

Day, B.N., Abeydeera, L.R., Johnson, L.A., Welch, G.R., Wang, W.H., Cantley, T.C. and Rieke, A. 1998. Birth of piglets preselected for gender following in vitro fertilization of in vitro matured pig oocytes by X and Y bearing spermatozoa sorted by high speed flow cytometry. Theriogenology. 49(1):360. abstr.

Dean, P.N., Pinkel, D. and Mendelsob. n, M.L. 1978. Hydrodynamic orientation of spermatozoa heads for flow cytometry. Biophys. J. 23:7-13.

Demick, D.S., Voss, J.L. and Pickett, B.W. 1976. Effect of cooling, storage, glycerization and spermatozoal numbers on equine fertility. J. Anim. Sci. 43:633-637.

DenDaas, J.H.G., De Jong, G., Lansbergen, L.M.T.E. and Van Wagtendonk-De Leeuw, A.M. 1998. The relationship between the number of spermatozoa inseminated and the reproductive efficiency of dairy bulls. J Dairy Sci. 81: 1714-1723.

Donaldson, L. E., "Effect of Insemination Regimen on Embryo Production in Superovulated Cows", The Veterinary Record, Jul. 13, 1985, pp. 35-37.

Donoghue, A.M., Byers, A.P., Johnston, L.A., Armstrong, D.L. and Wildt, D.E. 1996. Timing of ovulation after gonadotropin induction and its importance to successful intrauterine insemination in the tiger (*Panthera tigris*). J. Reprod. Fert. 107:53-58.

Douglas, R.H., Nuti, L. and Ginther, O.J. 1974. Induction of ovulation and multiple ovulation on seasonally-anovulatory mares with equine pituitary fractions. Theriogenology. 2(6): 133-142.

Duchamp, G., Bour, B., Combarnous, Y. and Palmer, E. 1987. Alternative solutions to hCG induction of ovulation in the mare. J. Reprod. Fert. Suppl. 35:221-228.

Evans, M.J. and Irvine, C.H.G. 1977. Induction of follicular development, maturation and ovulation by gonadotropin releasing hormone administration to acyclic mares. Bio. Reprod. 16:452-462.

Fitzgerald, B.P., Peterson, K.D. and Silvia, P.J. 1993. Effect of constant administration of a gonadotropin-releasing hormone agonist on reproductive activity in mares: Preliminary evidence on suppression of ovulation during the breeding season. Am. J. Vet. Res. 54:1746-1751.

Fluharty, F.L., et al., "Effects of Age at Weaning and Diet on Growth of Calves", Ohio Agri. Res. and Dev. Circular, 1996, 156: 29.

Fugger, E.F., "Clinical Experience with Flow Cytometric Separation of Human X- and Y- Chromosome Bearing Sperm", Theriogenology, vol. 52, pp. 1435-1440 (1999).

Fulwyler, M.J. 1965. Electronic separation of biological cells by volume. Science. 150:910.

Fulwyler, M.J. 1977. Hydrodynamic orientation of cells. J Histochem. Cytochem. 25:781-783.

Garner, D.L., Gledhill, B.L., Pinkel, D., Lake, S., Stephenson, D., Van Dilla, M.A. and Johnson, L.A. 1983. Quanti~cation of the X and Y chromosome-bearing spermatozoa of domestic animals by flow cytometry. Biol. Reprod. 28:312-321.

Ginther, O.J. 1971. Some factors which alter estrus cycle in mares. J. Anim. Sci. 33:1158. abstr.

Ginther, O.J. 1983. Sexual behavior following introduction of a stallion into a group of mares. Theriogenology. 19:877.

Ginther, O.J. 1992. In: *Reproductive Biology of the Mare*. (2$^{nd}$ Ed.) Equiservices, Cross Plains, WI.

Guillou, F. and Combarnous, Y. 1983. Purification of equine gonadotropins and comparative study of their acid-dissociation and receptor-binding specificity. Biochem. Biophys. Acta. 755:229-236.

Gurnsey, M.P., and Johnson, L.A., "Recent improvements in efficiency of flow cytometric sorting of X and Y- chromosome bering sperm of domestic animals: a review", 1998, New Zealand Society of Animal Protection, three pages.

Gourley, D.D. and Riese, R.L. 1990. Laparoscopic artificial insemination in sheep. Vet. Clin. N. Amer: Food Anim. Prac. 6(3):615-633.

Harrison, L.A., Squires, E.L. and McKinnon, A.O. 1991. Comparison of hCG, buserelin and luprostiol for induction of ovulation in cycling mares. Eq. Vet. Sci. 3:163-166.

Hawk, H. "Fertilization Rates in superolvulating cows after deposition of semen on the infundidlum near the uterotubal junction or after insemination with high numbers of sperm.", XP-002103478, Biosis, 1988, one page.

Hofferer, S., Lecompte, F., Magallon, T., Palmer, E. and Combarnous, Y. 1993. Induction of ovulation and superovulation in mares using equine LH and FSH separated by hydrophobic interaction chromatography. J. Reprod. Fert. 98:597-602.

Holtan, D.W., Douglas, R.H. and Ginther, O.J. 1977. Estrus, ovulation and conception following synchronization with progesterone, prostaglandin F2 ct and human chorionic gonadotropin in pony mares. J. Anim. Sci. 44:431-437.

Householder, D.D., Pickett, B.W., Voss, J.L. and Olar, T.T. 1981. Effect of extender number of spermatozoa and hCG on equine fertility. J. Equine Vet. Sci. 1:9-13.

Howard, J.G., Bush, M., Morton, C., Morton, F., Wentzel, K. and Wildt, D.E. 1991. Comparative semen cryopreservation in ferrets (Mustela putorious furo) and pregnancies after laparoscopic intrauterine insemination with frozen-thawed spermatozoa. J. Reprod. Fert. 92:109-118.

Howard, J.G., Roth, T.L., Byers, A.P., Swanson, W.F. and Wildt, D.E. 1997. Sensitivity to exogenous gonadotropins for ovulation and laparoscopic artificial insemination in the theetab and clouded leopard. Biol. Reprod. 56:1059-1068.

Hyland, J.H., Ainsworth, C.G.V. and Langsford, D.A. 1988. Gonadotropin-releasing hormone (GnRH) delivered by continuous infusion induces fertile estrus in mares during seasonal acyclicity. Proc. Amer. Assoc. Eq. Prac. 181-190.

Jafar, et al., "Sex Selection in Mammals: A Review", Theriogenology, vol. 46, pp. 191-200 (1996).

Jasko, D.J., Martin, J.M. and Squires, E.L. 1992. Effect of volume and concentration of spermatozoa on embryo recovery in mares. Theriogenology. 37:1233-1239.

Johnson, A.L. 1986. Pulsatile release of gonadotropin releasing hormone advances ovulation in cycling mares. B iol. Reprod. 35:1123*1130.

Johnson, A.L. and Becker, S.E. 1988. Use of gonadotropin-releasing hormone (GnRH) treatment to induce multiple ovulations in the anestrous mare. Eq. Vet. Sci. 8:130-134.

Johnson, L.A. and Pinkel, D. 1986. Modification of a laser based flow cytometer for high resolution DNA analysis of mammalian spermatozoa. Cytometry. 7:268-273.

Johnson, L.A., et al, "Sex Preselection in Swine: Flow Cytometric Sorting of X- and Y- Chromosome Bearing Sperm to Produce Offspring", Boar Semen Preservation IV, 2000, pp. 107-114.

Johnson, L..A., "Advances in Gender Preselection in Swine" Journal of Reproduction and Fertility Supplement, vol. 52, pp. 255-266 (1997).

Johnson, L..A., "Sex Preselection in Swine: Altered Sex Ratios in Offspring Following Surgical Insemination of Flow Sorted X- and Y- Bearing Sperm", Reproduction in Domestic Animals, vol. 26, pp. 309-314 (1991).

Johnson, L.A. 1992. Gender preselection in domestic animals using flow cytometrically sorted sperm. J Anim. Sci. Suppl 1.70:8-18.

Johnson, L.A. 1994. Isolation of X- and Y-bearing spermatozoa for sex preselection. In: Oxford Reviews of Reproductive Biology. Ed. HH Charlton. Oxford University Press. 303-326.

Johnson, L.A. 1997. Advances in gender preselection in swine. J Reprod. Fert. Suppl. 52:255-266.

Johnson, L.A., and Pinkel, D., "Modification of a Laser-Based flow Cytometer for High-Resolution DNA Analysis of Mammalian Spermatozoa", Cytometry 7, 1986, pp. 268-273.

Johnson, L.A. and Welch, G.R., "Sex Preselection: High-speed flow cytometric sorting of X and Y sperm for maximum efficiency", Theriogenology, vol. 52, (1999), pp. 1323-1341.

Johnson, L.A., et al., "Sex Preselection in Rabbits: Live Births from X and Y Sperm Separated by DNA and Cell Sorting", Execptional Paper-Rapid Publication, XP-002103476, Biology of Reproduction 41, 199-203, 1989, pp. 199-203.

Johnson, L.A., Flook, J.P., Look, M.V. and Pinkel, D. 1987b. Flow sorting of X and Y chromosome bearing spermatozoa into two populations. Garn. Res. 16:203-212.

Johnson, L.A., Welch, G.R., Rens, W. and Dobrinsky, J.R. 1998. Enhanced flow cytometric sorting of manunalian X and Y sperm: high speed sorting and orienting No. 77.1e for artificial insemination. Theriogenology. 49(1):361. abstr.

Johnson, L.A., et al., 1994. Improved flow sorting resolution of X- and Y- chromosome bering viable sperm separation using dual staining and dead cell gating. Cytometry 17 (suppl 7):83.

Johnson, L..A., "Sex Preselection in Swine: Altered Sex Ratios in Offspring Following Surgical Insemination of Flow Sorted X- and Y- Bearing Sperm", Reproduction in Domestic Animals, vol. 26, pp. 309-314 (1991).

Johnson L.A., et al., 1987. Flow cytometry of X- and Y- chromosome bearing sperm for DNA using an improved preparation method and staining with Hoechst 333-42. Garnete Research 17: 203-212.

Johnson, "Gender preselection in Mammals: An overview", Deutsch. Tierarztl. Wschr, vol. 103, pp. 288-291 (1996).

Kachel, V., et al., "Uniform Lateral Orientation, Cused by Flow Forces, of Flat Particles in Flow-Through Systems", The Journal of Histochemistry and Cytochemistry, 1997, vol. 25, No. 7, pp. 774-780.

Kilicarslan, M.R., Horoz, H., Senunver, S.C., Konuk, S.C., Tek, C. and Carioglu, B. 1996. Effect of GrnRH and hCG on ovulation and pregnancy in mares. Vet. Rec. 139:119-120.

Lapin, D.R. and Ginther, O.J. 1977. Induction of ovulation and multiple ovulations in seasonally anovulatory and ovulatory mares with an equine pituitary extract. J. Anim. Sci. 44:834-842.

Lawrenz, R. 1985. Preliminary results of non-surgical intrauterine insemination of sheep with thawed frozen semen. J S Afr. Vet. Assoc. 56(2):61-63.

Lindsey, A., et al., "Hysteroscopic Insemination of Mares with Nonfrozen Low-dose Unsexed or Sex-sorted Spermatozoa", currently unpublished, pp. 1-15.

Long, C.R., Rath, D., Welch, G.R., Schreier, L.L., Dobrinsky, J.R. and Johnson, L.A. *1998*. Theriogenology. 49(1):363. abstr.

Macmillan, K.L. and Day, A.M., "Prostaglandin F2a : A Fertility Drug In Dairy Cattle?", Animal Research Station, Private Bag, Hamilton, New Zealand, Theriogenology, vol. 18 No. 3, pp. 245-253 (1982).

Matsuda, Y. and Tobari, I. 1988. Chromosomal analysis in mouse eggs fertilized in vitro with sperm exposed to ultraviolet light (UV) and methyl and ethyl methanesulfonate (MMS and EMS). Mutat. Res. 198:131-144.

Maxwell, W.M.C., Evans, G., Rhodes, S.L., Hillard, M.A. and Bindon, B.M. 1993. Fertility of Superovulated Ewes after Intrauterine or Oviductal Insemination with Low Numbers of Fresh or Frozen-Thawed Spermatozoa. Reprod. Fertil. Dev. 5:57-63.

McDonald, L.E. 1988. Hormones of the pituitary gland. In: Veterinary Pharmacology and Therapeutics. $6^{th}$ ed. Edited by N.H. Booth and L.E. McDonald. Ames, Iowa State Univ. Press. pp. 590.

McKeuna, T., Lenz, R.W., Fenton, S.E. and Ax, R.L. 1990. Nonreturn rates of dairy cattle following uterine body or cornual insemination. J. Dairy Sci. 73:1179-1783.

McKinnon, A. and Voss, J., "Equine Reproduction", Lea & Febiger, Philadelphia, 1993, pp. 291, 299-302, 345-348, 739-797.

McKinnon, A. et al, 1993. Predictable ovulation in mares treated with an implant of the GnRH analogue deslorelin. Eq. Vet. J. 25:321-323.

McKinnon, A.O. et al, 1996. Repeated use of a GnRH analogue deslorelin (Ovuplant) for hastening ovulation in the transitional mare. Eq. Vet. J. 29:153-155.

McNutt, T.L. and Johnson, L.A. 1996. Flow cytometric sorting of sperm: influence on fertilization and embryo/fetal development in the rabbit. Mol. Reprod. Dev. 43:261-267.

Meinert, C., et al., "Advancing the time of ovulation in the mare with a short-term inplant releasing the GnRH analogue deslorelin", Equine Veterinary Journal, 25, 1993, pp. 65-68.

Meyers, P.J., Bowman, T., Blodgett, G., Conboy, H.S., Gimenez, T., Reid, M.P., Taylor, B.C., Thayer, J., Jochle, W. and Trigg, T.E. 1997. Use of the GnRH analogue, deslorelin acetate, in a slow release implant to accelerate ovulation in oestrous mares. Vet. Rec. 140:249-252.

Michel, T.H., Rossdale, P.D. and Cash, R.S.G. 1986. Efficacy of human chorionic gonadotrophin and gonadatrophin releasing hormone for hastening ovulation in Thoroughbred mares. Eq. Vet. J. 6:438-442.

Michaels, Charles, "Beef A.I. Facilities that work", Proc. Fifth N.A. A.B Tech. Conf. A.I. Reprod. Columbia, MO. pp. 20-22.

Molinia, F.C., Gibson, R.J., Brown, A.M., Glazier, A.M. and Rodger, J.C. 1998. Successful fertilization after superovulation and laparoscopic intrauterine insemination of the brushtail possum, *Trichosurus vulpecula*, and tammar wallaby, *Macropus eugenii*. J.Reprod. Fert. 112:9-17.

Morcom, C.B. and Dukelow, W.R. 1980. A research technique for the oviductal insemination of pigs using laparoscopy. Lab. Anim. Sci. 1030-1031.

Morris, L.H., et al., "Hysteroscopic insemination of small numbers of spermatozoa at the uterotubal junction of preovulatory mares", Journal of Reproduction and Fertility, vol. 118, pp. 95-100 (2000).

Mullet, W. and Gautier, F. 1975. Interactions of heteroaromatic compounds with nucleic acids. Euro. J Biochem. 54:358.

Nowshari, et al., "Superovulation of Goats with Purified pFSH Supplemented with Defined Amounts of pLH", Theriogenology, vol. 43, pp. 797-802 (1995).

Pace, M.M. and Sullivan, J.J. 1975. Effect of timing of insemination, numbers of spermatozoa and extender components on pregnancy rates in mares inseminated with frozen stallion semen. J Reprod. Fert. Suppl. 23:115-121.

Parrish, J.J., et al., "Capacitation of bovine sperm by heparin", Biology of Reproduction, vol. 38, pp. 1171-1180 (1988).

Peippo, J., et al., "Sex diagnosis of equine preimplantation embryos using the polymerase chain reaction", Theriogenology, vol. 44 619-627 (1995).

Perry, E.J. 1968. Historical Background In: *The Artificial ]nsemination of Farm Animals*. $4^{th}$ ed. Edited by E.J. Perry. New Brunswick, Rutgers University Press, pp. 3-12.

Petersen, G.A., et al, "Cow and Calf Performance and Economic Considerations of Early Weaning of Fall-Born Beef Claves", J. Anim. Sci., 1987, 64:15, pp. 15-22.

Pickett, B.W., and Shiner, K.A., "Recent developments in artificial insemination in horses", Livestock Production Science, 40, 1994, pp. 31-36.

Pickett, B.W., Burwash, L.D., Voss, J.L. and Back, D.G. 1975b. Effect of seminal extenders on equine fertility. J. Anim. Sci. 40:1136-1143.

Pinkel, D., et al, "Flow Cytometric Determination of the Proportions of X- andY- Chromosome-Bearing Sperm in Samples of Purportedly Separated Bull Sperm", Journal of Animal Science, vol. 60, No. 5, 1985, pp. 1303-1307.

Rath, D., et al., "Low Dose Insemination Technique in the Pig", Boar Semen Preservation IV, 2000, pp. 1 15-118.

Rath, D., et al., "Production of Piglets Preselected for Sex Following in Vitro Fertilization with X and Y Chromosome-Bearing Spermatozoa Sorted by Flow Cytometry", Theriogenology, 47, 1997, pp. 795-800.

Reiling, B.A., et al., "Effect of Prenatal Androgenization on Preformance, Location, and Carcass and Sensory Traits on Heifers in Single Calf Heifer System", J. Anim. Sci., 1995, 73: 986, pp. 986-992.

Rens, W., et al., "Improved Flow Cytometric Sorting of X- and Y-Chromosome Bearing Sperm: Substantial Increase in Yield of Sexed Semen", Molecular Reproduction and Development, 1999, pp. 50-56.

Rens, W., et al., "A Novel Nozzle for More Efficient Sperm Orientation to Improve Sorting Efficiency of X and Y Chromosome-Bearing Sperm", Technical Notes, Cytometry 33, 1998, pp. 476-481.

Ritar, A. and Ball, A. 1991. Fertility of young cashmere goats after laparoscopic insemination. J. Agr. Sci. 117:271-273.

Roberts, J.R. 1971. In: *Veterinary Obstetrics and Genital Diseases*. Ithaca, New York. pp. 740-749.

Roth, T.L., Wolfe, B.A., Long, J.A., Howard, J. and Wildt, D.E. 1997. Effects of equine chorionic gonadotropin, human chorionic gonadotropin, and laparoscopic artificial insemination on embryo, endocrine, and luteal characteristics in the domestic cat. Bio Reprod. 57:165-171.

Rowley, H-S., Squires, E.L. and Pickett, B.W. 1990. Effect of insemination volume on embryo recover}' in mares. J. Equine Vet. Sci. 10:298-300.

Salamon, S. 1976. *Artificial Insemination of Sheep*. Chippendale, New South Whales. Publicity Press. p. 83-84.

Salisbury, G.W. and VanDemark, N.L. 1961. *Physiology of Reproduction and Artificial Insemination of Cattle*. San Francisco: Freeman and Company.

SAS, SAS/STAT ® User's Guide (Release 6.03), SAS Inst. Inc., Cary, NC., 1988. 3 pages.

Schenk, J.L. and Seidel, Jr., G.E., "Imminent Commercialization of Sexed Bovine", Proceedings, The Range Beef Cow Symposium XVL, 1999, pp. 89-96.

Schenk, J.L., "Cryopreservation of flow-sorted bovine spermatozoa", Theriogenology, vol. 52, 1375-1391 (1999).

Schmid R.L., et al, "Fertilization with Sexed Equine Spermatozoa Using Intracytoplasmic Sperm Injection and Oviductal Insemination", 7th International Symposium On Equine Reproduction, pp. 139 (Abstract) (1998).

Seidel, Jr., G.E.et al, "Insemination Of Heifers With Very Low Numbers Of Frozen Spermatozoa", Colorado State University (1996).

Seidel, Jr., G. E., et al, "Insemination of Holstein Heifers With Very Low Numbers Of Unfrozen Spermatozoa", Colorado State University, Atlantic Breeders Cooperative, (1995).

Seidel, Jr., G. E., "Artificial Insemination With X-and Y-Bearing Bovine Sperm", Animal Reproduction and Biotechnology Laboratory, Colorado State University, (1996).

Seidel, G.E. Jr, et al., "Insemination of Heifers with Sexed Sperm", Theriogenology, vol. 52, pp. 1407-1421 (1999).

Seidel, G.E. Jr, et al., "Artificial Insemination of Heifers with Cooled, Unfrozen Sexed Semen", Theriogenology, vol. 49 pp. 365 (Abstract) (1998).

Seidel, G.E. Jr., et al, 1997. Uterine insemination of heifers with very low numbers of nonfrozen and sexed spermatozoa. Theriogenology. 48:1255-1264.

Senger, P.L., Becker, W.C., Davidge, S.T., Hillers, J.K. and Reeves, J.J. 1988. Influence of cornual insemination on conception rates in dairy cattle. J Anim. Sci. 66:3010-3016.

Shelton, J.N. and Moore, N.W. 1967. The response of the ewe tot pregnant mare gonadotropin and to horse anterior pituitary extract. J. Reprod. Fert. 14:175-177.

Squires, E., "Simultaneous Analysis of Multiple Sperm Attributes by Flow Cytometry", Diagnostic Techniques and Assisted Reproductive Technology, The Veterinary Clinics of North America, Equine Practice, vol. 12, No. 1, Apr. 1996, pp. 127-130.

Squires, E.L, Moran, D.M., Farlin, ME., Jasko, D.J., Keefe, T.J., Meyers, S.A., Figueiredo, E., McCue, P.M. and Jochle, W. 1994. Effect of dose of GnRH analogue on ovulation in mares. Theriogenology. 41:757-769.

Squires, E.L..., et al, "Cooled and frozen stallion semen", Bulletin No. 9, Colorado State University, Ft. Collins, CO. (1999)-Table of contents only.

Sullivan, J.J., Parker, W.G. and Larson, LL. 1973. Duration of estrus and ovulation time in nonlactating mares given human chorionic gonadotropin during three successive estrous periods. J.A.V.M.A. 162:895-898.

Taljaard, T.L., Terblanche, S.J., Bertschinger, H.J. and Van Vuuren, L.J. 1991. The effect of the laparoscopic insemination technique on the oestrus cycle of the ewe. J. S Afr. Vet. Assoc. 62(2):60-61.

Vazquez, J., et al., "Development of a Non-surgical Deep Intra Uterine Insemination Technique", IV International Conference on Boar Semen Preservation, Maryland, Aug. 1999, p. 35 and photo of display board.

Vazquez, J., et al.,"Hypoosmotic Swelling Test as Predictor of the Membrane Integrity in Boar Spermatozoa", Boar Semen Preservation IV, IVth International Conference on Boar Semen Preservation, Maryland, pp. 263.

Vazquez, J., et al., "Successful Low-Dose Insemination by a Fiberoptic Endoscope Technique in the Sow", Proceedings Annual Conference of the International Embryo Transfer Society, Netherlands, Theriogenology, vol. 53, Jan. 2000, pp. 201.

Vazquez, J., et al., "Nonsurgical Uterotubal Insemination in the Mare", Proceedings of the 44th Annual Convention of the American Association of Equine Practitioners, Baltimore, Maryland, Dec. 6-9, 1998, vol. 44, pp. 68-69.

Vazquez, J., et al., "A.I. in Swine; New Strategy for Deep Insemination with Low Number of Spermatozoa Using a Non-surgical Methodology", 14$^{th}$ International Congress on Animal Reproduction, vol. 2, Stockhlom, Jul. 2000, p. 289.

Vazquez, J., et al., "Development of a Non-surgical Deep Intra Uterine Insemination Technique", IV International Conference on Boar Semen Preservation, Maryland, Aug. 1999, p. 35 and photo of display board.

Vidament, M., Dupere, A.M., Julienne, P., Evain, A., Noue, P. and Palmer, E. 1997. Equine frozen semen freezeability and fertility field results. Theriogenology. 48:907.

Voss, J.L., Pickett, B.W., Burwash, L.D. and Daniels, W.H. 1974. Effect of human chorionic gonadotropin on duration of estrous cycle and fertility of normally cycling, nonlactating mares. J.A.V.M.A. 165:704-706.

Voss, J.L., Squires, E.L., Pickett, B.W., Shideler, R.K. and Eikenberry, D.J. 1982. Effect of number and frequency of inseminations on fertility in mares. J. Reprod. Fertil. Suppl. 32:53-57.

Welch, G., et al., "Flow Cytometric Sperm Sorting and PCR to Confirm Separation of X- and Y- Chromosome Bearing Bovine Sperm", Animal Biotechnology, 6 (2), 131-139, 1995, pp. 131-139.

Welch G.R., et al., 1994. Fluidic and optical modifications to a FACS IV for flow sorting of X- and Y- chromosome bearing sperm based on DNA. Cytometry 17 (suppl. 7): 74.

Wilson, C.G., Downie, C.R., Hughes, J.P. and Roser, J.F. 1990. Effects of repeated hCG injections on reproductive efficiency in mares. Eq. Vet. Sci. 4:301-308.

Wilson, M.S. 1993. Non-surgical intrauterine artificial insemination in bitches using frozen semen. J.Reprod. Fert Suppl. 47:307-311.

Woods, J. and Ginther, O.J. 1983. Recent studies related to the collection of multiple embryos in mares. Theriogenology. 19:101-108.

XP-002103478, File Biosis, (1988), one page.

Beyhan, Z., Welch, G.R. and First, N.L. 1998. Sexual dimorphism in IVF bovine embryos produced by sperm sorted by high speed flow cytometry. Theriogenology. 49(1):359. abstr.

Brethour, J.R. and Jaeger, J.R., "The Single Calf Heifer System", Kansas Agric. Sta. Rep of Progress 570, 1989.

Buchanan, B.R., et al, "Insemination of Mares with Low Numbers of Either Unsexed or Sexed Spermatozoa", Theriogenology, vol. 53, pp. 1333-1344, (2000).

Chin, W.W. and Boime, I. 1990. In: Glycoprotein Hormones. Serona Symp. Norwell, MA. pp. 19-20.

Douglas, R.H. 1979. Review of superovulation and embryo transfer in the equine. Theriogenology. 11:33-46.

Foulkes, J.A., Stewart, D.L. and Herbert, C.N. 1977. Artificial insemination of cattle using varying numbers of spermatozoa. Vet. Rec. 101:205.

Ginther, O.J. 1992. In: Reproductive Biology of the Mare. (2$^{nd}$ Ed.) Equiservices, Cross Plains, WI, front cover of book only.

Gledhill, B.L. 1988. Gender preselection: historical, technical and ethical perspective. Semin Reprod. Endocrinol. 6:385-395.

Grondahl, C., et al, "In Vitro Production of Equine Embryos", Biology of Reproduction, Monograph Series I, pp. 299-307 (1995).

Hunter, R.H.F. 1980. Transport and storage of spermatozoa in the female reproductive tract. Proc 4$^{th}$ Int. Congr. Artira. Repro. and A.I. 9:227-233.

Irvine, C.H.G. and Alexander, S.L. 1993. In: Equine Reproduction. Edited by McKirmon and Voss. Lea and Febiger. Philadelphia, London. pp. 37.

Johnson, L.A., Flook, J.P., Look, M.V. and Pinkel, D. 1987a. Flow sorting of X and Y chromosome-bearing sperm for DNA using an improved preparation method and staining with Hoechst 33342. Gam. Res. 17:1-9.

Johnson, L.A. and Schulman, J.D. 1994. The safety of sperm selection by flow cytometry. Ham. Reprod. 9(5):758.

Johnson, L.A. 1988. Flow cytometric determination of spermatozoa sex ratio in semen purportedly enriched for X or Y bearing spermatozoa. Theriogenology. 29:265. abstr.

Johnson, L.A. 1995. Sex preselection by flow cytometric separation of X and Y chromosome bearing spermatozoa based on DNA difference: a review. Reprod. Fert. Dev. 7:893-903.

Kanayama, K., Sankai, T., Nariaik, K., Erich, T. and Sakuma. 1992b. Pregnancy by means of tubal insemination and subsequent spontaneous pregnancy in rabbits. J. Int. Med. Res. 20:401-405.

Levinson, G., Keyvanfar, K., Wu, J.C., Fugger, E.F., Fields, R.A., Harton, G.L., Palmer, F.T., Sisson, M.E., Starr, K.M., Dennison-Lagos, L., Calvo, L., Sherins, R.J., Bick, D., Schulman, J.D. and Black, S.H. 1995. DNA-based X-enriched sperm separation as an adjunct to preimplantation genetic testing for the preparation of X-linked disease. Mol. Human Reprod. 10:979-982.

Loy, R.G. and Hughes, J.P. 1965. The effects of human chorionic gonadotropin on ovulation, length of estrus, and fertility in the mare. Cornell Vet. 56:41-50.

McCue, P.M. 1996. Superovulation. Vet. Clin. N. Amer. Eq. Prac. 12:1-11.

McCue, P.M., Fleury, J.J., Denniston, D.J., Graham, J.K. and Squires, E.L. 1997. Oviductal insemination in the mare. 7$^{th}$ Int Symp. Eq. Reprod. 133. abstr.

Miller, S.J. 1986. *Artificial Breeding Techniques in Sheep*. In Morrow, D.A. (ed): Current Therapy in Theriogenology 2. Philadelphia, WB Saunders, abstract only.

Mirskaja, L.M. and Petrapavlovskii, V.V. 1937. The reproduction of normal duration of heat in the mare by the administration of Prolan. Probl. Zivotn. Anim. Breed. Abstr. 5:387.

Munne, S. 1994. Flow cytometry separation of X and Y spermatozoa could be detrimental to human embryos. Hum. Reprod. 9(5):758.

Pickett, B.W, et al., 1976. Factors influencing the fertility of stallion spermatozoa in an A.I. program. Proc. 8th Internat. Congr. Anim. Reprod. A.I. Krakow, Poland. 4: 1049-1052.

Pickett GW, et al., "Management of the mare for maximum reproductive efficiency" Bulletin No. 6 Colorado State University, Ft. Collins CO. (1989), table of contents only.

Pickett, B.W. and Back, D.G. 1973. Procedures for preparation, collection, evaluation and insemination of stallion semen. C.S.U. Exp. Sta. Artira. Reprod. Lab. Gen. Series Bull. 935.

Pinkel, D., Gledhill, B.L., Van Dilla, M.A., Stephenson, D. and Watchmaker, G. 1982b. High resolution DNA measurements of mammalian sperrnatozoa. Cytometry. 3:1-9. (1982b).

Roser, JF., Evans, J.W., Kiefer, DP., Neeley, D.P. and Pacheco, C.A. 1980. Reproductive efficiency in mares with anti-hCG antibodies. Proc 9th Int. Congr. Artira. Repro. and A.I. 4:627. abstr.

Schmid R.L., et al, "Fertilization with Sexed Equine Spermatozoa Using Intracytoplasmic Sperm Injection and Oviductal Insemination", 7th International Symposium On Equine Reproduction, pp. 139 (Abstract) (1998).

Seidel, G.E. Jr, et al., "Insemination of Heifers with Sexed Sperm", Theriogenology, vol. 52, pp. 1407-1421 (1999).

Seidel, G.E. Jr., Cran, D.G., Herickoff, L.A., Schenk, J.L., Doyle, S.P. and Green, R.D. 1999. Insemination of heifers with sexed frozen or sexed liquid semen. Theriogenology. 51. (in press). abstr.(1999).

Shilova, A.V., Platov, E.M. and Lebedev, S.G. 1976. The use of human chorionic gonadothrophin for ovulation date regulation in mares. VIIIth Int. Congr. On Anim. Repro. and A.1. 204-208.

Squires, E.L., "Early Embryonic Loss" in Equine Diagnostic Ultrasonography, 1st Ed. pp. 157-163 Eds Rantanen & McKinnon. Williams and Wilkins, Baltimore, Maryland (1998).

Taylor, C.S., Moore, A.J. Thiessen, R.B. and Bailey, C.M., AFRC Animal Breeding Research Organisation, West Mains Road, Edinburg EH9 3JQ, "Efficiency of Food Utilization in Traditional and Sex-Controlled Systems of Beef Production", pp. 401-440, 1985.

Voss, J.L. and Pickett, B.W. 1976. Reproductive management of the broodmare. C.S.U. Exp. Sta. Anim. Reprod. Lab. Gen. Series. Bull. 961.

Woods, J., Bergfelt, D.R. and Ginther, O.J. 1990. Effects of time of insemination relative to ovulation on pregnancy rate and embryonic-loss rate in mares. Eq. Vet. J. 22(6):410-415.

Abdel-Ghaffar, A. E., et al., "Rabbit Semen Metabolism" in Rabbit Production in Hot Climates Baselga and Marai (eds); International Conference of Rabbit Production in Hot Climates 1994, p. 305-312.

Akhtar, S., et al., "Prevalence of Five Stereotypes of Bluetongue Virus in a Rambouillet Sheep Flock in Pakistan", Veterinary Record 136, p. 495. (1995).

Aldrich, S. L., et al., "Parturition and Periparturient Reproductive and Metabolic Hormone Concentration in Prenatally Androgenized Beef Heifers", J. Anim. Sci. 73:3712. (1995).

Amann, R. P. et al., "Issues Affecting Commercialization of Sexed Sperm" Therio. 52:1441. (1999).

Amann, R.P. "Fertilizing Potential Vitro of Semen from Young Beef Bulls Containing a High or Low Percentage of Sperm with a Proximal Droplet" Theriogenology 54: 1499-1515, 2000.

Amann, Rupert P. "Cryopreservation of Sperm" 1999, Encyclopedia of Reproduction 1:733-783.

American Meat and Science Association in Cooperation with National Livestock and Meat Board, "Research Guidelines for Cookery and Sensory Evaluation and Instrumental Tenderness Measurements for Fresh Meat". (1995).

Arriola, J. and Foote, R.H.: "Glycerolation and Thawing Effects on Bull Spermatozoa frozen in Detergent-Treated Egg Yok and Whole Egg Extenders," J Dairy Sci, 70:1664-1670 (1987).

Asbury, Charles A. "Fluorescence Spectra of DNA Dyes Measured in a Flow Cytometer," University of Washington Feb. 19, 1996.

Bagley, C. P. "Nutritional Management of Replacement Beef Heifers: a Review" J. Anim. Science 71:3155-3163. (1993).

Bailey, C. M. et al., "Nulliparous Versus Primiparous Crossbred Females for Beef", J. Anim. Sci. 69:1403. (1991).

Bakker Schut, Tom C. "A New Principle of Cell Sorting by Using Selective Electroportation in a Modified Flow Cytometry," University of Twente, Mar. 10, 1990.

Barnes, F. L. and Eyestone, W. H., "Early Cleavage and the Maternal Zygotic Transition in Bovine Embryos", Therio. vol. 33, No. 1, pp. 141-149. (1990).

Batellier, F. et al., "Advances in Cooled Semen Technology" Animal Reproduction Science 68 p. 181-190 (2001).

Behrman, S. J., et al., "Freeze Preservation of Human Sperm" American Journal of Obstetrics and Gynecology vol. 103 (5) p. 654-664 Mar. 1, 1969.

Bellows, R. A., et al., "Cause and Effect Relationships Associated With Calving Difficulty and Calf Birth Weight", J. Anim. Sci. 33:407. (1971).

Berardinelli, J. G., et al., "Source of Progesterolle Prior to Puberty in Beef Heifers". J. Anim. Sci. 49:1276. (1979).

Bergfeld, E. G., et al., "Ovarian Follicular Development in Prepubertal Heifers is Influenced by Level of Dietary Energy Intake", Bio. of Repro. 51:1051. (1994).

Berry, B. W., et al., "Beef Carcass Maturity Indicators and Palatability Attributes", J. Anim. Sci. 38:507 (1974).

Beyhan, Z., Et Al., 1999 Sexual Dimorphism In IVM-IVF Bovine Embryos Produced from X and Y Chromosome-Bearing Spermatozoa Sorted By High Speed Flow Cytometry. Theriogenology. 52: 35-48.

BigosBigos, Martin "Nine Color Eleven Parameter Immunophenotyping Using Three Laser Flow Cytometry," Stanford University Dec. 22, 1998.

Bioxcell, Bovine Sperm Preservation, Advertisement Jun. 28, 2005.

Bond, J., et al., "Growth and Carcass Traits of Open Beef Heifers Versus Beef Heifers That Have Calved", Nutrition Reports International 34:621. 1986.

Boucque, C. V., et al., "Beef-Production With Maiden and Once-Calved Heifers", Livestock Prod. Sci. 7:121. 1980.

Bourdon, R. M. and J. S. Brinks. "Simulated Efficiency of Range Beef-Production III. Culling Strategies and Nontraditional Management-Systems", J. Anim. Sci. 65:963. 1987.

Brethour, J. R. and Jaeger, J. R., "The Single Calf Heifer System", Kansas Agric. Sta. Rep of Progress 570. 1989.

Brookes, A. J. and O'Byrne, M., "Use of Cow-Heifers in Beef Production" J. of the Royal Agricultural Society of England 126:30. 1965.

Buchanan, B.R. "Pregnancy Rates in Mares Following a Single Insemination with a Low Number of Spermatozoa into the Tip of the Uterine Horn" Theriogenology p. 395, 1999.

Burns, P. D. and Spitzer, J.C., "Influence of Biostimulation on Reproduction in Postpartum Beef-Cows", J. Anim. Sci. 70:358. 1992.

Byerley, D. J., et al., "Pregnancy Rates of Beef Heifers Bred Either on Puberal or Third Estrus". J Anim. Sci. 65:645. 1987.

Catt, S. L., et al., "Birth of a Male Lamb Derived from an In Vitro Matured Oocyte Fertilized by Intracytoplasmic Injection of a Single Presumptive Male Sperm", Veterinary Record 139, p. 494-495. 1996.

Cave-Penney, Tony, "Sexed Semen Offers Faster Genetic Gain", Farming News, Livestock Supplement, Feb. 1997, p. 28.

*Celestron: Telescope Basics*: www.celestron.com/tb-2ref/htm; 4 pages.

Cf. Milovanov V.K. "Biology of reproduction and artificial insemination of animals". Moscow, Izdatelstvo Selskokhoziastvennoi Literatury, 1962,pp. 392-619.

Chandler, J. E., "Videomicroscopic Comparison of Bull Sperm and Leukocyte Chromosome Areas as Related to Gender", J Dairy Sci 73, p. 2129-2135. 1990.

Chandler, J. E., et al, "Bovine Spermatozoal Head Size Variation and Evaluation of a Separation Technique Based on this Size", Therio. 52, p. 1021-1034. 1999.

Chen, S.H. "Effects of Oocyte Activation and Treatment of Spermatozoa on Embryonic Development Following Intracytoplasmic Sperm Injection in Cattle" Theriogenology 48: 1265-1273, 1997.

Chen, Y. et al., Survival of Bull Spermatozoa Seeded and Frozen at Different Rates in Egg Yolk-Tris and Whole Milk Extenders, 1993 J Dairy Sci 76:1028-1034.

Choi, Y.H. "Developmental Cappacity of Equine Oocytes Matured and Cultured in Equine Trophoblast-Conditioned Media" Theriogenoogy 56: 320-339, 2001.

Cran, D. G., et al., "Sex Preselected in Cattle: A Field Trial", Veterinary Record 136, 1995, p. 495-496.

Cran, D. G., et al., "The Predetermination of Embryonic Sex Using Flow Cytometrically Separated X and Y Spermatozoa" Human Reproduction Update 1996, vol. 2 (4) p. 355-363.

Crowley, J. P. "The facts of Once-Bred Heifer Production" School of Agric., Univ. of Aberdeen, Scotland. 1973.

Cui, K. et al, "X Larger than Y", Nature 366, p. 177-118, 1993.

Cui, K., "Size Differences Between Human X and Y Spermatozoa and Prefertilization Diagnosis", Molecular Human Reproduction, vol. 3, No. 1, pp. 61-67. 1997.

da Silva, Coutinho M.A.."Effect of time of oocyte collection and site of insemination on oocyte transfer in mares." Animal Reproduction and Biotechnology Laboratiory, Colorado State Uniuversity, Fort Collins Journal of Animal Science 2002. 80:1275-1279.

*DakoCytomation, "MoFlo® Sorters"* http://www.dakocytomation.us/prod_productrelatedinformation?url=gprod_moflo_index.htm one page, printed Jun. 26, 2003.

Database up 1 BR9704313 (Alves, De Resende et al) Jun. 4, 1999.

de Leeuw, F.E. et al:"Effects of carious cryoprotective agents and membrane-stabilizing compounds on bull sperm emebrane integrity after cooling and freezing" Cryobiology US, Academic Press Inc 1993 pp. 32-44.

Denham, A. "In-vitro studies on Sandhill Range Forage as Related to Cattle Preference", M.S. Thesis. Colorado State University. 1965.

Denk, Winfried. "Two-Photon Molecular Excitation in Laser-Scanning Microscopy," Handbook of Biological Confocal Microscopy. 1995.

Deutscher, G. H. "Extending Interval From Seventeen to Nineteen Days in the Melengestrol Acetate-Prostaglandin Estrous Synchronization Program for Heifers". The Professional Animal Scientist 16:164. 2000.

*Diagnostic Products Corporation, "Coat-A-Count"* http://www.Progesterone.com. 1998.

Dikeman, M. E. "Cattle Production Systems to Meet Future Consumer Demands" J. Anim. Sci. 59:1631, 1984.

Dinnyes, A., et al., "Timing of the First Cleavage Post- Insemination Affects Cryosurvival of In Vitro-produced Bovine Blastocysts", Molec. Reprod. Develop. 53, p. 318-324. 1999.

Dippert, K.D. "Fertilization Rates in Superovulated and Spontaneously Ovulating Mares" Theriogenology 41: 1411-1423, 1994.

Doyle, S. P., et al. "Artificial Insemination of Lactating Angus Cows with Sexed Semen". Proc. Western Sect. Am. Soc. Anim. Sci. 50:203. 1999.

Dresser D.W. et at. Analysis of DNAcontent of Living Spermatozoa Using Flow Cytometry Technique Journal of Reproduction and Fertility, 1993, vol. 98, pp. 357-365.

Ferrell, C. L. Effects of Post-Weaning Rate of Gain on Onset of Puberty and Productive Performance of Heifers of Different Breeds. J. Anim. Sci. 55:1272. 1982.

Ferrell, C. L. and T. G. Jenkins. "Energy-Utilization by Mature, Nonpregnant, Nonlactating Cows of Different Types" J. Anim. Sci. 58:234. 1984.

Field, R. A., et al., "Bone-Ossification and Carcass Characteristics of Wethers Given Silastic Implants Containing Estradiol", J. Anim. Sci. 68:3663-3668. 1990.

Field, R. et al., "Growth, Carcass, and Tenderness Characteristics of Virgin, Spayed, and Single-Calf Heifers", J. Anim. Sci. 74:2178. 1996.

Foote, et al. Motility and Fertility of Bull Sperm Frozen-Thawed Differently in Egg Yolk and Milk Extenders Containing Detergent, 1987 J Dairy Sci 70:2642-2647.

Foote, R.H., "Buffers and Extenders: What Do They Do? Why Are They Important?" Proc of the NAAB Tech. Conf. On Artificial Insemination and Reproduction, 62-70 (1984).

Francon, M. and Yamamoto, T., "Un Noveau et tres simple dispositif interferentiel applicable as microscope" Optica Acta 9, p. 395-408. 1962.

Fuller, Robert R. "Characterizing Submicron Vesicles With Wavelenth-Resolved Fluorescence in Flow Cytometry," University of Illinois, May 13, 1996.

Gombe, S. and Hansel, W. "Plasma Luteinizing Hormone (LH) and Progesterone Levels in Heifers on Restricted Energy Intakes." J. Anim. Sci. 37:728. 1973.

Goppert-Mayer,"Uber Elementarakte mit zwei Quantensprungen Von Maria Copper -Mayer".

Gottlinger et al., "Operation of a Flow Cytometer", Flow Cytometry and Cell Sorting, A. Radbruch (Ed.), 1992, pp. 7-23.

Graham, J. Analysis of Stallion semen and its Relation to Fertility. Abstract, Vet Clinic N. American. 1996. 12, p. 119.

Graham, J.K. and Hammerstedt, R.H.: "Differential Effects of Butylated Hydroxytoluene Analogs on Bull Sperm Subjected to Cold-Induced Membrane Stress," Cryobiology, 29:106-117 (1992).

Graham, James K., "Effect of Cholesterol-Loaded Cyclodextrins in Semen Extenders", Proceedings of the 19th Technical Conference on Artificial Insemination & Reproduction, 2003, pp. 91-95.

Gravert, H. O., "Genetic Aspects of Early Calving." In: J.C. Taylor (Ed.) *The Early Calving of Heifers and Its Impact on Beef Production*. 59 (1975).

Gregory, K. E., et al., "Characterization of Biological Types of Cattle—Cycle III: II Growth Rate and Puberty in Females" J. Anim. Sci. 49:461 (1979).

Grimes, I. F, and T. B. Turner. "Early Weaning of Fall Born Calves II. Post Weaning Performance of Early and Normal Weaned Calves". I. Prod. Agric. 4:168 (1991).

Hall, J. B., et al., "Effect of Age and Pattern of Gain on Induction of Puberty with a Progestin in Beef Heifers." J. Anim. Sci. 75:1606 (1997).

Hamamatsu, "Technical Information, Optical Detector Selection: A Delicate Balancing Act", web page, http://www.optics.org/hamamatsu/photodiode.html, printed on Apr. 15, 2000, 6 pages total.

Hamamatsu, Photomultiplier Tubes, www.optics.org/hamamatsu/mrnt.html printed on Apr. 15, 2000 4 pages.

Hamano, K., et al., "Gender Preselection in Cattle with Intracytoplasmically Injected, Flow Cytometrically Sorted Sperm Heads", Biology of Reproduction 60, p. 1194-1197 (1999).

Hammerstedt, et al., "Cryopreservation of Mammalian Sperm: What We Ask Them to Survive," Journal of Andrology, 11:1:73-88 (1990).

Harte, F. J. "System of Production of Beef From Once Calved Heifers." In: J.C. Taylor (Ed.) *The Early Calving of Heifers and its Impact on Beef Production*. 123 (1975).

Hermesmeyer, G. N., et al. "Effects of Prenatal Androgenization and Implantation on the Performance and Carcass Composition of Lactating Heifers in the Single-Calf Heifer System." The Professional Animal Scientist 15:173. 1999.

Hermesmeyer, G. N., et al. "Effects of Lactation and Prenatal Androgenization on the Performance and Carcass Composition and Longissimus Muscle Sensory Characteristicts of Heifers in the Single-Calf Heifer System." The Professional Animal Scientist 15:14-23. 1999.

Herweijer, Hans. "High-Speed Photodamage Cell Selection Uing Bromodeoxyuridine/Hoechst 33342 Photosensitized Cell Killing," Sep. 23, 1987.

Herzenberg, Leonard A. "Flourescence-activated Cell Sorting," pp. 108-117.

Hilton, G. G., et al., "An Evaluation of Current and Alternative Systems for Quality Grading Carcasses of Mature Slaughter Cows." J. Anim. Sci. 76:2094. 1998.

Ho, L., et al., "Influence of Gender, Breed and Age on Maturity Characteristics of Sheep." J. Anim. Sci. 67:2460-2470. 1989.

Hohenboken, W. D. "Applications of sexed semen in cattle production." Therio. 52:1421. 1999.

Horan, Paul K. "Quantitative Single Cell Ana,lysis and Sorting Rapid Analysis and sortng of cells is emerging as an important new technology in research and medicine." Science. 1977. 198: 149-157.

IMV Technologies, Protocol of Bioxcell with Fresh Semen, 1 page, 2000.

IMV Technologies, Protocol of Bioxcell with Frozen Semen, 2 pages, 2000.

Iwazumi, Y., et al., "Superovulation Using CIDR in Holstein Cows" J. of Reprod. Dev. vol. 40 (3) 1994, pp. 259-266.

Jakubiczka, S. et al. "A Bovine Homologue of the Human TSPY Gene." Genomics. 1993, vol. 17, No. 3, pp. 732-735.

Jarriage, R. "Age of Cows at First Calving in France." In: J.C. Taylor (Ed.) *The Early Calving of Heifers and its Impact on Beef Production*. 10. (1975).

Jasko, D. J., et al., "Pregnancy Rates Utilizing Fresh, Cooled and Frozen-Thawed Stallion Semen", American Association of Equine Practitioners 38th Annual Convention Proceedings, 1992, p. 649-60.

Johnson, L.A., "Gender Preselection in Humans? Flow Cytometric Separation of X and Y Spermatozoa for the Prevention of X-Linked Diseases" Human Reproduction vol. 8 No. 10, p. 1733-1739 (1993).

Johnson, L.A., "Sex Preselection in Swine: Flow Cytometric Sorting of X- and Y- Chromosome Bearing Sperm to Produce Offspring", Boar Semen Preservation IV, p. 107-114. (2000).

Johnson, L.A., "Successful Gender Preselection in Farm Animals", Agricultural Biotechnology, p. 439-452. (1998).

Joseph, R. L. "Carcass composition and meat quality in once calved heifers." In: J.C. Taylor (Ed.) *The Early Calving of Heifers and its Impact on Beef Production*. 143. (1975).

Joseph, R. L. and J. P. Crowley. "Meat Quality of Once-Calved Heifers." Irish J. of Agric. Research 10:281. (1971).

Karabinus, et al., "Effects of Egg Yolk-Citrate and Milk Extenders on Chromatin Structured Viability of Cryopreserved Bull Sperm", Journal of Dairy Science, vol. 74, No. 11, p. 3836-3848. (1999).

Keeling, P. "A Modeling Study of Once-Bred Heifer Beef Production." Proceedings of the New Zealand Society of Animal Production. 51. (1991).

Kinder, J. E., et al. "Endocrine Basis for Puberty in Heifers and Ewes." J. Repro. and Fertility, p. 393. (1995).

Kinder, J. E., et al., "Endocrine Regulation of Puberty in Cows and Ewes." J. Repro. and Fertility, Suppl. 34:167. (1987).

Kinoshita, Shuichi. "Spectroscopic Properties of Fluorescein in Living Lymphocytes," Osaka Uinversity Aug. 7, 1986.

Klindt, J. and J. D. Crouse. "Effect of Ovariectomy and Ovariectomy with Ovarian Autotransplantation on Feedlot Performance and Carcass Characteristics of Heifers." J. Anim. Sci. 68:3481. (1990).

Klosterman, E. W. and C. F. Parker. "Effect of Size, Breed and Sex Upon Feed Efficiency in Beef Cattle." North Central Regional Research Publication 235, Ohio Agric. Research and Development Center 1090:3. (1976).

Kniffen, D. M., et al., "Effects of Long-Term Estrogen Implants in Beef Heifers." J. Anim. Sci. 77:2886. (1999).

Kobata, Akira, "Structures and Functions of the Sugar Chains of Human Chorionic Gonadotropin", in *Glycoprotein Hormones* Chin, W.W. and Boime, I., eds. Serono Symposia, Norwell, MA. p. 19-20. 1990.

Koch, R. M., et al., "Characterization of Biological Types of Cattle -Cycle-II .3." Carcass Composition, Quality and Palatability. J. Anim. Sci. 49:448. (1919).

Kommisrud E., et al. "Comparison of Two Processing Systems for Bull Semen with Regard to Post-Thaw Motility and Nonreturn Rates." Theriogenology, vol. 45, 1996, pp. 1515-1521.

Laster, D. B., "Factors Affecting Dystocia and Effects of Dystocia on Subsequent Reproduction in Beef-Cattle." J. Anim. Sci. 36:695. (1973).

Lightwave Electronics, "Xcyte," www.LightwaveElecronics.com.

Lindsey, A. C., et al., "Low Dose Insemination of Mares Using Non-Sorted and Sex-Sorted Sperm" Animal Reproduction Science 68 p. 279-89 (2001).

Liu, Z, et al. "Survival of Bull Sperm Frozen at Different rates in Media Varying in Osmolarity." Cryobiology, vol. 27, 1998, pp. 219-230.

Lonergan, P., et al., "Effect of Time Interval from Insemination to First Cleavage on the Development of Bovine Embryos In Vitro and In Vivo", Therio. p. 326 (1999).

Long, C.R., et al., "In Vitro Production of Porcine Embryos From Semen Sorted for Sex With a High Speed Cell Sorter: Comparison of Two Fertilization Media." Therio. 49(1): 363 (1998) abstr.

Lu, K. H. et al., "In Vitro Fertilization of Bovine Oocytes with Flow-Cytometrically Sorted and Unsorted Sperm from Different Bulls" Therio. abstr., 1999. 52: 1393.

Lu, K. H., et al., "In Vitro Fertilization with Flow-Cytometrically-Sorted Bovine Sperm", Therio 52, p. 1393-1405. (1999).

Lynch, I. M., et al., "Influence of timing of gain on growth and reproductive performance of beef replacement heifers." J. Anim. Sci. 75:1715. (1997).

Manni, Jeff. "To-Photon Excitation Expands the Capabilities of Laser-Scanning Microscopy," 1996, 44 Biophot Int.

Manning, S.T., et al., "Development of Hysteroscopic Insemination of the Uterine Tube in the Mare", Proceedings of the Annual Meeting of the Society for Theriogenology, 1998, p. 84-85.

Martin, A. H., et al., "Characteristics of Youthful Beef Carcasses in Relation to Weight, Age and Sex. III. Meat Quality Attributes." Canadian J. Anim. Sci. 51:305. (1971).

Martin, L. C., et al., "Genetic-effects on Beef Heifer Puberty and Subsequent Reproduction." J. Anim. Sci. 70:4006. (1992).

Martinez, E. A., et al., "Successful Low-Dose Insemination by a Fiberoptic Endoscope Technique in the Sow", Proceedings Annual Conference of the International Embryo Transfer Society, Netherlands, Therio. vol. 53 p. 201, Jan. 2000.

Matulis, R. J., "Growth and carcass characteristics of cull cows after different times-on-feed." J. Anim. Sci. 65:669. (1987).

Mauleon, P. "Recent research related to the physiology of puberty." In: J.C. Taylor (ed.) *The Early Calving of Heifers and its Impact on Beef Production*. (1975).

Maxwell, W. and Johnson, L., "Chlortetracycline Analysis of Boar Spermatozoa After Incubation, Flow Cytometric Sorting, Cooling, or Cryopreservation", Molecular Reproduction and Development 46, p. 408-418. (1997).

Maxwell, W. M. C., et al., "The Relationship Between Membrane Status and Fertility of Boar Spermatozoa After Flow Cytometric Sorting in the Presence or Absence of Seminal Plasma" Reprod. Fertil. Dev. vol. 10 p. 433-40 (1998).

Maxwell, W. M. C., et al., "Viability and Membrane Integrity of Spermazota after Dilution and Flow Cytometric Sorting in the Presence or Absence of Seminal Plasma." Reprod. Fertil. Dev. 8:1165-78. (1997).

McCormick, R. J. "The Flexibility of the Collagen Compartment of Muscle." Meat Sci. 36:79. (1994).

McLeod, John H., "The Axicon: A New type of Optical Element", Journal of the Optical Society of America, vol. 44 No. 8, Aug. 1954, Eastman Kodak Company, Hawk-Eye Works, Rochester, New York.

Meilgaard, M., et al., "Sensor Evaluation Techniques." CRC Press Inc., Boca Raton, FL. (1991).

Melamed et al, "An Historical Review of the Development of Flow Cytometers and Sorters", 1979, pp. 3-9.

Mendes Jr., J.O.B. "Effect of heparin on cleavage rates and embryo production with four bovine sperm prepration protocols" Theriogenology 60 (2003) 331-340.

Menke, E. A Volume Activated Cell Sorter Journal of Histo chemistry and Cyto Chemistry, 1977, vol. 25,No. 7, pp. 796-803.

Merton, J., et al., "Effect of Flow Cytometrically Sorted Frozen/Thawed Semen on Success Rate of In Vitro Bovine Embryo Production", Therio. 47, p. 295. (1997).

Metezeau P. et al. Improvement of Flow Cytometry Analysis and Sorting of Bull Spermatozoa by Optical Monitoring of Cell Orientation as Evaluated by DAN Specific Probing Molecular Reproduction and Development, 1991,vol. 30 pp. 250-257.

Moe, P. W., "Energetics of Body Tissue Mobilization." J. of Dairy Sci. 54:548, 1971.

Moran, C., et al., "Puberty in Heifers -a Review." Animal Reproduction Sci. 18:167. (1989).

Moran, D. M. et al., "Determination of Temperature and Cooling Rate Which Induce Cold Shock in Stallion Spermatozoa", Therio. vol. 38 p. 999-1012 (1992).

Morgan, J. B., et al., "National Beef Tenderness Survey." J. Anim. Sci. 69: 3274. (1991).

Morris, S. T., et al., "Biological efficiency: How relevant is this concept to beef cows in a mixed livestock seasonal pasture supply context?" Proceedings of the New Zealand Society of Animal Production 54:333. (1994).

Moseley, W. M., et al., "Relationship of Growth and Puberty in Beef Heifers Fed Monensin" J. Anim. Sci. vol. 55 No. 2 p. 357-62 (1982).

Mount, D. E. "Fibrous and Non-fibrous Carbohydrate Supplementation to Ruminants Grazing Forage From Small Grain Crops." M.S. Thesis. Abstr. Colorado State University. (2000).

Mullis, K. B. and F. A. Faloona, "Specific Synthesis of DNA in Vitro Via a Polymerase-Catalyzed Chain Reaction" Methods in Enzymology vol. 155 p. 335-350 (1978).

Myers, S. E., "Performance and Carcass Traits of Early-Weaned Steers Receiving Either a Pasture Growing Period or a Finishing Diet at Weaning." J. Anim. Sci. 77:311. (1999).

Myers, S. E., et al., "Comparison of Three Weaning Ages on Cow-Calf Performance and Steer Carcass Traits." J. Anim. Sci. 77:323. (1999).

Myers, S. E., et al., "Production Systems Comparing Early Weaning to Normal Weaning With or Without Creep Feeding for Beef Steers." J. Anim. Sci. 77:300. (1999).

Nix, J. P., et al., "Serum Testosterone Concentration, Efficiency of Estrus Detection and Libido Expression in Androgenized Beef Cows." Therio. 49: 1195. (1998).

NRC. "Nutrient Requirements for Beef Cattle." National Academy of Sci. National Research Council, Washington, DC. (1996).

O'Brien, Justine K. et al., "Preliminary Developments of Sperm Sorting Technology in Non-human Primates", Biology of Reproduction 2001(Su;;I. 1) 64:158.

Olive, M.D., "Detection of Enterotoxigenic *Escherichia coli* after Polymerase Chain Reaction Amplification with a Tehrmostable DNA Polymerase", J of Clinical Microbiology, Feb. 1989 p. 261-265.

Olson, S.E. and Seidel, G. E. Jr., "Reduced Oxygen Tension and EDTA improve Bovine Zygote Development in a Chemically Defined Medium", J. of Anim. Sci. 78, pp. 152-157. (2000).

Owen, J. B. "The Maiden Female-A Means of Increasing Meat Production." Proc. Symp. On the Use of Once Bred Heifers and Gilts. (1973).

Patterson, D. J., et al., "Estrus Synchronization with an Oral Progestogen Prior to Superovulation of Postpartum Beef Cows" Therio. 48, 1025-33 (1997).

Penfold, L.M.et at., "Comparative Motility of X and Y Chromosome-Bearing Bovine Sperm Separated on the Basis of DNA Content", Mol. Reprod. And Develop. 1998, vol. 50,pp. 323-327.

Petit, M. "Early Calving in Suckling Herds." In: J.C. Taylor (ed.) *The Early Calving of Heifers and its Impact on Beef Production*. p. 157-176. (1975).

Picket B.W., et al., "Livestock Production Science," 1998.

Pickett, B. W., et al., "Influence of Seminal Additives and Packaging Systems on Fertility of Bovine Spermatozoa." J. Anim. Sci. Suppl. II. 47:12. (1978).

Pickett, B. W., et al., "The Effect of Extenders, Spermatozoa! Numbers and Rectal Palpation on Equine Fertility." Proc. Fifth N.A.A.B Tech. Conf. A. I. Reprod. Columbia, MO. pp. 20-22. (1974).

Pinkel et al., "Flow Chambers and Sample Handling", Flow Cytometry: Instrumentation and Data Analysis, Van Dilla et al. (Eds. ), 1985, pp. 77-128.

Pinkel, D., et al., "Sex Preselection in Mammals? Separation of Sperm Bearing the Y and "O" Chromosomes in the Vole Microtus Oregoni", Science vol. 218 p. 904 (1982).

Piston, D.W. "Three-dimensionally resolved NAD(P)H cellular metabolic redox imaging of the in situ cornea with two-photon excitation laser scanning microscopy," Journal of Microscopy, vol. 178, Nov. 29, 1994.

Polge, E. J., "Historical Perspective of AI: Commercial Methods of Producing Sex Specific Semen, IVF Procedures", Proceedings of the 16th Technical Conference on Artificial Insemination & Reproduction, Cambridge, England, pp. 7-11. (1996).

Polge, et al, "Revival of Spermatozoa After Vitrification and Dehydration at Low Temperatures," Nature, 164:666 (1994).

Preza, C. et al, "Determination of Direction-Independent Optical Path-Length Distribution of Cells Using Rotational-Diversity Transmitted-Light Differential Interference Contrast (DIC) Images", Presented at the Multidimensional Microscopy: Image Acquisition and Processing V, p. 1-11 (1998).

Province, C.A., et al., Cooling Rates, Storage, Temperatures and Fertility of Extended Equine Spermatozoa Therio. vol. 23 (6) p. 925-934, Jun. 1985.

Purvis, H. T. and J. C. Whittier. "Effects of Ionophore Feeding and Anthelmintic Administration on Age and Weight at Puberty in Spring-Born Beef Heifers." J. Anim. Sci. 74:736-744. (1996).

Randel, R. D. "Nutrition and Postpartum Rebreeding in Cattle." J. Anim. Sci. 68:853. (1990).

Rathi, R. et al., "Evaluation of in Vitro Capacitation of Stallion Spermatoza", Biology of Reproduction 2001,vol. 65, pp. 462-470.

Recktenwald, Diether. "Cell Separation Methods and Applications," New York 1997, About the Book, 1 page.

Reiling, B.A., et al., "Effects of prenatal Androgenization, Melengestrol Acetate, and Synovex-H on Feedlot Performance, Carcass, and Sensory Traits of Once-Calved Heifers" J. Anim. Sci. vol. 74 p. 2043-51 (199).

Rieger, D., et al, "The Relationship Between the Time of First Cleavage of Fertilized Cattle Oocytes and Their Development to the Blastocyst Stage", Therio. 1999, p. 190.

Rigby, S. L., et al., "Pregnancy Rates in Mares Following Hysteroscopic or Rectally-Guided Utero-Tubal insemination with Low Sperm Numbers" Abstracts/Animal Reproduction Science vol. 68 p. 331-333 (2001).

Riggs, B.A. "Integration of Early Weaning and Use of Sexed Semen in a Single-Calf Heifer System to Increase Value of Non-Replacement Heifers" MS Thesis, Colorado State University, Spring 2000.

Romero-Arredondo, A. "Effects of Bovine Folicular Fluid on Maturation of Bovine Oocytes" Theriogenology 41: 383-394, 1994.

Romero-Arrendondo, A. "Effects of Follicular Fluid dring In Virto Maturation of Bovine Oocytes on In Vitro Fertilization and Early Embryonic Development" Biology of Reproduction 55, 1012-1016 1996.

Romita, A. "Some Considerations on the Beef Situation in Italy." In: J.C. Taylor (ed.) *The Early Calving of Heifers and its Impact on Beef Production*. 23. (1975).

Roux, M., et al., "Early Calving Heifers Versus Maiden Heifers for Beef-Production from Dairy herds. I. The Effects of Genotype (Friesian and Carloads x Friesian) and Two Feeding Levels in the Rearing Period on Growth and Carcass Quality." Livestock Prod. Sci. 16:1 (1987).

Roy, J. H., "Rearing Dairy-Herd Replacements." Journal of the Society Of Dairy Technology 31:73-79 (1978).

Schenk, John L. "Applying Semen Sexing Technology to the AI Industry", Proceedings of the 18th Technical Conference on Artificial insemination & Reproduction, 2000.

Schiewe, M. C., et al., "Transferable Embryo Recovery Rates Following Different Insemination Schedules in Superovulated Beef Cattle" Therio. 28 (4) Oct. 1997, pp. 395-406.

Schillo, K. K., et al, "Effects of Nutrition and Season on the Onset of Puberty in the Beef Heifer." J. Anim. Sci. 70:3994 (1992).

Schnell, T. D., et al, "Performance, Carcass, and Palatability Traits for Cull Cows Fed High-Energy Concentrate Diets for 0, 14, 28, 42, or 56 days." J. Anim. Sci. 75:1195. (1997).

Schoonmaker, J. P., et al., "Effects of Age at Weaning and Implant Strategy on Growth of Steer Calves." J. Anim. Sci. (Suppl. II) 76:71. (1998) abstr.

Seidel, G "Cryopreservation of Equine Embryos" Veterinary Cliniics of North America: Equine Practice vol. 12, No. 1, Apr. 1996.

Seidel, G. "Sexing Bovine Sperm" The AABP Proceedings—vol. 34, 2001.

Seidel, G. Sexing mammalian spermatozoa and embryos-state of the art Journal of Reproduction and Fertility Supp 54, 477-487 1999.

Seidel, G. E. Jr et al., "Current Status of Sexing Mammalian Spermatozoa," Society for Reproduction and fertiity, pp. 733-743, 2002.

Seidel, G. E. Jr, "Commercilizing Repreductive Biotechnology—The Approach used by XY, Inc.," Theriogenology, p. 5, 1999.

Seidel, G., "Use of Sexed Bovine Sperm for In Vitro Fertilization and Superovulation", Animal Reproduction and Biotech Lab, CSU, Proceedings of the 2000 CETA/ACTE Convention, Charlottetown, Prince Edward Island, Aug. 2000, pp. 22-24.

Seidel, G., "Status of Sexing Semen for Beef Cattle", Texas A & M University 45th Annual Beef Cattle Short Course and Trade Show Proceedings, Aug. 9-11, p. III24-III27, (1999).

Seidel, G., et al, "Sexing Mammalian Sperm—Overview", Therio. 52: 1267-1272, (1999).

Seidel, G.,Economics of Selecting for Sex: The Most Important Genetic Trait, Theriogenology 59, (2003), pp. 585-598.

Sell, R. S., et al., "Single-calf Heifer Profitability Compared to Other North Dakota Beef Production Systems." Department of Ag. Eco., North Dakota State University, Ag. Econ. Rpt. 20.

Shabpareh, V. "Methods for Collecting and Maturing Equine Oocytes in Vitro" Theriogenology 40: 1161-1175, 1993.

Shapiro, Howard M. MD., PC. "Practical Flow Cytometry Third Edition," New York 1994.

Sharpe, J.C., et al., "A New Optical Configuration for Flow Cytometric Sorting of Aspherical Cells" Horticulture and Food Research Institute of New Zealand Ltd., Hamilton, New Zealand (PNS) Nov. 2, 1997 Abstract.

Sharpe, Johnathan, Thesis; "An Introduction of Flow Cytometry", Ch. 2-2.2, 1997.

Sharpe, Johnathan, Thesis; "Gender Preselection-Principle Scientific Options," Ch. 3.4-3.4.8, 1997.

Sharpe, Johnathan, Thesis; "Sperm Sexing using Flow Cytometry," Ch. 3.5-3.5.8, 1997.

Sharpe, Johnathan, Thesis; "Sperm Sexing-Method of Johnson et al," Ch. 3.6-4.3.4, 1997.

Shorthose, W. R. and P. V. Harris. "Effect of Animal Age on the Tenderness of Selected Beef Muscles." J. Food Sci. 55:1-. (1990).

Silbermann, M., "Hormones and Cartilage. Cartilage: Development, Differentiation, and Growth." pp. 327-368. Academic Press, Inc. (1983).

Simon, M., "The Effect of Management Option on the Performance of Pregnant Feedlot Heifers." M.S. Thesis. Kansas State University. (1983).

Skogen-Hagenson, M. J. et al; "A High Efficiency Flow Cytometer," The Journal of Histochemistry and Cytochemistry, vol. 25, No. 7, pp. 784-789, 1977, USA.

Smith, G. C., et al, "USDA Maturity Indexes and Palatability of Beef Rib Steaks." J. of Food Quality 11:1. (1988).

Smith, G. C., et al., "Relationship of USDA Maturity Groups to Palatability of Cooked Beef." J. of Food Sci. 47:1100. (1982).

Smith, R. L., et al, Influence of Percent Egg Yolk during Cooling and Freezing on Survival of Bovine Spermatozoa, Dairy Science 1979 J 62:1297-1303.

*Spectra Physics, The Solid State Laser Company, "Vangaurd 4 Watts of UV from a Quasi-CW, All Solid State Laser,"* http://www.splasers.com/products/isl_products/vangaurd.html three pages, printed Nov. 14, 2002.

*Spectra-Physics Products, "Fcbar"* http://www.splasers.com/products/oem_products/ov_fcbar.html two pages printed Nov. 14, 2002.

Spectra-Physics, The Solid State Laser Company, Vanguard 2000-HMD 532, www.specra-physics.com.

Spectra-Physics, The Solid State Laser Company, Vanguard 350-HMD 355, www.specra-physics.com.

Squires, E. L., "Early Embryonic Loss" *Equine Diagnostic Ultrasonography*, first ed., Rantanen & McKinnon. Williams and Wilkins, Baltimore, Maryland, p. 157-163 (1998).

Squires, E.L., "Procedures for Handling Frozen Equine Semen for Maximum Reproductive Efficiency", pp. 1, 39-41, 81-89.

Staigmiller, R.B. "Superovulation of Cattle with Equine Pituitary Extract and Porcine FSH" Theriogenology 37: 1091-1099 1992.

Stap J. Et al Improving the Resolution of Cryopreserved X- and Y-Sperm During DNA Flow Cytometric Analysis with the Addition of Percoll to quench the Fluorescence of Dead Sperm: Academic Medical Center, University of Amsterdam (1998) Journal of Animal Science vol. 76 1998, pp. 1896-1902.

Steel, N. L., "Cost Effectiveness of Utilizing Sexed-Semen in a Commercial Beef Cow Operation", MS Thesis, Colorado State University, Summer 1998.

Steinkamp: "Flow Cytometry" vol. 55, No. 9, Sep. 1984 pp. 1375-1400, New York Review of Scientific Instruments, Abstract Only.

Stellflug, J. N., "Plasma Estrogens in Periparturient Cow." Therio 10:269. (1978).

Stevenson, J. S., et al., "Detection of Estrus by Visual Observation and Radiotelemetry in Peripubertal, Estrus-Synchronized Beef Heifers." J. Anim. Sci. 74:729. (1996).

Story, C. E., et al., "Age of Calf at Weaning of Spring-Calving Beef Cows and the Effect on Cow and Calf Performance and Production Economics." J. Anim. Sci. 78:1403. (2000).

Stovel R.T. A Means for Orienting Flat Cells in flow systems Biophysical Journal, 1978,vol. 23,pp. 1-5.

Sumner, A. T. and Robinson, J. A., "A Difference in Dry Mass Between the Heads of X and Y-Bearing Human Spermatozoa", J Reprod Fertil. 48, p. 9-15 (1976).

Swanson, E. W. "Future Research on Problems of Increasing Meat Production by Early Calving." In: J.C. Taylor (ed.) *The Early Calving of Heifers and its Impact on Beef Production*. (1975).

Swenson, S. L., et al., "PRRS Virus Infection in Boars: Isolation From Semen and Effect on Semen Quality" from the 1995 Research Investment Report, Iowa State University, Veterinary Clinical Sciences, Iowa State University.

Tatum, J. D., et al., "Carcass Characteristics, Time on Feed and Cooked Beef Palatability Attributes." J. Anim. Sci. 50:833. (1980).

Tervit, H.R., et al., "Successful Culture In Vitro of Sheep and Cattle Ova", Agricultural Research Council, Unit of Reprod. Physio. and Biochem., Univ of Cambridge, p. 493-497 (1972).

Thun, Rico, et al., Comparison of Biociphos-Plus® and TRIS-Egg Yolk Extender for Cryopreservation of Bull Semen; Theriogenology Symposium, Dec. 1999, vol. 52, #8.

*Time-Bandwidth Products "GE—100—XHP"*, www.tbsp.com, 2 pages, Jan. 2002.

Unruh, J. A. "Effects of Endogenous and Exogenous Growth-Promoting Compounds on Carcass Composition, Meat Quality and Meat Nutritional-Value." J. Anim. Sci. 62:1441. (1986).

USDA "Official United States Standards for Grades of Carcass Beef." Agric, Marketing Serv., USDA, Washington, DC. (1997).

Van Dilla, Martin, "Overview of Flow Cytometry: Instrumentation and Data Analysis", Flow Cytometry: Instrumentation and Data Analysis, Van Dilla et al. (Eds.), 1985, pp. 1-8.

Van Munster, E. B., et al, "Difference in Sperm Head Volume as a Theoretical Basis for Sorting X & Y-Bearing Spermatozoa: Potentials and Limitations", Therio 52, pp. 1281-1293 (1999).

Van Munster, E. B., et al, "Difference in Volume of X- and Y-chromosome Bearing Bovine Sperm Heads Matches Difference in DNA Content" Cytometry vol. 35 p. 125-128 (1999).

Van Munster, E. B., et al, "Measurement-Based Evaluation of Optical Path Length Distributions Reconstructed From Simulated Differential Interference Contrast Images", J of Microscopy 191, Pt. 2, p. 170-176 (1998).

Van Munster, E. B., et al, "Reconstruction of Optical Pathlength Distributions From Images Obtained by a Wide Field Differential Interference Contrast Microscope", J of Microscopy 188, Pt. 2, p. 149-157 (1997).

Vincent, B.C., et al, "Carcass Characteristics and Meat Quality of Once-Calved Heifers." Canadian J. Anim. Sci. 71:311. (1991).

Vogel, T., et al, "Organization and Expression of Bovine TSPY", Mammalian Genome, vol. 8, pp. 491-496 (1997).

Watson, "Recent Developments and Concepts in the Cryopreservvation of Spermatozoa and the Assessment of Their Post-Thawing Function," Reprod. Fertil. Dev. 7:871-891 (1995) Abstract.

Wheeler, T. L., et al., "Effect of Marbling Degree on Beef Palatability in Bos-taurus and Bos-indicus cattle." J. Anim. Sci. 72:3145. (1994).

Wickersham, E. W. and L. H. Schultz. "Influence of Age at First Breeding on Growth, Reproduction, and Production of Well-Fed Holstein Heifers." J. Dairy Sci. 46:544. (1963).

Wilson, D. E. et al., "Mammal Species of the World", Smithsonian Institution Press, 1993, 1206 pp.

Windsor, D. P., et al, "Sex Predetermination by Separation of X and Y Chromosome-bearing Sperm: A Review", Reproduction of Fertilization and Development 5, pp. 155-171, (1993).

Zhou, Hongwei, et al. "Research on and Development of Flow Cell Sorting Apparatuses," Gazette of Biophysics, vol. 13, ed. 3, 1997.

* cited by examiner

METHOD OF ESTABLISHING AN EQUINE ARTIFICIAL INSEMINATION SAMPLE

This application is the National Stage of International Application No. PCT/US99/17165 which claims the benefit of U.S. Provisional Application No. 60/094,720, filed Jul. 30, 1998, and U.S. Provisional Application No. 60/113,143, filed Dec. 18, 1998, each priority case is hereby incorporated by reference.

This invention is the result of a joint research agreement between Colorado State University through its agent Colorado State University Research Foundation and XY, Inc. and a joint research agreement between Colorado State University through its agent Colorado State University Research Foundation and Cytomation Inc.

I. TECHNICAL FIELD

This invention relates generally to the field of artificial insemination of equines. It also involves equine artificial insemination when there has been sex selection of the sperm to produce an equine offspring of the desired sex. It is especially relevant to situations where non-surgical equine artificial insemination is desired and also where low dose equine artificial insemination is of practical importance.

II. BACKGROUND

Artificial insemination of equine mares has been of importance for many years. Often this has been accomplished surgically. In routine instances where lower dosages of sperm have not been required, it has been accomplished without surgery by artificial insemination, however this has used relatively high numbers of sperm. For routine artificial insemination of the mare 250-500×10$^6$ progressively motile sperm (pms) inseminated every other day to a mare in estrus, is usually recommended to achieve maximum fertility. Unfortunately, when inseminating mares with semen from a highly fertile stallion, fertility has decreased as the number of motile sperm has been reduced. Under ideal conditions, a mare has been successfully inseminated with as few as 100×10$^6$ pms without reducing fertility, however even this number poses challenges. Insemination with low numbers of sperm is necessary when using sorted sexed semen and frozen thawed semen of limited quantity.

Preselecting the sex of offspring in an equine animal is, of course, of interest. Sex preselection following artificial insemination (AI) with low numbers of separate, enriched populations of X- and Y-chromosome bearing sperm that have been separated on the basis of DNA content is currently possible in other species, however, equine species have in some regards proven more difficult. While birth of progeny of the desired sex following intrauterine insemination of cattle and sheep has validated the sexing technology, until the present invention, it has not been practically applied to equines.

To achieve sex preselection involves separating the X-from the Y-chromosome bearing sperm followed by use for artificial insemination (AI) or for in vitro fertilization (IVF) and subsequent embryo transfer. Current high speed flow cytometry enables researchers to sort >1000 live-sexed sperm/second. Sorting alone, however, is not enough. In order to make semen sexing a practical technique for a commercial equine AI program, a lesser number of motile sperm is required for an insemination dose. In the mare when using fresh semen for AI, a typical insemination dose would contain between 250-500×10$^6$ motile sperm. The current sorting rate of ~1000 live sperm/second, it would take almost six days to sort one insemination dose! Therefore, a lesser number of motile sperm is required to practically achieve reasonable fertility. Once that is achieved, enhanced fertility with non-surgical insemination of mares with sexed semen is also viewed as practically necessary.

As mentioned, sex preselection involves the use of DNA content and separation of sperm into X- and Y-chromosome bearing populations. Using current high speed flow cytometry enables researchers to sort up to 1000 live sperm/sec of the desired sex with 90% accuracy, which provides adequate numbers of sperm in many species other than equines in a reasonable amount of time. For example, this new technology for sperm sexing has made it a practical technique for artificial insemination in cattle. Since it is practical to sort only a low number of spermatozoa and still maintain sperm viability, one aspect of this invention addresses enhanced pregnancy rates following insemination of 25×10$^6$ non sorted, progressively motile spermatozoa (pms). This is about one-tenth of what was previously considered optimal for routine operations. Other aspects address even lower numbers. These aspects can have significant economic consequences when one considers its application to celebrated trophy animals such as horses and the like.

As mentioned, one of the fundamental challenges that efforts at sorting X and Y equine sperm has faced is the large numbers of sperm involved. In natural insemination equine sperm are produced by nearly the billion; in artificial insemination less, but still significantly large numbers of equine sperm are usually used. For instance, equine artificial insemination techniques routinely use two hundred and fifty million to five hundred million sperm. Thus a significant number of sperm have been presumed necessary in an equine artificial insemination environment.

As the invention relates to sex selected artificial insemination, many methods have been attempted to achieve the separation of X- and Y-chromosome bearing sperm in other animals. None of these, however, have dealt with aspects peculiar to or specific sorting of equine sperm cells. General sorting methods have ranged from magnetic techniques such as appears disclosed in U.S. Pat. No. 4,276,139 to columnar techniques as appears disclosed in U.S. Pat. No. 5,514,537 to gravimetric techniques as discussed in U.S. Pat. No. 3,894,529, reissue Pat. No. 32,350, U.S. Pat. Nos. 4,092,229, 4,067,965, and 4,155,831. Electrical properties have also been attempted as shown in U.S. Pat. No. 4,083,957 as well as a combination of electrical and gravimetric properties as discussed in U.S. Pat. Nos. 4,225,405, 4,698,142, and 4,749,458. Motility efforts have also been attempted as shown in U.S. Pat. Nos. 4,009,260 and 4,339,434. Chemical techniques such as those shown in U.S. Pat. Nos. 4,511,661 and 4,999,283 (involving monoclonal antibodies) and U.S. Pat. Nos. 5,021,244, 5,346,990, 5,439,362, and 5,660,997 (involving membrane proteins), and U.S. Pat. Nos. 3,687,803, 4,191,749, 4,448,767, and 4,680,258 (involving antibodies) as well as the addition of serum components as shown in U.S. Pat. No. 4,085,205. While each of these techniques has been presented as if to be highly efficient, in fact at present none of those techniques yield the desired level of sex preselection and none have shown success at the artificial insemination level with equine sperm. Regardless of the separation technique eventually used, however, the competing combinations of the high numbers of equine sperm naturally present and the approach of separating X- and Y-chromosome bearing sperm has made it desirable to develop an ability to achieve equine insemination with lower numbers of sperm.

The quantitative technique used to achieve the separation of X- and Y-chromosome bearing sperm for artificial insemination (of any species) has been that involving the technique of flow cytometry. This technique appeared possible as a result of advances and discoveries involving the differential dye absorption of X- and Y-chromosome bearing sperm. This was discussed early in U.S. Pat. No. 4,362,246 and significantly expanded upon through the techniques disclosed by Lawrence Johnson in U.S. Pat. No. 5,135,759. The Johnson technique of utilizing flow cytometry to separate X- and Y-chromosome bearing sperm has been so significant an advancement that it has for the first time made the commercial separation of such sperm feasible. Further, separation has been significantly enhanced through the utilization of high speed flow cytometers such as the MoFlo® flow cytometer produced by Cytomation, Inc. and discussed in a variety of other patents including U.S. Pat. Nos. 5,150,313, 5,602,039, 5,602,349, and 5,643,796 as well as international PCT patent publication WO 96/12171. While the utilization of Cytomation's MoFlo® cytometers has permitted great increases in speed, and while these speed increases are particularly relevant given the high number of equine sperm often used, certain problems have still remained. In spite of the almost ten-fold advances in speed possible by the MoFlo® flow cytometer, shorter and shorter sorting times have been desired for several reasons. First, it has been discovered that as a practical matter, the equine sperm are time-critical cells. They lose their effectiveness the longer they remain unused. Second, the collection, sorting, and insemination timings has made speed an item of high commercial importance. Thus, the time critical nature of the equine sperm cells and of the process has made speed an essential element in achieving high efficacy and success rates in artificial insemination.

In spite of some successes in sorting and then artificially inseminating animals of other species, the effort with equines has proven particularly elusive. As relevant to the present invention, equine applications may have been particularly challenging either because the equine conception process and/or the equine sperms cells themselves are more delicate than those of other species—especially bovines. For this reason, it may even be that those skilled in the art have not viewed techniques or systems developed for other species as applicable to equines. In some instances almost identical procedures from a non-equine species do not provide the same type of result for equines. This may have fostered separation in the research efforts and in the techniques and substances developed.

Other problems also exist ranging from the practical to the theoretical. On the practical side, it has been desired to achieve equine artificial insemination in a manner that can be done in the field rather than a laboratory environment. Thus, for commercial production and success in the field, improvements which might only represent an increase in efficiency or practicality may still be significant. Related to the practical aspect, is the aspect of the delicateness and sensitivity of the entire process. In this regard, it has been desired to simplify the process and make it as procedurally robust as possible so that operator error or skill can play an ever decreasing role. This goal has also combined to make insemination with lower dosages even more desirable.

In addition to the delicateness of the process, it has always been known that the sperm in general are extremely delicate cells. While this factor at first glance seems like it might be considered easily understood, in fact, the full extent of the cells' sensitivities have not yet been fully explored. Furthermore equine sperm appear particularly sensitive. In contrast to bovine sperm, they are in many ways more delicate from the perspective of successful artificial insemination. Different sensitivities arise and thus there has to some degree been a perception that the systems, techniques, and substances used in other animals (such as bovines) may not always be adaptable to equines. This has in fact proven to be true.

In the context of flow cytometry in general, most sorted cells or particles have often been physically able to withstand a variety of abuses. This is not the case for equine sperm cells. In fact, as the present invention discloses, the processing through normal flow cytometer techniques may, in fact, be unacceptable for cytometric sorting of equine sperm cells in certain applications. The sensitivities range from dilution problems and the flow cytometer's inherent need to isolate and distinguish each cell individually as well as the pressure and other stress which typical flow cytometry has (prior to the present invention) imposed upon the equine cells it was sorting. This may also represent a unique factor for equine sperm cells because it appears that even though the equine sperm cell may appear to pass through the flow cytometer and be sorted with no visually discernable side-effects, in fact, the cells themselves may have been stressed to the point that they perform less than optimally in the insemination process. Thus, an interplay of factors seems involved and has raised unusual problems from the perspective of equine sperm cell sorting and ultimate use for equine artificial insemination.

Another problem which has remained—in spite of the great advances achieved through the Johnson patent and related technology—is the fact that prior to the present invention it has been extremely difficult to achieve lower dosage insemination with sexed equine sperm, regardless of the separation technology used. While historically, some achievement of low dose insemination has occurred, it has appeared to be more in a theoretical or laboratory environment rather than in environments which are likely to be experienced in or applicable to a commercial application. It has also occurred through surgical techniques. In this regard, the desire has not been merely to achieve low dose insemination but even to achieve non-surgical insemination in a field environment. To achieve low dose insemination with pregnancy success rates which are comparable to existing unsexed, high dosage artificial insemination efforts is thus quite significant. The advances achieved by the present inventors in both sexed, unsexed, and low dose artificial insemination represent significant advances which may, for the first time, make commercial applications feasible to equids.

Another problem which has been faced by those in the industry—again, in spite of the great advances by the Johnson patent and related technology—is the fact that the problem itself, namely, equine artificial insemination with a high success rate is one of a statistical nature in which a multitude of factors seem to interplay. Thus, the solutions proposed may to some degree involve a combination of factors which, when thoroughly statistically studied, will be shown to be necessary either in isolation or in combination with other factors. Such a determination is further compounded by the fact that the results themselves vary by species and may be difficult to ascertain due to the fact that testing and statistical sampling on a large enough data base is not likely to be worth the effort at the initial stages. For these reasons the invention can also involve a combination of factors which may, individually or in combination, represent the appropriate solutions for a given application. This disclosure is thus to be considered broad enough so that the various combinations and permeations of the techniques disclosed may be achieved. Synergies may exist with other factors. Such factors may range from factors within the sorting, or perhaps, flow cytometer, steps to those in the collection as well as insemination steps. Thus, while there has been a long felt but unsatisfied need for high speed, low dose sexed equine insemination, and while certain of the implementing arts and elements have long been available, prior to the present invention the advances or perhaps combinations of advances had apparently been overlooked by those skilled in the art. It may even be that the proper combination of known elements simply was not realized. Perhaps to some degree those in the field may have failed to appreciate that the problem involved an interplay of factors as well as peculiar necessities for equine sperm cells involved in this field. Interestingly, as the listing of efforts later in this discussion shows, substantial attempts had been made but they apparently failed to understand the problem inherent in such an area as low dose, sexed insemination of equines and had perhaps assumed that because the natural service event involves perhaps a billion sperm, there may have been physical limitations to the achievement of artificial insemination with numbers which are as many as three orders of magnitude less in number. Thus, it may not be surprising that there was to some extent an actual teaching away from the technical direction in which the present inventors went. Perhaps the results may even be considered unexpected to a degree because they have shown that sexed, low dose equine artificial insemination—if done right—can be achieved with success rates comparable to those of unsexed, high dose equine artificial insemination. It might even be surprising to some that the techniques and advances of the present invention in fact combine to achieve the great results shown. While each technique might, in isolation, be viewed by some as unremarkable, in fact, the subtle changes or combination with other techniques appear to afford significant advances in the end result.

Thus, in one regard until the present invention the achievement of non-surgical practical equine artificial insemination low dose, sexed artificial insemination of equines has not been possible with levels of performance necessary or simplified procedures likely to be necessary to achieve commercial implementation. Beyond low dose, sexed insemination on a commercial level, however achieved, the present invention also discloses techniques which permit the achievement of improved performances and thus facilitates the end result desired, namely, low dose, sexed and unsexed non-surgical artificial insemination of equines on a commercial basis.

III. DISCLOSURE OF INVENTION

Accordingly, the invention discloses the achievement of systems for the non-surgical artificial insemination of equine mares. These techniques are applicable for the use of low dosages of equine sperm and are designed so as to be able to be used in the field on a commercial and practical level. Further, the systems are usable in conjunction with—and have especially valuable applicability to—artificial insemination with sexed equine sperm. The systems also provide for an improved ability to sort equine sperm cells to determine their sex through flow cytometer separation techniques. Various techniques and substances are represented but as those skilled in the art will readily understand, various combinations and permutations can be used in the manner which may be optimized for performance based on the needs, separation techniques, goals and other parameters involved in a specific equine processing application.

As it relates to the sexed equine application, The objectives of the invention were to 1) compare pregnancy rates in mares inseminated on a single occasion, close to ovulation, with 500, 25, or $5 \times 10^6$ progressively motile spermatozoa (pms), 2) achieve reasonable pregnancy rates following insemination with 25 $10^6$ live-sorted, sexed spermatozoa, and 3) develop techniques for sorting semen.

In one of the initial experiments, sixty-one mares were randomly assigned to 1 of 3 treatments: Group 1 (n=20) were inseminated into the uterine body with $500 \times 10^6$ sperm (controls). Group 2 (n=21) and group 3 (n=20) were inseminated in the tip of the uterine horn ipsilateral to the preovulatory follicle with 25, and $5 \times 10^6$ sperm. Mares were administered cloprostenol (250 μg i.m.) to induce luteolysis and monitored by ultrasonography every other day until a follicle $\geq 30$ mm was detected, and then daily until ovulation was detected. GnRH (deslorelin 2.2 mg, Ovuplant®, Fort Dodge) was administered when the dominant follicle was $\geq 35$ mm. Mares were inseminated 34 (n=29) or 40 hours (n=32) after GnRH. Data from 22 mare cycles were excluded because they either ovulated prior to planned insemination (n=11), did not ovulate (n=3), or ovulated >4 days after GnRH administration (n=8). Semen was collected and immediately diluted with a skim milk extender (EZ-Mixin, OF, Animal Reproduction Systems, Chino, Calif.) to either $25 \times 10^6$ or $5 \times 10^6$ motile sperm/ml. Mares receiving 1 ml were inseminated with a flexible plastic artificial insemination pipette (IMV, France), while mares receiving 0.2 ml were inseminated using a disposable implant gun (Veterinary Concepts, Green Valley, Wis.) containing a 0.5 ml straw. Different insemination pipettes were used to optimize delivery of the two different volumes. The location of pipettes within the uterus was confirmed by transrectal ultrasonography prior to semen deposition.

Pregnancy was determined by ultrasonography at 16 days after ovulation. Pregnancy rates were not different between stallions (P>0.05), so results from the two stallions were combined. There was a difference in pregnancy rates for mares bred with $500 \times 10^6$ (18/20=90%) versus $25 \times 10^6$ treatments (12/21=57%) (P<0.05). There was no difference between mares bred with 25×106 versus $5 \times 10^6$ treatments (7/20=35%) (P>0.05). There was no difference in pregnancy rates between mares bred 34 vs. 40 hours after GnRH administration 19/29 (65%) and 18/32 (56%), respectively (P>0.1). There was also no difference in pregnancy rates between mares bred with $5 \times 10^6$ sperm in a volume of 1 ml, 3/10 (30%) or a volume of 0.2 ml, 4/10 (40%) (P>0.05). In summary, pregnancy rates decreased as the number of motile spermatozoa inseminated decreased in this initial effort. However, a day-16 pregnancy rate of 57% was achieved with a single insemination, close to ovulation, with $25 \times 10^6$ pms when deposited into the tip of the uterine horn.

In another experiment, seventeen mares were randomly assigned to 1 of 2 treatment groups: Group A (n=11) mares were inseminated with approximately $25 \times 10^6$ live sorted sperm in a volume of 1 ml. Sperm were sorted into a commercial skim milk semen extender (EZ-Mixin, OF, Animal Reproduction Systems, Chino, Calif.). One mare failed to ovulate and was excluded from the study. Group B (n=10) mares were inseminated with approximately $25 \times 10^6$ live sorted sperm in a volume of 1 ml. Sperm were sorted into EZ-Mixin+4% egg-yolk (EY) Two mares (one from each group) were inseminated with $20 \times 10^6$ sperm because of time constraints with the flow cytometers. In both groups, inseminations were performed 34 hr after GnRH administration and sperm were deposited into the tip of the uterine horn, ipsilateral to the preovulatory follicle using a flexible plastic AI pipette. The location of the pipettes within the uterus was confirmed by transrectal ultrasonography prior to semen deposition. Mares were administered cloprostenol (250 μg i.m.) to induce luteolysis and monitored by ultrasonography every other day until a follicle ≧30 mm was detected, and then daily until ovulation was detected. GnRH (deslorelin 2.2 mg, Ovuplant®, Fort Dodge) was administered when the dominant follicle was ≧35 mm. Two stallions were used in this experiment, one of which (Stallion A) was used in Experiment 1. Freshly collected semen was extended 1:1 in HBGM-3 and centrifuged for 10 minutes at 400×g at 22° C. The supernatant was aspirated and sperm were incubated in 25 µl Hoechst 33342 at 400×10$^6$ sperm/ml in HBGM-3 for 1 hr at 35° C. and then diluted to 100×10$^6$ sperm/ml for sorting. Sperm were sorted for sex chromosomes based on a difference in DNA content. Two MoFlo® flow cytometer/cell sorters equipped with an Argon laser emitting 150 mW power at 352 and 364 nm, operating at 50 psi with HBGM-3 as sheath fluid were used for sorting. Aliquots of sorted X and Y populations were reanalyzed for DNA and gave purities of 90 and 84% for X and Y, respectively. Sperm were collected at approximately 900 sperm/sec into 14 ml tubes containing either 4 ml EZ-Mixin (Group A) or 4 ml EZ-Mixin+4% egg-yolk (Group B). Collected sperm were centrifuged and suspended to 25×10$^6$ sperm/ml and immediately inseminated. Pregnancy was determined by ultrasonography at 12, 14, 16 and 30 days post-ovulation, and fetuses were sexed 60-70 days post-ovulation without knowledge of the sex of the sorted sperm inseminated. Pregnancy rates were not different between stallions (Stallion A=3/10, 30%; Stallion B=5/10, 50%) (P>0.1), so the data sets were combined. Although there was no difference in pregnancy rates between sperm treatments (EZ-Mixin=3/10, 30% versus 4% EY+EZ-Mixin=5/10, 50%) (P>0.1) this may not ultimately prove to be true. At day-60, 5/20 (25%) mares were pregnant; fetuses were sexed and the phenotypic sex ratio was predicted perfectly, five out of five.

This trial has demonstrated for the first time, that pregnancy in the mare can be achieved, and foals of predetermined sex can be obtained, following non-surgical insemination with sexed semen. This is explained in the following discussion. In addition, to the extent they may be helpful, more general sexed insemination aspects and those applicable to equines specifically are discussed in PCT Publication No. WO 99/33956 by the owner of this application. Further, the original disclosures of this invention are set forth in U.S. Patent Applications, Ser. Nos. 60/094,720 and 60/113,143. Each of these prior documents are hereby incorporated by reference for convenience.

Thus, an object of the invention is thus to achieve artificial insemination of equines in a field environment with no need to resort to surgical procedures. Further, a goal is to provide the ability to use lower dosages in a manner which works under realistic commercial circumstances and which yields pregnancy success probabilities which are comparable to traditional equine dosage success rates. An object is also to achieve better sorting for equine sperm cells. A parallel goal is to provide substances and techniques which are especially suited for equine sperm cells when being separated into X- and Y-chromosome bearing components. Thus a goal is to achieve a sorted result which is consistent with unsorted, high dosage expectations.

A goal is also to present an overall system for equine artificial insemination which can achieve its objects in a commercially practical manner. Sorting in a manner which affords both high speed and low stress equine sorting, and which is especially adapted for equine sperm cell sorting in a low dose context is an important goal as well.

Naturally further objects of the invention are disclosed throughout other areas of the specification and claims.

IV. BRIEF DESCRIPTION OF DRAWINGS

V. BEST MODE FOR CARRYING OUT THE INVENTION

Figure 1:
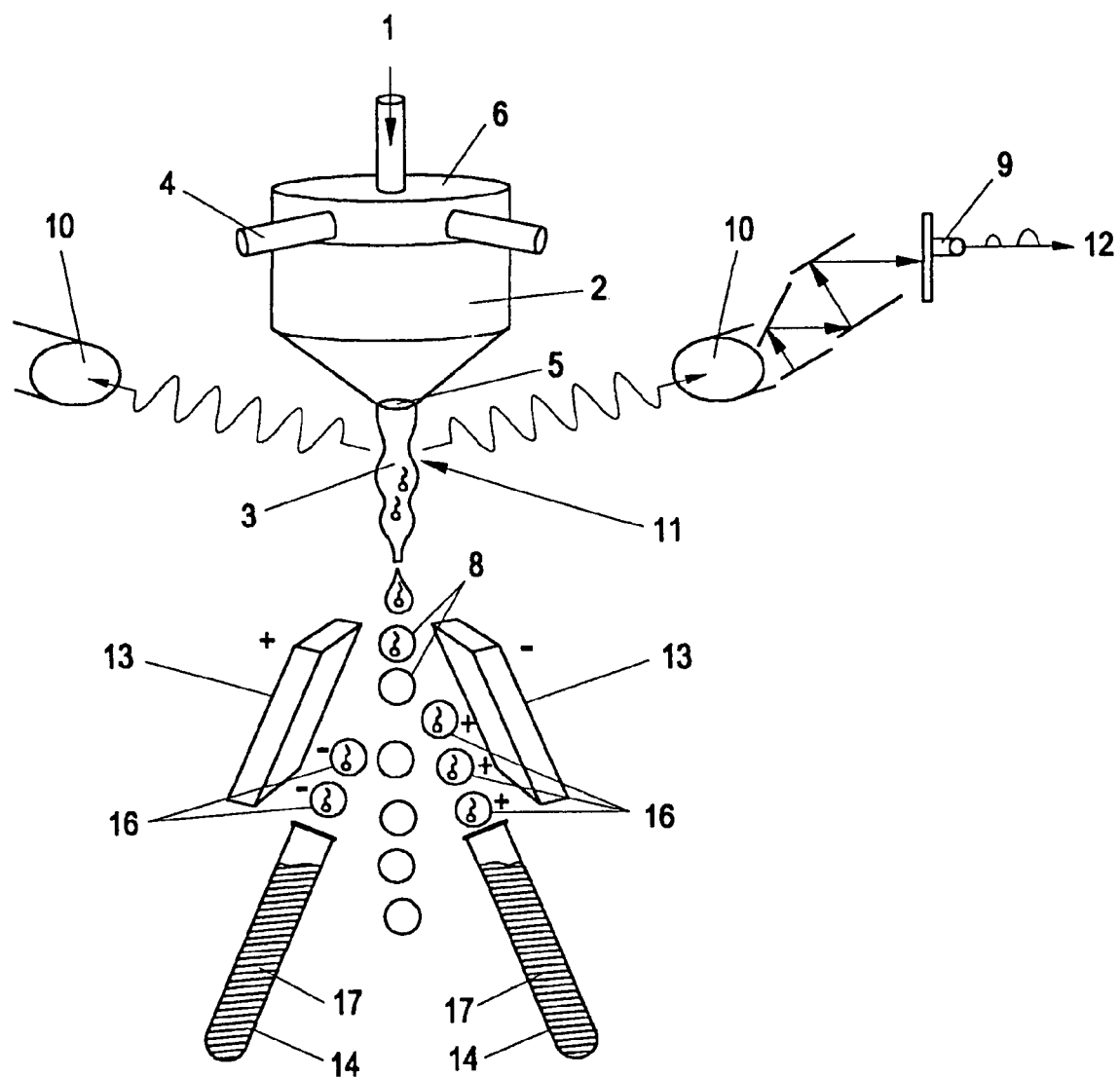
FIG. 1 is a diagram of a sorter system according to a flow cytometer separation technique for the present invention.

As will be seen, the basic concepts of the present invention can be combined and embodied in a variety of ways. The invention involves commercially practical low dose, sexed equine artificial insemination and the results. For flow cytometry separation techniques, the invention also involves both improved flow cytometer systems as well as systems for the creation of sex-specific equine sperm samples which may be used in equine artificial insemination and the equids produced by such techniques. It discloses overall processes through which high success rates are possible even in commercial equine environments. Furthermore, the techniques are disclosed in a general fashion so that they may be applied to specific systems and applications once the general principles are understood. While device enhancements are disclosed it should be understood that these enhancements not only accomplish certain methods but also can be varied and combined in a number of ways. Importantly, as to all of the foregoing, each of these facets should be understood to be encompassed by this disclosure.

When considering the sex selection aspect of the invention, the basic goal is that of separating the X-bearing sperm from the Y-bearing equine sperm in a way that then can be used to artificially inseminate the mare with high success rates. Preferably this insemination would not require surgery. The separation phase is preferably done in a manner which isolate the two types of equine sperm so that each can be separately packaged and dealt with. At present the isolation is preferably done through the use of flow cytometry. Flow cytometry in general is a technique which is well understood. For instance, the basic aspects of it are shown and discussed in a variety of patents to Cytomation, Inc. such as the U.S. Patents and other publications listed earlier. In addition, some details as applicable to equines and other species are disclosed in PCT Publication No. WO 99/33956. Each of these publications and the references cited therein, are incorporated by reference so those skilled in the art can easily understand the basic principles involved.

In general, it should be understood that during meiosis in the testis, the sex chromosomes segregate into individual spermatids and haploid spermatozoa carry either the X or Y chromosome. There is a 50:50 ratio of X- to Y-bearing spermatozoa in the semen, and fertilization of an X-bearing, haplold oocyte by either an X- or Y-bearing sperm determines the sex of the embryo. A 50:50 ratio exists because X- and Y-bearing spermatozoa are made in equal numbers and are phenotypically identical. The desire to alter this 50:50 ratio and predetermine the sex of mammalian offspring has been of great interest to the public for many years. There are numerous benefits to sex preselection in equine animals. Sex preselection has also been used to produce females when heritable X-linked diseases are an issue. Unlike humans and most farm animals, the advantage of sex preselection in the horse can also be purely one of preference to the breeder/owner and there has been considerable interest expressed by members of certain breed registries.

For years, numerous attempts to separate X- from Y-chromosome bearing spermatozoa have been made based on physical and chemical properties of sperm. Johnson (referenced earlier) tested these methods and found that the only method proven effective was based on a difference in DNA content of the spermatozoa. No other method based on a physical difference within the spermatozoa or on surface properties has been proven effective in separating X- from Y-bearing spermatozoa. Within equines, DNA content of mammalian X- and Y-chromosome bearing sperm differs by 4.1%. This difference in DNA content can be used to separate X- and Y-chromosome bearing spermatozoa after staining sperm with a fluorescing, DNA binding dye followed by flow cytometry.

Modern flow cytometry/cell sorting technology was first developed by Fulwyler in 1965. Flow cytometry has mainly been used in medical research and diagnoses with respect to blood and tumor cells, but can also be used to evaluate many types of cell suspensions including sperm cells. Essentially, flow cytometry as applied here involves sorting equine sperm cells, which are provided to the flow cytometer instrument through some type of cell source. A conceptual instrument is shown in FIG. 1. The flow cytometer instrument includes a sample input, here an equine sperm cell source (1) which acts to establish or supply equine sperm cells or some other type of item to be analyzed by the flow cytometer. The cells are deposited within a nozzle (2) in a manner such that the cells are surrounded by a sheath fluid (3). The sheath fluid (3) is usually supplied by some sheath fluid source (4) so that as the equine sperm cell source (1) supplies its cells, the sheath fluid (3) is concurrently fed through the nozzle (2). In this manner it can be easily understood how the sheath fluid (3) forms a sheath fluid environment for the equine sperm cells. Since the various fluids are provided to the flow cytometer at some pressure, they flow out of nozzle (2) and exit at the nozzle orifice (5). By providing some type of oscillator (6) which may be very precisely controlled through an oscillator control, pressure waves may be established within the nozzle (2) and transmitted to the fluids exiting the nozzle (2) at nozzle orifice (5). Since the oscillator (6) thus acts upon the sheath fluid (3), the stream (7) exiting the nozzle orifice (5) eventually and regularly forms drops (8). Because the cells are surrounded by a sheath fluid environment, the drops (8) may contain within them individually isolated cells or other items.

Since the drops (8) generally contains isolated equine sperm cells, the flow cytometer can distinguish and separate droplets based upon whether or not the appropriate cell or cells is/are contained within the drop. This is accomplished through a cell sensing system (9). The cell sensing system involves at least some type of detector (10) (which may include two detectors at 90 degrees with respect to each other) which responds to the cells contained within each drop (8) as discussed at length in the seminal work (no pun intended) by Larry Johnson, namely, U.S. Pat. No. 5,135,759. As the Johnson patent explains for sperm cells, the cell sensing system (9) may cause an action depending upon the relative presence or relative absence of a particular dye which may be excited by some stimulant such as the laser exciter (11). While each type of sperm cell is stained by the dye, the differing length of the X-chromosome and the Y-chromosome causes different levels of staining. Thus, by sensing the degree of dye present in the sperm cells it is possible to discriminate between X-bearing sperm and Y-bearing sperm by their differing emission levels.

In order to achieve the ultimate separation and isolation of the appropriate cells in a flow cytometer separation technique, the signals received by detector (10) are fed to some type of sorter discrimination system (12) which very rapidly makes the decision and can differentially charge each drop (8) based upon whether it has decided that the desired equine sperm cell does or does not exist within that drop (8). In this manner the sorter discrimination system (12) acts to permit the electrostatic deflection plates (13) to deflect drops (8) based on whether or not they contain the appropriate cell or other item. As a result, the flow cytometer acts to sort the cells by causing them to land in one or more collectors (14). Thus by sensing some property of the cells or other items the flow cytometer can discriminate between equine sperm cells based on a particular characteristic and place them in the appropriate collector (14). In the system presently used to sort equine sperm, the X-bearing sperm droplets are charged positively and thus deflect in one direction, the Y-bearing sperm droplets are charged negatively and thus deflect the other way, and the wasted stream (that is unsortable cells) is uncharged and thus is collected in an undeflected stream into a suction tube or the like.

Figure 2:
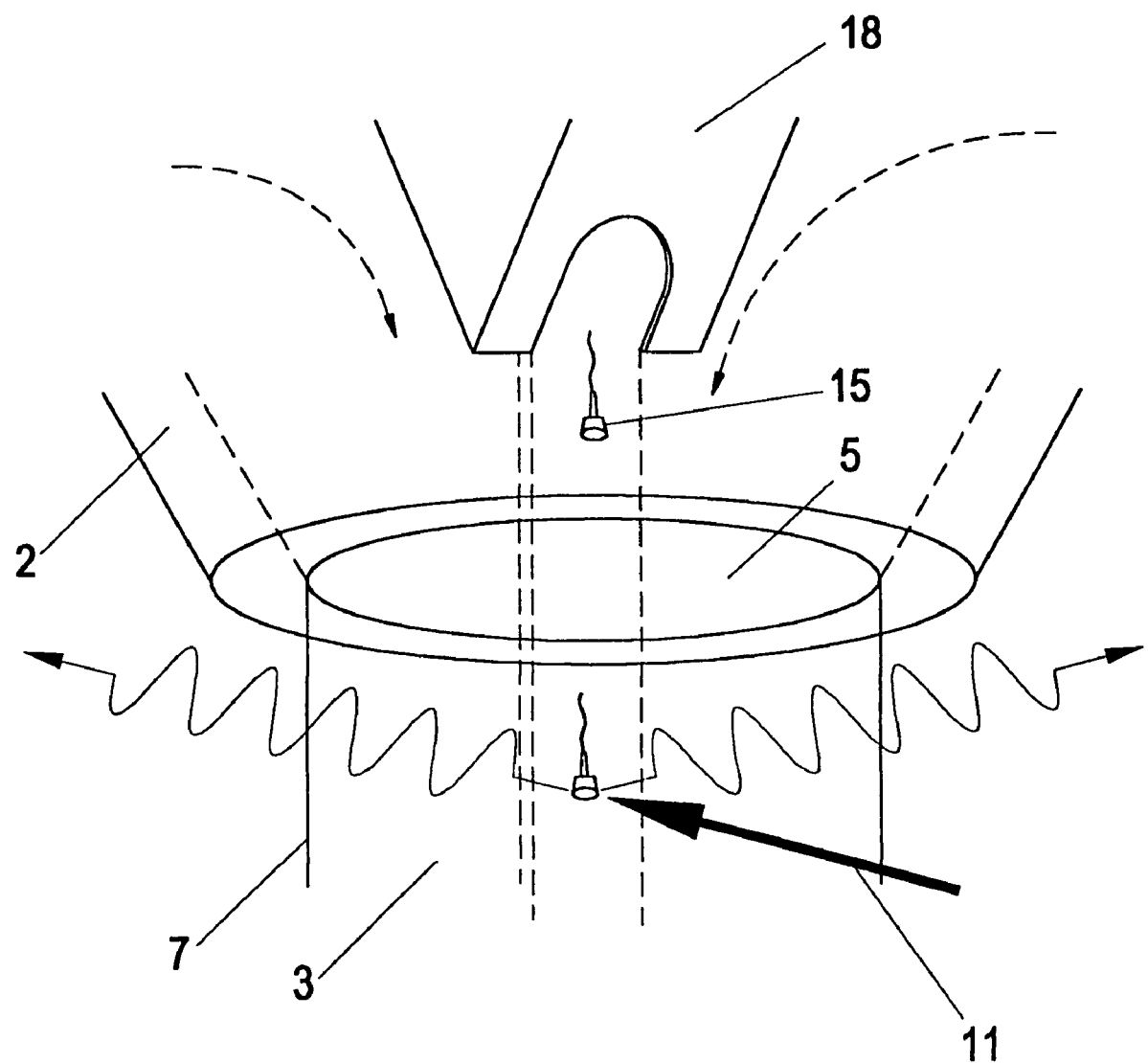
FIG. 2 is a diagram of the entrained cells in the nozzle just prior to the free fall area of a typical flow cytometer.

Referring to FIG. 2, the process can be even further understood. As shown in that figure, the nozzle (2) emits a stream (7) which because of the oscillator (6) (not shown in FIG. 2) forms drops (8) (not shown in FIG. 2). Since the equine sperm cells source (1) (not shown in FIG. 2) may supply equine sperm cells (15) which have been stained according to the Johnson technique, the light stimulation by laser exciter (11) and differentially determined state as sensed by detector (10) can be used to create the existence or nonexistence of a charge on each drop (8) as it separates from stream (7). This is all controlled by the flow cytometer. This control results in positively charged, negatively charged, and uncharged drops (8) based upon their content. As shown in FIG. 1, certain drops are shown as deflected drops (16). These deflected drops (16) are those containing sperm cells (15) of one or the other sex. They are then deposited in the appropriate collector (14) for later use.

As shown in FIG. 2, the equine sperm cells (15) may be injected into the sheath fluid (3) by a needle or injection tube (18). As those skilled in the flow cytometry arts understand, this injection tube (18) can be shaped so as to achieve hydrodynamic focusing and orientation so that both the tail and/or the flatter side of the equine sperm cells (15) are properly oriented. It may even produce a ribbon shaped sample core stream as shown. This can be important since the ninety degree fluorescence intensity can be viewed as proportional to sperm head orientation and the zero degree flourescence intensity can be viewed as porportional to the sperm DNA content.

High resolution flow cytometric DNA analysis of equine sperm is difficult compared to other cells because the highly compacted chromatin in the morphologically flat, paddle shaped sperm head, causes a high index of refraction. The difference in refractive index between the sperm head and the surrounding medium, in combination with the flat shape of the sperm head, results in more emission of fluorescence through the plane of the cell (from the edge of the sperm head) than at a 90° angle to the plane. Proper orientation of the head is critical for high resolution sorting. Others have investigated methods of controlling the orientation of sperm heads flowing in a stream and found that a beveled injected tube (18) was effective in subjecting cells to planar hydrophobic forces as the cells flowed out the end of the needle. The sample stream can be pushed into a ribbon shaped stream which can orient the flat head of the sperm in the same manner. Other, more complex, physical principles are often applied to orient sperm as well.

As mentioned, spermatozoa that undergo the sorting process are stained with the fluorochrome stain Hoechst 33342, chemically known as bisbenzimide. The dye is added to the sample at approximately 9 μM in a 1 ml volume containing $400\times10^6$ sperm, and may be incubated at 32-35° C. Hoechst 33342 is non-toxic to sperm, and does not significantly alter sperm motility. Hoechst 33342 binds to the A-T regions of the DNA helix. Since the sorting process is more productive if dead sperm are not collected, a molecule which quenches the Hoechst 33342 fluorescence and marks dead sperm can be added to the stained sample. Food coloring is one example of a nontoxic molecule that has been used. The process is then that fluorescently stained spermatozoa are introduced under pressure (e.g. 50 psi) in liquid suspension to the flow cytometer. The sperm enter the sample insertion tube and are oriented in one way or another, perhaps as they exit the beveled end of the tube into sheath fluid. The stream containing the sperm intersects an Argon-ion laser beam, in ultraviolet (351 and 364 nm) wavelengths at up to 200 mW of power. Approximately 7% of the drops contain a sperm cell when the sample is at $100\times10^6$ sperm/ml. The fluorescently stained nuclei are excited by the laser beam, giving off fluorescent signals proportional to the amount of DNA bound to the dye.

A modified commercial flow sorting system was used to analyze and sort spermatozoa based on DNA differences. As mentioned, the fluorescent signal from the sperm edge (90° angle from laser emission) is brighter than that emitted from the flat side (0° forward detector). The edge emission is used to characterize the orientation of the sperm heads as they pass the laser beam. The emitting light is collected by the 90° detector, and properly oriented sperm are recognized. Sperm that are not oriented properly give off less light and are electronically gated out of the analyses often, because of the lack of proper orientation, the majority of sperm are not separated into X or Y enriched populations. Also, many sperm cells that are properly oriented are not sorted because of the distributions of fluorescence overlap. An optical detector and a photomultiplier tube (PMT) can be used for the 0° detection of fluorescence, which is proportional to the DNA content of properly oriented sperm. The PMT's collect the fluorescence emitted by the sperm and convert the optical signal into a proportional electronic signal, which is amplified by the PMT for further signal processing and graphic display. Electronic gating enables selection of signals from the 0° forward detector only for properly oriented sperm; this results in the ability to differentiate between the DNA of X and Y sperm. By setting the electronic sort windows around the resolved populations, X- and Y-bearing sperm are separated into two tubes. Two optical detectors collect the light given off, and circuits are activated which add a charging pulse (+ or −) to the drops containing the respective X- or Y-bearing sperm. As the individual sperm droplets fall, they pass an electrostatic field that pulls the charged droplets containing sperm into separate tubes which contain "catch fluid" extender as a temporary holding medium until the sperm are further processed.

Spermatozoa samples which have been separated into X- and Y-chromosome-enriched samples can be reevaluated for their purity using flow cytometric analysis for the DNA content of the individual sperm. In the past, the only valid method for verification of separation available was to determine the sex ratio of the offspring which is untimely and expensive. Re-analyses using flow cytometry reduces not only time and cost, but increases the precision.

With advances it is anticipated that the percent of sperm that are oriented properly as the droplets pass the laser can increase, resulting in increased sorting rates from 100 live sperm/s of each sex to rates between 1000 and 1500 live sperm/s of each sex at ~90%. This increase in the sperm sorting rate would be helpful to make it more practical to utilize sexed semen in an equine artificial insemination program.

Others have reported using the amount of DNA in sperm as a marker for sex preselection and subsequent birth in rabbits of the predicted sex following surgical insemination. Spermatozoa were separated into X- and Y-chromosome bearing populations with a flow cytometer/cell sorter. Sorted sperm were surgically inseminated into the uterus. From does inseminated with fractions enriched for Y-bearing sperm, 81% of offspring born were male; fractions enriched for X-bearing sperm resulting in 94% females. Thus the sex ratio was significantly altered from 50:50. This phenotypic (and genotypic) ratio was accurately predicted based on the reanalysis for DNA from the sorted populations, which showed purities of 81% for Y-bearing sperm and 86% for X-bearing sperm. This was followed by publication of experiments in swine, and cattle. In vitro fertilization has been used to obtain pregnancies in cattle using sexed semen. For example, one researcher transferred twin embryos into each of 9 heifers. Four heifers became pregnant and 6 calves were born, all of the predicted sex. These results show that viable sperm can be separated into X- and Y-chromosome bearing populations and retain their capacity for fertilization and producing normal progeny. Pregnancies following in vitro fertilization (IVF) with X- and Y-bearing sperm have also been obtained in swine and rabbits. Recently, bovine embryos have been produced by IVF with sperm sorted by high speed flow cytometry, but embryo transfers were not done.

Using sorted-sexed equine sperm in a laboratory environment, one researcher performed two experiments to determine pregnancy rates with intracytoplasmic sperm injection (ICSI) into equine oocytes or oviductal insemination. Thirteen injected oocytes developed to the 2- to 3-cell stage, 8 to the 4- to 6 cell stage and 2 oocytes developed to the 7- to 8-cell stage. One embryo was transferred at the 7- to 8-cell stage, but no pregnancy resulted. In the oviductal insemination experiment, two mares were inseminated by cannulation of the fimbriated end of the oviduct with 50 μl containing $1.5\times10^5$ sorted X-bearing sperm. One pregnancy was detected and the mare produced a female foal.

One of the aspects of flow cytometry which is particularly important to its application for equine sperm sorting is the high speed operation of a flow cytometer. Advances have been particularly made by the flow cytometers available through Cytomation, Inc. under the MoFlo® trademark. These flow cytometers have increased sorting speeds extraordinarily and have thus made flow cytometry a technique which is likely to make feasible the commercial application of equine sperm sorting (among other commercial applications). They act to achieve high speed sorting, that is at a speed which is notably higher than those otherwise utilized. Specifically, Cytomation's MoFlo® flow cytometers act with oscillator frequencies of greater than about five kilohertz and more specifically can be operated in the 10 to 30 or even the 50 kilohertz ranges. Thus droplets are formed at very high frequencies and the cells contained within the sheath fluid environment can be emitted very rapidly from the nozzle (2). As a result, each of the components such as the nozzle (2) oscillator (6), and the like which make up and are part of a flow cytometer system can be configured or selected to result in a high speed cell sorter. In the application of a high speed cell sorter to the sorting of sperm cells, sorting at rates of greater than about 900 sorts per second is achieved. Importantly, it should be understood that the term "high speed" is a relative term such that as other advances in flow cytometry and specific applications are achieved, the aspect which is considered "high" may be varied or may remain absolute. In either definition, the general principle is that the sorting may occur at rates at which the parameters and physical characteristics of the flow cytometer are significant to the cells themselves when sorting particular cells such as equine sperm cells.

One aspect of high speed sorting which appears to come into play when sorting equine sperm cells through a flow cytometer separation technique is that of the pressures and other stresses to which the equine sperm cells are subjected within the flow cytometer. For instance, when operating at high speeds (and an alternative definition of "high speed"), flow cytometers can be operated at a pressure of 50 pounds per square inch and even higher. These pressures may be considered high because they may result in effects upon the equine sperm cells being sorted. The key as disclosed in the present invention for this facet is the fact that the stress thresholds of the particular cells are the determining factor. Additionally as further knowledge is gained it may be shown that the stress thresholds are a function of combined effects such as the particular species or the particular prior or subsequent handling of the equine sperm cells. The key in this regard is that the stress imposed upon the equine sperm cells can, in fact, alter their viability and their ability to achieve the desired result. This may be unusually true for equine species. In the pressure case, it may be that merely subjecting the sperm cells to a higher pressure as a result of the operation of the flow cytometer at that pressure may result in decreased performance of the equine sperm cells. The present invention in one regard acts to minimize these stresses and thus results in greater efficacies as well as lower dosages as discussed later.

In considering the stress aspect of the equine cells, the present invention acts in a fashion which minimizes the stresses. These stresses can be minimized at any point in the over-all cycle or process of collecting, sorting or even inseminating the animal. Importantly, the stress imposed by the handling of the cells within the flow cytometer appears significant for equine species. In one embodiment of the invention, the sheath fluid is specifically selected so that it can serve in a coordinated fashion with both (or either) the pre-sort cell fluid environment or the post-sort cell fluid environment. Thus the present invention acts to minimize the changes through the type of operation or the selection of substances which may act as a means for minimizing the changes which the equine sperm cells experience. For the sheath fluid, a substance is selected according to one embodiment of the invention so that it may be chemically coordinated to present minimal changes. Thus, by selecting the appropriate sheath fluid not only in context of flow cytometry parameters, but rather also in context of the equine sperm cell and equine artificial insemination parameters themselves, the changes experienced by the cells and the over all result of the sorting can be enhanced. Interestingly, for equine sperm cells, it has been discovered that a hepes buffered medium such as a hepes bovine gamete medium—particularly HBGM3 as previously created by J. J. Parrish for a bovine application—works well. This medium is discussed in the article "Capacitation of Bovine Sperm by Heparin", 38 Biology of Reproduction 1171 (1988) (hereby incorporated by reference). Not only is this surprising because it is not the same type of use as for bovine sperm, but the actual buffer, was originally developed for a bovine application. Thus in the equine application the sheath fluid is selected which contains the hepes buffer.

A separate aspect of the flow cytometer processing which may also be important is the fact of properly treating the cells both chemically and physically after they are sorted. As shown in FIG. 2, the cells within drops (8) land in collector (14). The collector fluid (17) can also serve to minimize stresses upon the cells. In one regard, since it may be important to provide a nutrient to the cells both before and after sorting, the collector fluid (17) may be selected so as to provide an easier reception as well. For equine sperm cells, the cells may be collected in a commercial skim milk extender such as that from EZ-Mixin, Animal Reproduction Systems, Chino, Calif. Even though intended for a different purpose, this extender can be used as the collection fluid for equine sperm cells. Further, this collection fluid may include 4% egg yolk as well.

Another aspect which may interplay in the various factors of the present invention is that of utilizing low dose amounts of sperm for artificial insemination or the like. Additional background on the aspect of sexed, artificial insemination may be found in "Prospects for Sorting Mammalian Sperm" by Rupert P. Amman and George E. Seidel, Jr., Colorado Associated University Press (1982) and in the previously referenced PCT publication, each hereby incorporated by reference. As mentioned earlier, natural insemination in equines involves numbers of sperm on the order of a billion of sperm. Routine artificial insemination is presently conducted with two hundred-fifty million or more sperm for equine species. By the term "low dose" it is meant that the dosage of sperm utilized in the insemination event are less than one-quarter or preferably even less than about 10% or 5% of the typical number of sperm provided in a typical equine artificial insemination event. Thus, the term "low dose" is to be viewed in the context of the typical artificial insemination dosage or also as an absolute number. The absolute numbers may be species dependent, of course. For equine species, merely less than about twenty-five, ten, five, or even one million sperm may be considered a low dose process.

Yet another aspect which may be important is the fact that the sperm sexed through the present invention techniques (or otherwise) is utilized in an equine artificial insemination system. Thus when, for a flow cytometer technique, the collector (14) is used to provide sperm for artificial insemination the techniques of the present invention may be particularly relevant. Further, it is possible that the combination of both equine artificial insemination use and the use in a low dose environment may together create synergies which makes the various techniques of the present invention particularly appropriate. Naturally, the sexed sperm can be utilized not just in an artificial insemination mode, but in other techniques such as in vitro fertilization and the like.

The process of collecting, sorting, and eventually inseminating an animal through the use of a flow cytometry sorting, or other separation technique, involves a variety of steps. In the context of equine insemination, first the semen is collected from the stallion. Semen may be collected from stallions of known high fertility immediately prior to planned insemination. This may occur with a Colorado model artificial vagina (Animal Reproduction Systems, Chino, Calif.) equipped with an in-line gel filter. Ejaculates can then be evaluated for gel free-volume, motility and spermatozoal concentration. Semen can be then extended with a commercial skim-milk glucose extender (EZ-Mixin, OF, Animal Reproduction Systems, Chino, Calif.) to either $25 \times 10^6$ pms/ml (n=51) or $5 \times 10^6$ pms/ml (n=10). Semen may be kept at room temperature until inseminations were performed, shortly after collection. Staining may be accomplished according to a multi-stained or single-stained protocol, the latter, the subject of the Johnson Patent and related technology.

After adding the stain, dilution or extending to the desired sort concentration may be accomplished. Sorting according to the various techniques discussed earlier may then be accomplished from which sperm cells may be recovered in the collection phase.

An optimal number of motile spermatozoa per insemination dose to maximize fertility with prior techniques has perhaps been well established in species such as swine, sheep, and cattle. With the present invention, the minimum number of motile spermatozoa seem to be much less than the 250 to $500 \times 10^6$ progressively motile spermatozoa (pms) usually recommended. Under ideal conditions, mares had even been inseminated with as few as $100 \times 10^6$ pms without reducing fertility. (Researches found no difference between mares inseminated over three cycles with 100 or $500 \times 10^6$ pms and achieved pregnancy rates of 63.9 and 75%, respectively.) The present invention shows even lower numbers now to be possible—and that the lower numbers can be achieved in a field environment.

Although the difference was not significant, in one experiment pregnancy rates for the 100 and $500 \times 10^6$ treatments for cycles 1, 2, and 3 were 25 vs. 39, 33 vs. 45, and 28 vs. 25% respectively. Notably, others have reported an increase in foaling rate when the number of motile spermatozoa per insemination was increased from 40 to $80 \times 10^6$, but no further improvement was observed when the number of spermatozoa was increased to $160 \times 10^6$. In an experiment using two groups of 14 subfertile mares, one researcher found no difference between treatments utilizing 100 or $500 \times 10^6$ motile spermatozoa per insemination (35.7 vs. 42.9%, respectively). Later, the same researcher reported pregnancy rates after breeding over three cycles from mares inseminated with 50, 100, and $500 \times 10^6$ pms of 41.7, 65.6, and 81.3%, respectively, from data averaged from several experiments. Yet another in the art inseminated mares (over three cycles) with 50 and $500 \times 10^6$ pms and found a significant difference between pregnancy rates of 37.5 and 75%, respectively. In a more recent study, one of the inventors superovulated mares with equine pituitary extract (EPE) and inseminated mares one time with $50 \times 10^6$ pms. Pregnancy rates were not different between the mares treated with EPE and the saline controls (65 and 55%, respectively).

In existing routine equine artificial insemination, though there appears to be little difference in fertility between 100 and $500 \times 10^6$ spermatozoa per insemination dose, $500 \times 10^6$ pms is generally recommended to provide maximum fertility. However, when proper artificial insemination techniques were utilized, $100 \times 10^6$ pms from a highly fertile stallion was also believed to be the minimum adequate with the prior techniques. In the more accepted circumstance, when performing routine artificial insemination (AI) with fertile stallions and mares, $500 \times 10^6$ progressively motile sperm/dose inseminated every other day while mares are in estrus has been reported to result in maximum fertility. As alluded to earlier, the problem with this is simple, insemination of mares with a low number of spermatozoa may be necessary when semen is limited or when using sorted sexed semen.

As mentioned earlier, currently, it is possible to obtain approximately 1000 equine live sperm/second ($3.6 \times 10^6$/hr) of each sex chromosomal composition when sorting spermatozoa for sex chromosomes by flow cytometry at 90% accuracy. Thus it would be impractical to obtain $500 \times 10^6$ sperm that were sorted for sex chromosomes for an insemination at $3.6 \times 10^6$ sperm/hour. The goal therefore, was to achieve lesser numbers of spermatozoa per insemination dose while obtaining reasonable fertility. The objective was to achieve pregnancy rates in mares inseminated on a single occasion, close to ovulation, with as low as 25 or $5 \times 10^6$ or lower progressively motile spermatozoa (pms).

The normal stallion ejaculate contains an average volume of 50 ml. The stallion deposits this high volume of semen directly into the uterus of the female. In another species (boar) which ejaculates several hundred ml of semen, only 0.5-0.1 ml enters each fallopian tube at the beginning of estrus to permit fertilization. This large seminal volume fills the region of the utero-tubal junction until a reservoir of spermatozoa is established in the isthmus. Therefore a specific volume of semen is established in the isthmus and the remaining content is rapidly eliminated.

For artificial insemination, the number of spermatozoa in an insemination dose can be critical. Seminal extenders are often used to dilute raw semen to provide larger and more easily managed insemination volumes. In the prior art, volume ranging between 10 and 25 ml of semen is generally recommended although, now, perhaps depending on the concentration of spermatozoa, small insemination volumes can prove to be as effective as larger volumes. Although the concentration was not specified, insemination volumes ranging from 0.6-26.8 ml of semen did not adversely affect fertility when the effects of inseminating 10 or 50 ml volumes of extended semen on embryo recovery rates were studied in mares. But based on this experiment, there was a reduction in embryo recovery rates from mares inseminated with a 50 ml volume of extended semen compared to a 10 ml volume when both contained an equal number of pms. The reduced fertility may have been due to the increased volume inseminated or could have been due to the decreased spermatozoa concentration since it was $\frac{1}{5}^{th}$ that of the 10 ml volume (5 vs. $25 \times 10^6$).

Further experiments were conducted to determine: 1) embryo recovery rate when mares were inseminated with $100 \times 10^6$ pms extended in 10, 100, or 200 ml of dried skim milk extender and 2) embryo recovery rate when mares were inseminated with $250 \times 10^6$ pms extended either 10 or 100 ml of the same extender as experiment 1. Results from experiment 1 showed a difference in embryos recovered only between mares inseminated with 10 (40%) and 200 ml (0%). In one of those experiments there was a significant difference between mares inseminated with 10 ml (70.6%) compared to 100 ml (13%). Thus, insemination volumes of 100 or 200 ml were associated with lower embryo recovery rates than a 10 ml volume, probably due to the lower sperm concentration or retrograde loss of sperm into the vagina.

They conducted a study to test whether volume alone affects fertility when sufficient concentrations and numbers of spermatozoa are present. They concluded that there was no difference between mares inseminated with either 30 or 120 ml of cooled semen at a concentration of $50 \times 10^6$ pms/ml. This approach, however, is not followed by the present invention to some degree.

Timing and frequency of insemination can play a very important role in most breeding operations, especially when frozen or shipped-cooled semen is involved. The number and timing of insemination can affect fertility. The average mare ovulates every 21 days during the physiological breeding season, and the average duration of estrus during this time is 5-7 days. During estrus, mares will passively urinate, lift their tail, and present their hindquarters to the stallion. Under natural conditions when a stallion was introduced to a herd of 20 mares, the number of breeding per hour of observation was 2.4±0.2. Stallions often breed the same mare multiple times per day (under natural conditions). In one study, 20 mares were synchronized and placed in a pasture with a stallion and observed for 9 days. The stallion mated 9.12 times per day and settled 17 of 18 mares.

Researchers have also compiled data over multiple breeding seasons comparing the effect of the number of inseminations on pregnancy rates. More mares became pregnant when inseminated five times (68%) more than mares that were inseminated three times (35.9%) during cycle 1. No other differences were noted in regard to number of inseminations on pregnancy rates during cycle 1. There was no difference in pregnancy rates during cycles 2 and 3 when mares were inseminated one to seven times. More mares became pregnant when inseminated 5 times (60%) than mares inseminated 1 (23.5%), 2 (35%), or 3 times (35.5%) over 3 cycles. When considering all 3 cycles, mares that became pregnant were inseminated an average of 3.3 times, which was more than the average of 2.8 times for mares not becoming pregnant.

It has also been determined that multiple inseminations per cycle were not detrimental to fertility. In one study, data were collected from 257 mares over a 10-year period to establish the relationship between the number of inseminations per cycle, duration of estrus and pregnancy rates. Mares were inseminated with $100 \times 10^6$ spermatozoa. First cycle pregnancy rates of 22.0 23.0, 38.6, 52.5, 58.3, and 52.2% were achieved when mares were inseminated 1, 2, 3, 4, 5, or 6 or more times per cycle, respectively. Fewer mares became pregnant after three cycles when inseminated 1-4 times per cycle than mares inseminated $\geq 12$ times per cycle. Another study inseminated 62 mares over three cycles every 48 hours during estrus with $200 \times 10^6$ pms for a maximum of three inseminations. Inseminations began when a follicle $\geq 30$ mm was detected and continued until ovulation. Fertility per cycle was 45% and was not different if two or more inseminations were done per cycle as compared to one insemination per cycle. They also determined that the highest pregnancy rates were achieved with inseminations performed between 48 and 72 (8/23) or 72 and 96 hours (8/23) before ovulation and that the last insemination was not the fertilizing one at least 51% of the time. Overall, when performing routine AI with fertile stallions and mares, $500 \times 10^6$ pms/dose inseminated every other day while mares are in estrus results in maximum fertility. With the present invention, much lower numbers are now possible.

Induction of ovulation at a specific time in the mare may be advantageous for the following reasons: to ensure that ovulation will occur within 36-48 hours of mating eliminating the need for rebreeding, (b) with use of cooled, frozen or sexed semen when timing is critical in order to maximize fertility, (c) to ensure that only a single insemination close to ovulation is needed when utilizing subfertile stallions or mares, (d) to minimize mare or stallion transport, and (e) to stagger ovulations when multiple mares are presented in estrus at the same time.

Human chorionic gonadotropin (hCG) is produced by the cytotrophoblast of the chorionic villi of the human placenta. It is a glycoprotein hormone composed of two subunits (α and β) which are linked together non-covalently. It has a half-life of 8-12 hours in blood.

Use of hCG for induction of ovulation during the estrous cycle of the mare was first reported in 1937 by Mirskaja and Petropavlovski. They found that ovulation occurred within 24 to 48 hours after injection of crude extract of human pregnancy urine (Prolan®) injected on the first day of estrous. Further studies have shown that when hCG (1500-3300 IU) is injected in a mare during early estrus, it mimics lutenizing hormone (LH) activity and induces ovulation, generally within 24-48 hours. The use of hCG at a dose of 2000-3000 IU has not decreased fertility. However, some researchers did find that higher doses (4500-6000 IU) resulted in reproductive disorders and a decreased pregnancy rate. Although the use of hCG can be very effective in inducing ovulation, several researchers have shown that administration of hCG over several consecutive estrous cycles can result in antibody formation, with mean duration of estrus and ovulation either the same as the control mares or 2 days longer than controls.

Native gonadotropin releasing hormone (GnRH) is a decapeptide synthesized in the hypothalamus and stored in secretory granules of the median eminence. Upon release, GnRH enters the portal system and is transported to the anterior pituitary and binds to receptors on gonadotrope cells where it stimulates synthesis and secretion of lutenizing hormone (LH) and follicle stimulating hormone (FSH). Research has also been conducted on the use of native GnRH and GnRH analogues in which 1 or 2 amino acids have been modified on inducing ovulation during estrus in the mare.

Pulsatile or continuous administration of native GnRH causes predictable ovulation. In one study 11 cycling mares were infused with either saline or 20 μg GnRH in a pulsatile pattern (one 5-sec. pulse/hr, 2 h or 4 h) starting on day 16 of the estrous cycle. The number of days from start of treatment to ovulation was less in mares infused with 20 μg GnRH/hr compared to saline control mares or 20 μg GnRH per 4 hr. It was concluded that pulsatile infusion of GnRH is effective in advancing ovulation, but the frequency of the pulse is a critical variable. Native GnRH has also been used to induce follicular development and ovulation in seasonally anestrous mares. A short term implant which releases 1.5 or 2.2 mg of the GnRH analogue deslorelin causes ovulation within 36-48 hours when administered to mares in estrus with a follicle >30 mm in diameter.

One of the inventors has compared the effect of various doses of a GnRH analog (deslorelin acetate) implant, on induction of ovulation in cyclic mares and found that ovulation was induced in most mares within 48 hr after injection and there is no advantage of doses higher than 2.2 mg/mare. Others have compared the use of hCG, buserelin (a GnRH analog) and luprostiol (a $PGF_2\alpha$ analog) for induction of ovulation in cycling mares. Both buserelin and hCG shortened the interval from treatment to ovulation, whereas luprostiol failed to hasten ovulation.

Equine pituitary extract (EPE) is derived from equine anterior pituitary glands. Preparation of EPE for experimentation as a crude gonadotropin has been described by Braselton and McShan (1970), and more recently by Guillou and Combarnous (1983), each hereby incorporated by reference. EPE has been used in the mare primarily to induce growth of multiple follicles in cyclic or anestrous mares and for superovulation in the ewe.

Use of equine pituitary extract as an ovulatory agent in the mare has been known. In studies, some have separated equine luteinizing hormone (eLH) and follicle stimulating hormone (eFSH) by hydrophobic interaction chromatography (HIC) and conducted experiments. In one experiment, LH activity in crude equine gonadotropin (CEG) was compared to LH activity in the HIC fraction on its ability to induce ovulation. Of 25 control mares, 7 ovulated within 48 h compared with 24/25 mares treated with CEG and 19/26 mares treated with LH. Another experiment was designed to test the ability of the eFSH-enriched fraction of pituitary extract to induce the growth of multiple follicles compared to CEG. The number of follicles that reached 30 mm was the same in CEG vs. FSH treated groups and both groups were different when compared to the control group. Ovulation rates were not different between the two treatment groups but were different from the control group.

Historically, the most commonly used method of inducing ovulation is a single injection of hCG. This still remains the most common method. However, since there is no difference in pregnancy rates or timing of ovulation when administering either GnRH or hCG to cycling mares, either treatment is an acceptable method for inducing ovulation. EPE however, is not commercially available to practitioners and therefore is not a practical technique for inducing ovulation.

Under natural mating conditions, the equine ejaculate is deposited directly into uterus of the mare. Spallanzani was first to report artificial insemination (AI) in dogs, and then horses in the late 1700s. The use of AI has been documented in cattle, sheep, swine, and horses. Horses, cattle, and hogs are artificially inseminated within the uterine body; sheep, goats and dogs in the cervix; and cats in the anterior vagina. As to equines, others have described routine seminal collection and handling procedures in the horse. For routine AI procedures, semen is deposited within the uterine body using a sterile insemination pipette and syringe. However, there are several reasons for the use of alternative sites and techniques for artificial insemination: a) insemination of frozen thawed semen of low quality or limited quantity, b) insemination of semen from a subfertile sire or c) insemination with sexed semen, which is of limited quantity. Some alternative AI techniques include: intra-uterine insemination (via laparoscopy or nonsurgical techniques) in those species where cervical or vaginal inseminations are routinely performed, oviductal insemination (via laparoscopy or flank laparotomy), or deep intra-uterine nonsurgical insemination.

Laparoscopic intra-uterine insemination has evolved as the least invasive technique for depositing semen directly into the uterus of sheep and goats since the early 1970's when suitable equipment was developed. Laparoscopic insemination is routinely performed in the ewe and goat with high fertility compared to traditional AI. Laparoscopic intra-uterine insemination has also been successfully reported in the ferret, domestic cat, tiger, cheetah and leopard, and most recently the possum and wallaby. Some advantages of laparoscopic insemination include: genetic improvement utilizing frozen semen, increased number of inseminations per collection using lower sperm numbers, and higher fertility. The main disadvantage of laparoscopic insemination is the higher cost of the equipment and procedure (skilled labor, drugs, semen processing). This procedure is also relatively invasive to the patient.

Nonsurgical intra-uterine insemination with ewes is used in an attempt to increase fertility rates in species that are routinely inseminated in the cervix. One researcher obtained a 75% lambing rate following intra-uterine insemination, compared to 17% after deep cervical insemination, and 30% after double caudocervical insemination. In another study, a researcher deposited frozen-thawed ram sperm into three regions of the genital tract of ewes. In group 1, a single intra-uterine insemination was performed, while in group 2, ewes were inseminated once deep in the cervix, and in group 3, ewes were inseminated twice, 12 hours apart, in the caudocervical region; conception rates were 89, 45, and 57% respectively. Others reported similar results with intra-uterine insemination. Nonsurgical endoscopic insemination has also been performed in bitches resulting in high pregnancy rates.

With oviductal insemination (OI) a small volume of semen (usually 0.05-0.5 ml) is surgically inseminated into the oviductal lumen. One study inseminated nine gilts using laparoscopic insemination. Two of the nine (22%) gilts became pregnant from a single insemination. A more recent study in the ewe, determined the effects of number of spermatozoa, timing and site of insemination on fertility. In experiment 1, ewes were inseminated with $10^4$, $10^5$, $10^6$ or $10^7$ spermatozoa. Ova recovered 48 hours later were classified as fertilized if they had cleaved. Results showed that more ewes were fertile after oviductal than after intrauterine insemination (61 vs. 39%) and with high ($10^6$ and $10^7$) rather than low ($10^4$ and $10^5$) doses of spermatozoa for intra-uterine but not for oviductal inseminations. Researchers at our facility have achieved for the first time, the use of OI to obtain pregnancies in the mare. Fourteen mares were inseminated by OI with $50 \times 10^3$ pms and 15 were inseminated by intrauterine AI with $500 \times 10^6$ pms. Pregnancy rates were not different between groups 3/14 (21.4%) and 6/15 (40%), respectively. Oviductal insemination has also been successfully used to obtain pregnancies in women and rabbits.

In cows, the site of seminal deposition during artificial insemination for the past four decades has been the uterine body. This is an acceptable technique when high numbers of fertile spermatozoa are available for insemination, but for equines—especially when limited numbers of sperm are available—an alternative approach has been developed. Deep intrauterine insemination is a technique that has been used to obtain pregnancies in cattle. One study compared pregnancy rates to AI when semen was deposited into the uterine body or into both uterine horns (cornual insemination). Pregnancy rates when semen was deposited into the uterine body were 44.7% compared to 64.6% with cornual insemination. However, not all studies show an advantage with this technique of insemination.

As this invention shows, there can be a congruence of methods of sexing sperm based on DNA content, high speed flow cytometer/cell sorters, and procedures for inseminating equines with fewer than twenty-five million total sperm without compromising fertility which may result in the possibility of a viable non-surgical or even sexed semen industry in equines. Interestingly, rather than inseminating within the uterine body where such insemination are usually placed, by insemination deep within the mare's uterine horn, better results may be achieved. By deep, it should be understood that the insertion is placed well into the uterine horn. It may, but does not need to be done using the embryo transfer equipment.

As a result of the insemination, it is of course desired that an animal of the desired sex be produced. This animal may be produced according to the systems discussed earlier through the use of the sexed sperm specimen. It should also be understood that the techniques of the present invention may find application in other techniques such as laproscopic insemination, oviductal insemination, or the like. As examples, the following experiments have been conducted. While not all use every aspect of the inventions described here, and do not show all the performance enhancements of the invention, they do show some enhancements possible through differing aspects of the invention.

Mares—Sixty-one reproductively normal cycling mares of light horse breeds, ranging in age from 3 to 15 were used. Mares were administered cloprostenol (250 µl i.m.) to induce luteolysis and examined by palpation and ultrasonography of the reproductive tract per rectum, every other day until a follicle >30 mm was detected, and then daily until ovulation. Once a mare developed a follicle ≧35 mm, a gonadotropin releasing hormone (GnRH) implant (deslorelin acetate 2.2 mg, Ovuplant®, Fort Dodge, Iowa) was administered subcutaneously, and she was assigned to 1 of 3 treatment groups.

Treatment Group 1—Mares were inseminated on a single occasion with $500 \times 10^6$ pms in a volume of 20 ml ($25 \times 10^6$ pms/ml), either 40 hr (n=9) or 34 hr (n=11) after GnRH administration. Semen was deposited into the uterine body using a flexible plastic artificial insemination (AI) pipette (IMV, France).

Treatment Group 2—Mares were inseminated on a single occasion with $25\times10^6$ pms in a volume of 1 ml ($25\times10^6$ pms/ml), either 40 hr (n=13) or 34 hr (n=8) after GnRH administration. Semen was deposited at the tip of the uterine horn, ipsilateral to the preovulatory follicle, using a flexible plastic AI pipette. The location of pipette within the uterus was confirmed by transrectal ultrasonography prior to semen deposition.

Treatment Group 3—Mares were inseminated on a single occasion with $5\times10^6$ pms in a volume of either 1 ml ($5\times10^6$ pms/ml), 40 hr (n=10) or 0.2 ml ($25\times10^6$ pms/ml), 34 hr (n=10) after GnRH administration. Mares receiving 1 ml were inseminated with a flexible plastic AI pipette, while mares receiving 0.2 ml were inseminated using a disposable implant gun (Veterinary Concepts, Green Valley, Wis.) containing a 0.5 ml plastic straw. Different insemination pipettes were used to optimize delivery of the two different volumes. Semen was deposited at the tip of the uterine horn, ipsilateral to the preovulatory follicle. The location of pipettes within the uterus was confirmed by transrectal ultrasonography prior to semen deposition.

After insemination, mares were examined daily to determine the day of ovulation. Pregnancy exams were performed by ultrasonography on days 12, 14, and 16 post-ovulation. Pregnancy rates were not different between two Arabian breeding stallions (Stallion A=22/31, 71%; Stallion B=15/30, 50%) O, or between mares bred 34 vs. 40 hours after GnRH administration (19/29, 65% and 18/32, 56%, respectively) (P>0.1), so the data sets were combined. As shown in Table 1, mares bred with $500\times10^6$ pms in a 20 ml volume had a significantly higher (P<0.05) pregnancy rate than mares bred with 25 or $5\times10^6$ pms (Table 1). There was no significant difference (P>0.05) in pregnancy rates between mares bred with $25\times10^6$ pms and mares bred with $5\times10^6$ pms in a volume of 1 or 0.2 mls. Although fertility was significantly higher with $500\times10^6$ pms when compared to Group 2 ($25\times10^6$ pms), an initial rate of 57% was achieved with a single insemination. This was not different than pregnancy rates achieved with Group 3 ($5\times10^6$ pms), 7/20 (35%).

TABLE 1

Pregnancy Rates from a Single Insemination

| No. Progressively Motile Sperm | % Pregnant at Day 16 |
|---|---|
| $500\times10^6$ in 20 ml | 18/20 (90%)[a] |
| $25\times10^6$ in 1 ml | 12/21 (57%)[b] |
| $5\times10^6$ in 1 ml | 3/10 (30%)[b] |
| $5\times10^6$ in 0.2 ml | 4/10 (40%)[b] |

[a,b]Values with different superscripts differ (P < 0.05) (Chi square)

The timing of insemination relative to GnRH administration was changed from 40 to 34 hr post GnRH during the experiment because many mares were ovulating prior to planned insemination, and therefore were not inseminated. Data from 22 mare cycles (26.5%) were excluded because they either ovulated prior to planned insemination (n=11), did not ovulate (n=3), or ovulated >4 days after GnRH administration (n=8).

The optimal number of sperm generally recommended per insemination dose is $500\times10^6$ pms every other day while the mare is in estrus. However, as mentioned earlier, there have been studies that have shown no decrease in fertility when inseminating with $100\times10^6$ compared to $500\times10^6$ motile sperm. Studies with $50\times10^6$ motile sperm have shown a decrease in fertility when compared to 100 and $500\times10^6$. Other studies have shown that as the number of inseminations increases, fertility increases. Unfortunately, results from these studies have been somewhat inconsistent. Therefore the present invention is directed toward achieving the lowest number of sperm required to provide reasonable pregnancy rates when administered on a single occasion, close to ovulation.

In Group 3, 20 mares were inseminated with $5\times10^6$ pms in a volume of either 1 ml ($5\times10^6$ pms/ml) (n=10), or a volume of 0.2 ml ($25\times10^6$ pms/ml) (n=10). Pregnancy rates between the two sub-groups were compared because pregnancy rates have been reported to decrease when diluting semen to a sperm concentration of $<25\times10^6$/ml. However, in this experiment there was no difference in fertility between the two sperm concentrations.

If a mare had already ovulated based on rectal palpation and ultrasound examination the morning of the day of planned insemination, she was not inseminated. Instead, cloprostenol (250 µg) was administered 5 days post ovulation to induce luteolysis so she could be reused. Pregnancies were terminated at day-16 by locating by transrectal ultrasonography and disruption of the embryonic vesicle. Cloprostenol (250 µg, i.m.) was then administered to induce luteolysis so they could be reused.

Semen was deposited at the tip of the uterine horn for the two lower doses in this experiment. Seminal deposition deep into the uterine horn is particularly useful when using low sperm numbers in a low volume. The flexible insemination pipette was placed in the uterus per vagina and then slowly guided to the tip of the desired uterine horn by gentle manipulation per rectum. The location of the pipette was confirmed by transrectal palpation and ultrasound examination.

An additional small, study was conducted at the end of the breeding season using five mares and one of the same two stallions. The objective of the study was to determine pregnancy rates with $25\times10^6$ pms deposited in the uterine body. Three of five mares (60%) inseminated on a single occasion with $25\times10^6$ pms 40 hr post GnRH administration were pregnant at 16 d.

In summary, the results of these experiments showed that a day-16 pregnancy rate of 57% was achieved with a single insemination, close to ovulation, With $25\times10^6$ pms when deposited deep into the uterine horn.

The objectives of the following experiments were to 1) determine pregnancy rates following insemination with $25\times10^6$ live-sorted, sexed spermatozoa deposited at the tip of the uterine horn ipsilateral to the preovulatory follicle and 2) compare pregnancy rates for semen sorted into a skim milk extender with or without egg-yolk.

Mares—Seventeen reproductively normal cycling mares of light horse breeds, ranging from 5 to 12 years of age were used. Mares were administered cloprostenol (250 µg i.m.) to induce luteolysis and examined by palpation and ultrasonography of the reproductive tract per rectum every other day until a follicle >30 mm was detected, and then every day until ovulation. Once a mare developed a follicle ≧35 mm, she was administered a gonadotropin releasing hormone (GnRH) implant (deslorelin acetate 2.2 mg, Ovuplant®, Fort Dodge, Iowa) subcutaneously, and randomly assigned to 1 of 2 treatment groups.

Treatment Group A—Mares (n=11) were inseminated on a single occasion with ~$25\times10^6$ live-sorted spermatozoa in a volume of 1 ml (25 million/ml), 34 hr after GnRH administration. Spermatozoa were sorted into a commercial skim milk semen extender (EZ-Mixin, OF, Animal Reproduction Systems, Chino, Calif.), and the same extender was added after centrifugation as a post-centrifuge buffer to adjust sperm concentration to 25×10⁶ ml. Sperm was deposited at the tip of the uterine horn, ipsilateral to the preovulatory follicle, using a flexible plastic AI pipette (IMV, France). The location of pipette within the uterus was confirmed by transrectal ultrasonography prior to semen deposition. One mare was inseminated with 20×10⁶ live-sorted spermatozoa because of time constraints with the flow cytometer. One mare failed to ovulate and was excluded from the study.

Treatment Group B—Mares (n=10) were inseminated on a single occasion with ~25×10⁶ live-sorted spermatozoa in a volume of 1 ml (25 million/ml), 34 hr after GnRH administration. One mare was inseminated with 20×10⁶ live-sorted spermatozoa because of time constraints with the flow cytometer. Spermatozoa were sorted into the same commercial semen extender plus 4% egg-yolk, and the same extender was added after centrifugation as a post-centrifuge buffer to adjust sperm concentration. Sperm were deposited at the tip of the uterine horn, ipsilateral to the preovulatory follicle using a flexible plastic AI pipette. The location of pipette within the uterus was confirmed by transrectal ultrasonography prior to semen deposition.

After insemination, mares were examined on a daily basis to determine the day of ovulation. Pregnancy exams were performed by ultrasonography on days 12, 14, 16, and 30 and post-ovulation, and fetuses were sexed on day 60.

Semen Collection and Preparation—Two stallions of Arabian breeding and known, high fertility were used in this experiment, one of which (Stallion A) was used in Experiment 1. Semen was collected the morning of planned insemination with a Colorado model artificial vagina (Animal Reproduction Systems, Chino, Calif.) equipped with an in-line gel filter. Ejaculates were evaluated for gel free-volume, motility and spermatozoal concentration. Semen was extended 1:1 in HBGM-3 with BSA and within minutes, transported at ambient temperature to the laboratory for further processing. The semen was centrifuged for 10 minutes at 400×g at 22° C. to highly concentrate the sperm. After centrifugation, the supernatant was aspirated, leaving a soft sperm pellet. The concentration of spermatozoa was determined using a densimeter (Animal Reproduction Systems, Chino, Calif.) and spermatozoa were subsequently diluted to 400×10⁶/ml in HBGM-3 in a total volume of 1 ml, and stained with 25 µl Hoechst 33342 (5 mg/ml water). A total of eight sample tubes were prepared and incubated at 34° C. for 1 hour. Next, the stained samples were diluted to 100×10⁶/ml with 3 ml of HBGM-3. Food coloring (2 µl/ml of 1% FD&C #40 in HBGM-3) was added to each of the eight sample tubes, resulting in a 4 ml total volume. The samples were then filtered through a 1 ml, 40 micron filter apparatus into 6 ml polypropylene tubes and held at ambient temperature until approximately 25×10⁶ live spermatozoa were sorted for DNA by flow cytometry. An argon laser, emitting 150 mW at 351 and 364 nm, was used on each of two MoFlo® flow cytometer/cell sorters modified for sperm sorting, operating at 50 psi with HBGM-3 without BSA as sheath fluid. Spermatozoa were collected at approximately 900 live sperm/sec into a total of 6 polypropylene tubes (14 mls each) which contained 4 ml catch fluid before the start of sorting of either EZ-Mixin® or 4% egg-yolk in EZ-Mixin®. When two mares were available for insemination on the same day, both X- and Y-chromosome enriched sperm were collected. Tube contents were mixed every 30 minutes during sorting. After sorting, sperm were pooled together from the two flow cytometers, placed in 50 ml centrifuge tubes and centrifuged for 20 minutes at 1200×g at 22° C. The supernatant was then aspirated down to a 200 µl sperm pellet, and 100 µl of post-centrifuge buffer of either EZ-Mixin® CST (Animal Reproduction Systems, Chino Calif.) or 4% skim milk-egg yolk was added to the pellet and transferred to a 50 ml preweighted Falcon tube. A hemacytometer count was done to determine final sperm concentration/ml. The volume of sperm in the Falcon tube×sperm concentration/ml equalled the total number of sperm recovered. Samples were then diluted to a total of 25×10⁶ live sorted spermatozoa in a volume of 1 ml which was used for insemination.

Reanalysis of Sperm for DNA Content—The relative DNA content of the sorted intact sperm used for insemination was determined by flow cytometric analysis of sperm nuclei from a sample containing <0.5 ml of each of the respective batches collected at the end of the day. Sperm nuclei were prepared from an aliquot of intact sorted sperm by sonication for 3 seconds with an Ultrasonic Dismembrator 60 (Fisher Scientific) set at setting #2 (approximately 1 watt). The proportion of X- and Y-bearing sperm was determined by fitting a pair of Gaussian distributions to the histograms from the 0° detector (Johnson et al., 1987b). Reanalysis for DNA indicated an average sort purity of 90% for X and 84% for Y chromosome bearing sperm for the 17 sorts.

Fetal Sex Determination—Fetuses from mares pregnant 60-70 days post-ovulation were sexed via transrectal ultrasonography without knowledge of the sex of the sorted sperm inseminated. A real-time ultrasound scanner (Aloka 500®) equipped with a linear-array 5-Mhz transducer was used for sex determination. Fetal gender can be accurately (up to 99%) determined in horses and cattle by identifying and locating the genital tubercle (Curran, 1998).

Statistical Analysis—Data were analyzed using Fishers Exact Test

Pregnancy rates at day 16 are shown in Table 2. Pregnancy rates were not different between stallions (Stallion A=3/10, 30%; Stallion B=5/10, 50%) (P>0.1), so the data sets were combined. There was no statistical difference in pregnancy rates between sperm treatments (EZ-Mixin=3/10, 30%, vs. 4% EY+EZ-Mixin=5/10, 50%) (P>0.1) although this result may not always be true. The phenotypic sex ratio was predicted with perfect accuracy, five out of five.

Three mares lost their pregnancy sometime between 16-60 days post-ovulation, so fetal sex could not be determined. One mare inseminated with X-bearing spermatozoa was euthanized at day 66 of gestation due to a gastro-intestinal problem. A phenotypically normal female fetus (the correct sex) was detected at necropsy.

TABLE 2

Pregnancy Rates Following Insemination With 25 × 10⁶ Sexed Spermatozoa

| Treatment Group | No. Mares Inseminated | No. Mares Pregnant at 16 d | No. Mares Pregnant at 60 d | Predicted* % ♂ | ♀ | Actual ♂ | ♀ |
|---|---|---|---|---|---|---|---|
| EZ-Mixin | 10 | 3ᵃ | 1 | 78 | 89 | ** | 1/1 |
| 4% EY + EZ-Mixin | 10 | 5ᵃ | 4 | 84 | 87 | 3/3 | 1/1 |

ᵃNo significant difference (P > 0.1).
*Results of reanalysis for relative DNA content of aliquots of sorted X- and Y-bearing sperm populations.
**Lost pregnancy prior to sex determination

RESULTS

Many attempts have been made during the past 80 years to separate X- and Y-chromosome bearing sperm. The only non-destructive method that has a proven record of accurately identifying X and Y chromosome-bearing sperm is flow cytometry/cell sorting, thus making it possible to alter the sex ratio as desired. Sperm have been separated by flow cytometry/cell sorting to obtain pregnancy following surgical insemination in the following species: rabbits, swine, and horses. Surgical insemination was chosen in these experiments because of the necessity for minimizing sperm numbers due to the slow flow sorting rate (~100 sperm/sec) of X- and Y-bearing sperm and the apparent need for large numbers of sperm to establish a pregnancy. Production of X- and Y-bearing sperm per unit time by means of high speed sorting and a newly developed orienting nozzle has increased sorting rates to 10-12 times that of previous rates. This technology has increased the number of sorted sperm per unit time and has enabled researchers to obtain pregnancies resulting from non-surgical, intra-uterine insemination in sheep and cattle.

The present study was the first to obtain viable pregnancies in the horse following non-surgical, intra-uterine insemination with sexed semen. The pregnancy rate at day 16 following insemination of $25 \times 10^6$ sexed spermatozoa (40%), was not statistically different (P>0.1) than that of mares in Experiment 1 inseminated with $25 \times 10^6$ non-sorted, progressively motile spermatozoa (57%). The insemination technique was the same in both experiments. The same mares and technicians were used in both experiments. Also, both experiments were conducted during the same breeding season, at the same time of year.

Initial experimental pregnancy rates were slightly lower with sexed semen probably because of the amount of time it takes to sort $25 \times 10^6$ sperm and possible damage to the sperm by the process. In the experiments, the average time from semen collection to insemination was 7 hours. In the first experiment, mares were inseminated almost immediately after semen collection. The average total and progressive motility for the sexed spermatozoa was 69 and 38% respectively, and a total of only $25 \times 10^6$ live-sorted sperm cells were collected for insemination. The sorting process is a very stressful procedure to sperm. Sperm are pumped through fine tubing at high pressure which causes them to exit at ~100 km/hr, and stored at ambient temperature for hours until adequate numbers of sperm are collected. Sperm are incubated for one hour at 35° C. with Hoechst 33342, which has a high affinity for AT-rich regions of DNA and then exposed to ultraviolet laser light at 351 and 364 mn. Unlike many DNA-specific stains, Hoechst 33342 does not intercalate into the DNA helix. While none of these processes is conducive to sperm health, no increased incidence of genetic abnormalities has been reported in the hundreds of offspring that have been produced utilizing this technology.

Of ancillary interest is the fact that others have proposed another possible explanation for lower pregnancy rates with sexed semen. They found that the first cell cycle was delayed in rabbit embryos fertilized by sperm treated with Hoechst 33342. Unfortunately, the mechanism is not known, but could be due to interference of the dye molecules as DNA is replicated or transcribed. Decreased embryo survival also has been documented in flow-sorted sperm.

Three of eight mares (38%) inseminated with sexed semen lost their pregnancies between 16-60 days. Two of these mares developed embryonic vesicles which appeared normal until day 16. The vesicles then decreased in size until they were no longer present. One of the three mares developed a viable pregnancy with a visible fetus and a heartbeat. The fetus was observed to be alive at day 35, but was lost by day 50. With fresh, non-sorted semen, early embryonic loss has been found to be 9% by day 14 and up to 16% on average between days 20 and 50. A sperm staining and sorting procedure was used in the present experiments. It is possible that equine sperm are more sensitive to the staining and sorting procedures than bovine sperm.

In summary, this invention has demonstrated for the first time, that pregnancy in the mare can be achieved, and foals of predetermined sex can be obtained, by deposition of a low number of spermatozoa at the tip of the uterine horn of the mare. Sexing mammalian sperm is moving away from a research technique and may now be available for commercial equine AI programs. Further, as mentioned and as can be seen from the various experiments, the field is statistically based and thus a variety of additional experiments may be conducted to further evidence the appropriate combination and limitation strategies.

The discussion included in this application is intended to serve as a basic description. The reader should be aware that the specific discussion may not explicitly describe all embodiments possible; many alternatives are implicit. It also may not fully explain the generic nature of the invention and may not explicitly show how each feature or element can actually be representative of a broader function or of a great variety of alternative or equivalent elements. Again, these are implicitly included in this disclosure. Where the invention is described in device-oriented terminology, each element of the device implicitly performs a function. Apparatus claims may not only be included for the device described, but also method or process claims may be included to address the functions the invention and each element performs. Neither the description nor the terminology is intended to limit the scope of the claims which may be submitted. It should be understood that a variety of changes may be made without departing from the essence of the invention. Such changes are also implicitly included in the description. They still fall within the scope of this invention. A broad disclosure encompassing both the explicit embodiment(s) shown, the great variety of implicit alternative embodiments, and the broad methods or processes and the like are encompassed by this disclosure.

In addition, each of the various elements of the invention and claims may also be achieved in a variety of manners. This disclosure should be understood to encompass each such variation, be it a variation of an embodiment of any apparatus embodiment, a method or process embodiment, or even merely a variation of any element of these. Particularly, it should be understood that as the disclosure relates to elements of the invention, the words for each element may be expressed by equivalent apparatus terms or method terms—even if only the function or result is the same. Such equivalent, broader, or even more generic terms should be considered to be encompassed in the description of each element or action. Such terms can be substituted where desired to make explicit the implicitly broad coverage to which this invention is entitled. As but one example, it should be understood that all actions may be expressed as a means for taking that action or as an element which causes that action. Similarly, each physical element disclosed should be understood to encompass a disclosure of the action which that physical element facilitates. As but one example of this aspect, the disclosure of a "collector" should be understood to encompass disclosure of the act of "collecting"—whether explicitly discussed or not—and, conversely, were there only disclosure of the act of "collecting", such a disclosure should be understood to encompass disclosure of a "collector." Such changes and alternative terms are to be understood to be explicitly included in the description. Further, it should be understood that in addition to the claims initially presented, the claims may be varied to more expansively address variations of each of these devices and methods set forth, each feature, component, and step shown as separate and independent inventions, and the various combinations and permutations of each of the above.

Finally, throughout this specification—especially the claims—unless the context requires otherwise, the word "comprise" or variations such as "comprises" or "comprising", will be understood to imply the inclusion of a stated element or group of elements but not the exclusion of any other element or group of elements.

The invention claimed is:

1. A method of establishing an equine artificial insemination sample for equine artificial insemination comprising the steps of:
   a. obtaining equine sperm cells from a male of a species of equine mammal;
   b. staining said equine sperm cells to allow differentiation based upon a sex characteristic;
   c. establishing a cell source which introduces said equine sperm cells which have been stained into a sheath fluid;
   d. forming droplets in said sheath fluid;
   e. entraining said equine sperm cells which have been stained in said droplets;
   f. differentiating between said equine sperm cells entrained in said droplets based upon said sex characteristic;
   g. separating said droplets based upon said sex characteristic of said equine sperm cells entrained at a rate of at least nine hundred live equine sperm cells per second;
   h. establishing a skim milk solution into which said droplets separated based upon said sex characteristic of said equine sperm cells entrained are collected;
   i. collecting live equine sperm cells separated based upon said sex characteristic in said skim milk solution at a rate of at least nine hundred live equine sperm cells per second; and
   j. establishing an equine artificial insemination sample containing said live equine sperm cells separated based upon said sex characteristic which are capable of fertilizing at least one egg within a female of said species of equine mammal.

2. A method of establishing an equine artificial insemination sample for equine artificial insemination as described in claim 1 wherein said step of establishing a skim milk solution into which said equine sperm cells are collected comprises the step of establishing a solution containing a skim milk extender as a collection fluid.

3. A method of establishing an equine artificial insemination sample for equine artificial insemination as described in claim 2 wherein said step of establishing a skim milk solution into which said equine sperm cells are collected further comprises the step of establishing a solution containing about four percent egg yolk as a collection fluid.

4. A method of establishing an equine artificial insemination sample for equine artificial insemination as described in claim 1 wherein said sheath fluid contains a HEPES buffered medium.

5. A method of establishing an equine artificial insemination sample for equine artificial insemination as described in claim 1 wherein said step of separating said droplets based upon said sex characteristic of said equine sperm cells further comprises the step of sorting said droplets having said equine sperm cells entrained using a flow cytometer.

6. A method of establishing an equine artificial insemination sample for equine artificial insemination as described in claim 5 wherein said step of sorting said droplets having said equine sperm cells entrained comprises the step of operating said flow cytometer at a pressure of at least about fifty pounds per square inch.

7. A method of establishing an equine artificial insemination sample for equine artificial insemination as described in claim 1 wherein said equine artificial insemination sample is selected from the group consisting of: an equine artificial insemination sample of no more than about five million equine sperm cells, and an equine artificial insemination sample of no more than about twenty-five million equine sperm cells.

8. A method of establishing an equine artificial insemination sample for equine artificial insemination as described in claim 1 wherein said equine artificial insemination sample has a volume selected from the group consisting of: 0.2 ml, and 1 ml.

* * * * *